(12) United States Patent
Wallach et al.

(10) Patent No.: US 7,419,804 B2
(45) Date of Patent: Sep. 2, 2008

(54) CASH (CASPASE HOMOLOGUE) WITH DEATH EFFECTOR DOMAIN, MODULATORS OF THE FUNCTION OF FAS

(75) Inventors: David Wallach, Rehovot (IL); Yura Goltsev, Rehovot (IL); Andrei Kovalenko, Rehovot (IL); Eugene Varfolomeev, Rehovot (IL); Vadim Brodianski, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 11/448,842

(22) Filed: Jun. 8, 2006

(65) Prior Publication Data

US 2006/0216788 A1 Sep. 28, 2006

Related U.S. Application Data

(60) Division of application No. 10/849,901, filed on May 21, 2004, now abandoned, which is a continuation of application No. 09/380,546, filed as application No. PCT/IL98/00098 on Feb. 26, 1998, now abandoned.

(30) Foreign Application Priority Data

| Mar. 3, 1997 | (IL) | ................................ | 120367 |
| May 1, 1997 | (IL) | ................................ | 120759 |

(51) Int. Cl.
| C12P 21/06 | (2006.01) |
| C12P 21/04 | (2006.01) |
| C07H 21/04 | (2006.01) |
| C12N 15/00 | (2006.01) |
| C12N 5/00 | (2006.01) |
| G01N 33/03 | (2006.01) |

(52) U.S. Cl. .................. 435/69.1; 536/23.5; 435/320.1; 435/325; 435/7.1; 435/71.2

(58) Field of Classification Search ........................ None
See application file for complete search history.

(56) References Cited

U.S. PATENT DOCUMENTS 6,207,458 B1 * 3/2001 Chaudhary et al. ............. 435/6
6,242,569 B1   6/2001 Shu et al.
6,623,938 B2   9/2003 Ni et al.
2002/0052474 A1   5/2002 Shu et al.
2002/0095030 A1 * 7/2002 Tschopp et al. ............ 536/23.1

FOREIGN PATENT DOCUMENTS

| CA | 2278349 | 3/1998 |
| CA | 2226973 | 5/1998 |
| EP | 0841399 | 5/1998 |
| WO | WO98/44104 A2 | 3/1998 |

OTHER PUBLICATIONS

Chinnaiyan et al, "The cell-death machine", *Cur Biol* 6(5):555-563 (1996).
Han et al., MRIT, a novel death-effector domain-containing protein, interacts with caspases and BcLXL and initiates cell death, *Proc. Natl. Acad. Sci*, 94:11333-11338 (1997).
Goltsev et al., CASH, a novel caspase homologue with death effector domains, *J Biol Chem*. 272:19641-19644 (1997).
XP-002071908—Takeda, Human pancreatic islet cDNA, Accession No. C055730, *EMBL/GenBank/DDBJ databases*, (1996).
XP-002071907—Hillier et al., Homo sapiens cDNA clone, Accession No. AA149562, *EMBL/GenBank/DDBJ databases*, (1996).
XP-002071906—Hillier et al., Soares senescent fibroblasts nBHSF Homo sapiens cDNA, Accession No. N94588, *EMBL/GenBank/DDBJ databases*, (1996).
Srinivasula et al., FLAME-1, a novel FADD-like anti-apoptotic molecule that regulates Fas/TNFR1-induced apoptosis, *J Biol Chem.*, 272(30):18542-18545 (1997).
Phillips, The challenge of gene therapy and DNA delivery, *J. Pharm Pharmacology*, 53:1169-1174 (2001).
Bowie et al., Deciphering the Message in Protein Sequences: Tolerance to Amino Acid Substitutions, *Science*, 247:1306-1310 (1990).
Wells, Additivity of mutational effects in proteins, *Biochemistry*, 29:8509-8517 (1990).
Ngo et al., Computational complexity, protein structure prediction, and the levinthal paradox, in *The Protein Folding Problem and Tertiary Structure Prediction*, 491-495 (1994).
EM Phizicky et al., Microbiological Reviews, Protein-protein interactions: methods for detection and analysis, 59(1):94-123 (1995).

* cited by examiner

*Primary Examiner*—Lorraine Spector
*Assistant Examiner*—Shulamith H Shafer
(74) *Attorney, Agent, or Firm*—Browdy and Neimark, PLLC

(57) ABSTRACT

Proteins capable of modulating or mediating the function of MORT-1 are disclosed. Also disclosed are DNA sequences encoding these proteins, the recombinant production of these proteins as well as their use.

21 Claims, 11 Drawing Sheets

Fig. 1A

```
mCASHα  LIASDQLNLLEKCLKNIHRIDLNTKIQKYTQSSQGA·RSNMNTLQASLPK··LSIKYNSRLQNGRSKEPRFVEYRDSQRTLVKTS  232
hCASHβ  LVAPDQLDLLEKCLKNIHRIDLKTKIQKYKQSVQGAGTSYRNVLQAAIQKSLKDPSNNFRMITPYAHCPDLKILGNCSM*      222
hCASHα  LVAPDQLDLLEKCLKNIHRIDLKIKIQKYKQSVQGAGTSYRNVLQAAIQKSLKDPSNNFRLHNGRSKEQRLKEQLGAQQEPVKKS 227
CASP-8  ILGEGKLDILKRVCAQINKSLLKIINDYEE··········FSKERSSSLEGS·PDE·······FSNGEELCGVMTISDSPREQD 216
CASP-10 KIDEDNLTCLEDICKTVV·PKLLRNLEKYK·············REKAIQIVTP·PVD·······KEAESYQGEEELVSQTDVKTF 223
CASP-1                                ...QGVLSSFPAPQAVQDNPAMPTSSGSEGNVKLCSLEEAQ 142
                                                    ↳p20
```

```
mCASHα  IQESGAFLPPHIREETYRMQS····KPLGICLIIDCIGNDT················KYLQETFTSLGYHIQLFLFPKSH 292
hCASHα  IQESEAFLPQSIPEERYKMKS····KPLGICLIIDCIGNET················ELLRDTFTSLGYEVQKFLHLSMH 287
CASP-8  S·ES······QTLDKVYQMKS····KPRGYCLINNHNFAKAREKVPKLHSIRDRNGTHLDAGALTTTFEELHFEIKPHDDCT·V 283
CASP-10 L·EA······LPRAAVYRMNR····NHRGLCVIVNNHSFT········SLKDRQGTHKDAEIILSHVFQWLGFTVHIHNNVTKV 287
CASP-3  ...SG······ISLDNSYKMDY····PEMGLCIIINNKNFHKS·······TGMTSRSGTDVDAANLRETFRNLKYEVRNKNDLT·R 92
CASP-1  RIWK······QKSAEIYPIM·DKSSRT·RLALIICNEEFDS··········IPRRTGAEVDITGMTMLLQHLGYSVDVKKNLT·A 207
                                                                                O
```

Fig. 1B

```
mCASHα  DITQIVRRYASMAQ·HQDYDSFACVLVSLLGGSQSMMGRD·····QVHSGFSLDHVKNMFTGDTCPSLRGKPKLFFIQNYESLGS 370
hCASHα  GISQILGQFACMPE·HRQYDSFVQVLVSLRGGSQSVYGVD·····QTHSGLPLHHLRRMFMGDSCPYLAGKPKMFFIQNYVVSEG 385
CASP-8  EQIYEIWKIYQLMD·HSNMDCFICILLSHGDKGIIYGTD······GQEG··PIYELTSQFTGLKCPSLAGKPKVFFIQACQGDN· 364
CASP-10 EMEMVLQKQKCNPA·HADGQCFVFECILTHGRFGAVYSSD······EALI··PINELMSHFTALQCPSLAEKPKVFFIQACQGEE· 362
CASP-3  EGIVELMRDVSKED·HSKRSSFVCVLLSHGEEGIIFGTN······G·PV·DLKKITNFFRGDRCRSLTGKPKLFIIQACRGTE· 166
CASP-1  SDMTTELEAFAHRPE·HKTSDSTFLVFMSHGIREGICGKKHSEQVPD·IL··QLNAIFNMLNTKNCPSLKDKPKVIILQACRGDS· 288
                                                    ●                   O ●
```

```
mCASHα  GLEDSS·LEVD············GPSIKNYDSKPLQPRHCTTHPEADFLFWSLCTADVSHLEKPSSSSSLYLQSLSQQLIKQGRN·P 442
hCASHα  QLENSSLLEVD············GPAMKNVEFKAQKRGLCTVHREADFLFWSLCTADMSLLEQSHSSPSLYLQCLSQKLRGERN·P 438
CASP-8  ·YQKGIPVETD············SEEQPYLEMDLSSPQTRYIPDEADFLLGMATVNNCVSYRNPAEGTWYIQSLCQSLRERCPR·L 435
CASP-10 ·IQPSVSIEAD············ALNPEQAPTSLQDS···IPAEADFLLGLATVPGYVSFRNYEEGSWYIQSLCNHLKKLVPR·L 429
CASP-3  ···LDCGIETD············SG···VQDDMACHK····IPVEADFLYAYSTAPGYYSWRNSKDGSWFIQSLCAMLKGYADK· 277
CASP-1  ···PGVYWFKESVGVSGNLSLPTTE····EFEDDAIKK····AHIEKDFIAFCSSTPDNVSWRHPTMGSVFIGRLIEHMQEYACS· 381
                                                                            O   O
                                                                               466
mCASHα  LVDLHVEL·MQKVYAWNSGYSSK········EKYSLSLQ·HTLRKKLLLAPT*                              466
hCASHα  LLDKHISILNGY·MYDWNSRVSAK········EKYYVWLQ·HTLRKKLLSYT*                              461
CASP-8  GDDILYDILTEV·NYEVSNKDDKK········NMGKYIPPT·FTLRKKLVFPSG*                             479
CASP-10 HEDILSIHLTAV·NDDVSRRVDKQ······GTKKKMPQPA·FTLRKKLVFPVPLDALSI*                        480
CASP-3  ·LEFMHIHLTRV·NRKVATEFESFSFDATFHAKKQIPCIV·SMLTKELYFYH*                               277
CASP-1  ·CQVEEDFRKV·RFSFEQ·PD·········GRAQMPTTERVLTRCFYLFPGH*                              404
```

Fig. 1C

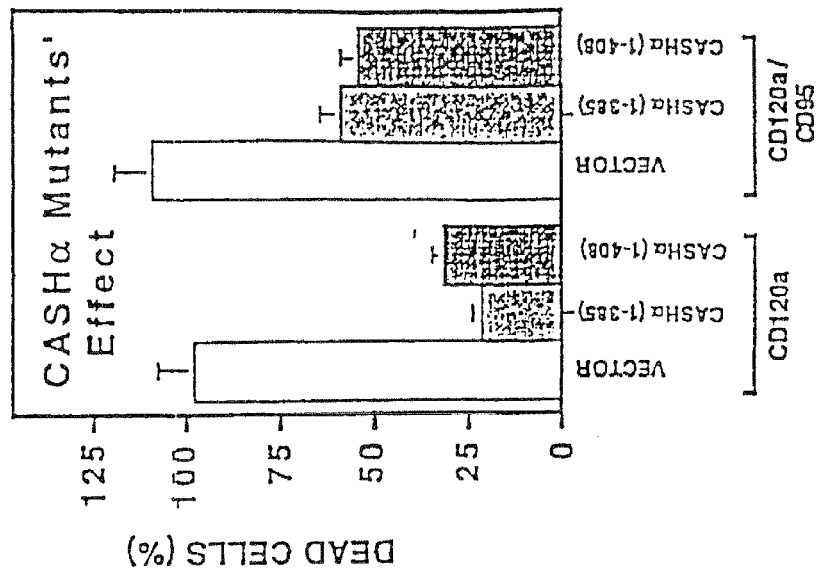
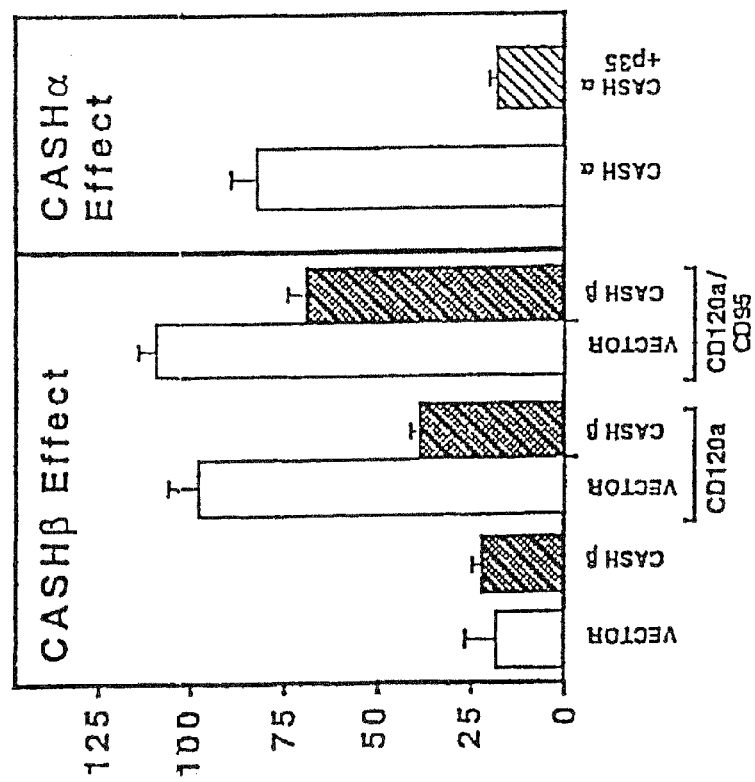
Fig. 4B
Fig. 4C

293-T cells

Vector

CASH α

CD120a

CD120a+CASH α (1-4;

SEQUENCE LISTING

```
<160> NUMBER OF SEQ ID NOS: 20

<210> SEQ ID NO 1
<211> LENGTH: 2243
<212> TYPE: DNA
<213> ORGANISM: Homo sapiens
<220> FEATURE:
<221> NAME/KEY: CDS
<222> LOCATION: (482)..(1921)

<400> SEQUENCE: 1
ggacgtcgag gcattacaat cgcgaaacca agccatagca tgaaacagcg agcttgcagc      60
ctcaccgacg agtctcaact aaaagggact cccggagcta ggggtgggga ctcggcctca     120
cacagtgagt gccggctatt ggacttttgt ccagtgacag ctgagacaac aaggaccacg     180
ggaggaggtg taggagagaa gcgccgcgaa cagcgatcgc ccagcaccaa gtccgcttcc     240
aggctttcgg tttctttgcc tccatcttgg gtgcgccttc ccggcgtcta ggggagcgaa     300
ggctgaggtg gcagcggcag gagagtccgg ccgcgacagg acgaactccc ccactggaaa     360
ggattctgaa agaaatgaag tcagccctca gaaatgaagt tgactgcctg ctggctttcc     420
tgttgactgg cccggagctg tactgcaaga cccttgtgag cttccctagt ctaagagtag     480 g atg tct gct gaa gtc atc cat cag gtt gaa gaa gca ctt gat aca gat     529
  Met Ser Ala Glu Val Ile His Gln Val Glu Glu Ala Leu Asp Thr Asp
   1               5                  10                  15 gag aag gag atg ctg ctc ttt ttg tgc cgg gat gtt gct ata gat gtg     577
Glu Lys Glu Met Leu Leu Phe Leu Cys Arg Asp Val Ala Ile Asp Val
                20                  25                  30 gtt cca cct aat gtc agg gac ctt ctg gat att tta cgg gaa aga ggt     625
Val Pro Pro Asn Val Arg Asp Leu Leu Asp Ile Leu Arg Glu Arg Gly
            35                  40                  45 aag ctg tct gtc ggg gac ttg gct gaa ctg ctc tac aga gtg agg cga     673
Lys Leu Ser Val Gly Asp Leu Ala Glu Leu Leu Tyr Arg Val Arg Arg
        50                  55                  60 ttt gac ctg ctc aaa cgt atc ttg aag atg gac aga aaa gct gtg gag     721
Phe Asp Leu Leu Lys Arg Ile Leu Lys Met Asp Arg Lys Ala Val Glu
    65                  70                  75                  80 acc cac ctg ctc agg aac cct cac ctt gtt tcg gac tat aga gtg ctg     769
Thr His Leu Leu Arg Asn Pro His Leu Val Ser Asp Tyr Arg Val Leu
                85                  90                  95 atg gca gag att ggt gag gat ttg gat aaa tct gat gtg tcc tca tta     817
Met Ala Glu Ile Gly Glu Asp Leu Asp Lys Ser Asp Val Ser Ser Leu
```

-continued

```
                      100                 105                 110
att ttc ctc atg aag gat tac atg ggc cga ggc aag ata agc aag gag        865
Ile Phe Leu Met Lys Asp Tyr Met Gly Arg Gly Lys Ile Ser Lys Glu
        115                 120                 125 aag agt ttc ttg gac ctt gtg gtt gag ttg gag aaa cta aat ttg gtt        913
Lys Ser Phe Leu Asp Leu Val Val Glu Leu Glu Lys Leu Asn Leu Val
130                 135                 140 gcc cca gat caa ctg gat tta tta gaa aaa tgc cta aag aac atc cac        961
Ala Pro Asp Gln Leu Asp Leu Leu Glu Lys Cys Leu Lys Asn Ile His
        145                 150                 155                 160 aga ata gac ctg aag aca aaa atc cag aag tac aag cag tct gtt caa       1009
Arg Ile Asp Leu Lys Thr Lys Ile Gln Lys Tyr Lys Gln Ser Val Gln
                165                 170                 175 gga gca ggg aca agt tac agg aat gtt ctc caa gca gca atc caa aag       1057
Gly Ala Gly Thr Ser Tyr Arg Asn Val Leu Gln Ala Ala Ile Gln Lys
                180                 185                 190 agt ctc aag gat cct tca aat aac ttc agg ctc cat aat ggg aga agt       1105
Ser Leu Lys Asp Pro Ser Asn Asn Phe Arg Leu His Asn Gly Arg Ser
            195                 200                 205 aaa gaa caa aga ctt aag gaa cag ctt ggc gct caa caa gaa cca gtg       1153
Lys Glu Gln Arg Leu Lys Glu Gln Leu Gly Ala Gln Gln Glu Pro Val
210                 215                 220 aag aaa tcc att cag gaa tca gaa gct ttt ttg cct cag agc ata cct       1201
Lys Lys Ser Ile Gln Glu Ser Glu Ala Phe Leu Pro Gln Ser Ile Pro
225                 230                 235                 240 gaa gag aga tac aag atg aag agc aag ccc cta gga atc tgc ctg ata       1249
Glu Glu Arg Tyr Lys Met Lys Ser Lys Pro Leu Gly Ile Cys Leu Ile
                245                 250                 255 atc gat tgc att ggc aat gag aca gag ctt ctt cga gac acc ttc act       1297
Ile Asp Cys Ile Gly Asn Glu Thr Glu Leu Leu Arg Asp Thr Phe Thr
                260                 265                 270 tcc ctg ggc tat gaa gtc cag aaa ttc ttg cat ctc agt atg cat ggt       1345
Ser Leu Gly Tyr Glu Val Gln Lys Phe Leu His Leu Ser Met His Gly
            275                 280                 285 ata tcc cag att ctt ggc caa ttt gcc tgt atg ccc gag cac cga gac       1393
Ile Ser Gln Ile Leu Gly Gln Phe Ala Cys Met Pro Glu His Arg Asp
290                 295                 300 tac gac agc ttt gtg tgt gtc ctg gtg agc cga gga ggc tcc cag agt       1441
Tyr Asp Ser Phe Val Cys Val Leu Val Ser Arg Gly Gly Ser Gln Ser
305                 310                 315                 320 gtg tat ggt gtg gat cag act cac tca ggg ctc ccc ctg cat cac atc       1489
Val Tyr Gly Val Asp Gln Thr His Ser Gly Leu Pro Leu His His Ile
                325                 330                 335 agg agg atg ttc atg gga gat tca tgc cct tat cta gca ggg aag cca       1537
Arg Arg Met Phe Met Gly Asp Ser Cys Pro Tyr Leu Ala Gly Lys Pro
                340                 345                 350 aag atg ttt ttt att cag aac tat gtg gtg tca gag ggc cag ctg gag       1585
Lys Met Phe Phe Ile Gln Asn Tyr Val Val Ser Glu Gly Gln Leu Glu
            355                 360                 365 aac agc agc ctc ttg gag gtg gat ggg cca gcg atg aag aat gtg gaa       1633
Asn Ser Ser Leu Leu Glu Val Asp Gly Pro Ala Met Lys Asn Val Glu
370                 375                 380 ttc aag gct cag aag cga ggg ctg tgc aca gtt cac cga gaa gct gac       1681
Phe Lys Ala Gln Lys Arg Gly Leu Cys Thr Val His Arg Glu Ala Asp
385                 390                 395                 400 ttc ttc tgg agc ctg tgt act gcg gac atg tcc ctg ctg gag cag tct       1729
Phe Phe Trp Ser Leu Cys Thr Ala Asp Met Ser Leu Leu Glu Gln Ser
                405                 410                 415 cac agc tca ccg tcc ctg tac ctg cag tgc ctc tcc cag aaa ctg aga       1777
```

-continued

```
                His Ser Ser Pro Ser Leu Tyr Leu Gln Cys Leu Ser Gln Lys Leu Arg
                            420                 425                 430 caa gaa aga aaa cgc cca ctc ctg gat ctt cac att gaa ctc aat ggc         1825
Gln Glu Arg Lys Arg Pro Leu Leu Asp Leu His Ile Glu Leu Asn Gly
        435                 440                 445 tac atg tat gat tgg aac agc aga gtt tct gcc aag gag aaa tat tat         1873
Tyr Met Tyr Asp Trp Asn Ser Arg Val Ser Ala Lys Glu Lys Tyr Tyr
    450                 455                 460 gtc tgg ctg cag cac act ctg aga aag aaa ctt atc ctc tcc tac aca         1921
Val Trp Leu Gln His Thr Leu Arg Lys Lys Leu Ile Leu Ser Tyr Thr
465                 470                 475                 480 taagaaacca aaaggctggg cgtagtggct cacacctgta atcccagcac tttgggaggc       1981
caaggagggc agatcacttc aggtcaggag ttcgagacca gcctggccaa catggtaaac       2041
gctgtcccta gtaaaaatgc aaaaattagc tgggtgtggg tgtgggtacc tgtgttccca      2101
gttacttggg aggctgaggt gggaggatct tttgaaccca ggagttcagg gtcatagcat       2161
gctgtgattg tgcctacgaa tagccactgc ataccaacct gggcaatata gcaagatccc      2221
atctctttaa aaaaaaaaaa aa                                                2243
```

<210> SEQ ID NO 2
<211> LENGTH: 480
<212> TYPE: PRT
<213> ORGANISM: Homo sapiens

<400> SEQUENCE: 2

```
Met Ser Ala Glu Val Ile His Gln Val Glu Glu Ala Leu Asp Thr Asp
1               5                   10                  15

Glu Lys Glu Met Leu Leu Phe Leu Cys Arg Asp Val Ala Ile Asp Val
            20                  25                  30

Val Pro Pro Asn Val Arg Asp Leu Leu Asp Ile Leu Arg Glu Arg Gly
        35                  40                  45

Lys Leu Ser Val Gly Asp Leu Ala Glu Leu Leu Tyr Arg Val Arg Arg
    50                  55                  60

Phe Asp Leu Leu Lys Arg Ile Leu Lys Met Asp Arg Lys Ala Val Glu
65                  70                  75                  80

Thr His Leu Leu Arg Asn Pro His Leu Val Ser Asp Tyr Arg Val Leu
                85                  90                  95

Met Ala Glu Ile Gly Glu Asp Leu Asp Lys Ser Asp Val Ser Ser Leu
            100                 105                 110

Ile Phe Leu Met Lys Asp Tyr Met Gly Arg Gly Lys Ile Ser Lys Glu
        115                 120                 125

Lys Ser Phe Leu Asp Leu Val Val Glu Leu Glu Lys Leu Asn Leu Val
    130                 135                 140

Ala Pro Asp Gln Leu Asp Leu Leu Glu Lys Cys Leu Lys Asn Ile His
145                 150                 155                 160

Arg Ile Asp Leu Lys Thr Lys Ile Gln Lys Tyr Lys Gln Ser Val Gln
                165                 170                 175

Gly Ala Gly Thr Ser Tyr Arg Asn Val Leu Gln Ala Ala Ile Gln Lys
            180                 185                 190

Ser Leu Lys Asp Pro Ser Asn Asn Phe Arg Leu His Asn Gly Arg Ser
        195                 200                 205

Lys Glu Gln Arg Leu Lys Glu Gln Leu Gly Ala Gln Gln Glu Pro Val
    210                 215                 220

Lys Lys Ser Ile Gln Glu Ser Glu Ala Phe Leu Pro Gln Ser Ile Pro
225                 230                 235                 240
```

-continued

```
Glu Glu Arg Tyr Lys Met Lys Ser Lys Pro Leu Gly Ile Cys Leu Ile
                245                 250                 255
Ile Asp Cys Ile Gly Asn Glu Thr Glu Leu Leu Arg Asp Thr Phe Thr
            260                 265                 270
Ser Leu Gly Tyr Glu Val Gln Lys Phe Leu His Leu Ser Met His Gly
        275                 280                 285
Ile Ser Gln Ile Leu Gly Gln Phe Ala Cys Met Pro Glu His Arg Asp
    290                 295                 300
Tyr Asp Ser Phe Val Cys Val Leu Val Ser Arg Gly Gly Ser Gln Ser
305                 310                 315                 320
Val Tyr Gly Val Asp Gln Thr His Ser Gly Leu Pro Leu His His Ile
                325                 330                 335
Arg Arg Met Phe Met Gly Asp Ser Cys Pro Tyr Leu Ala Gly Lys Pro
            340                 345                 350
Lys Met Phe Phe Ile Gln Asn Tyr Val Val Ser Glu Gly Gln Leu Glu
        355                 360                 365
Asn Ser Ser Leu Leu Glu Val Asp Gly Pro Ala Met Lys Asn Val Glu
    370                 375                 380
Phe Lys Ala Gln Lys Arg Gly Leu Cys Thr Val His Arg Glu Ala Asp
385                 390                 395                 400
Phe Phe Trp Ser Leu Cys Thr Ala Asp Met Ser Leu Leu Glu Gln Ser
                405                 410                 415
His Ser Ser Pro Ser Leu Tyr Leu Gln Cys Leu Ser Gln Lys Leu Arg
            420                 425                 430
Gln Glu Arg Lys Arg Pro Leu Leu Asp Leu His Ile Glu Leu Asn Gly
        435                 440                 445
Tyr Met Tyr Asp Trp Asn Ser Arg Val Ser Ala Lys Glu Lys Tyr Tyr
    450                 455                 460
Val Trp Leu Gln His Thr Leu Arg Lys Lys Leu Ile Leu Ser Tyr Thr
465                 470                 475                 480

<210> SEQ ID NO 3
<211> LENGTH: 1373
<212> TYPE: DNA
<213> ORGANISM: Homo sapiens
<220> FEATURE:
<221> NAME/KEY: CDS
<222> LOCATION: (482)..(1144)

<400> SEQUENCE: 3
```

| | |
|---|---|
| ggacgtcgag gcattacaat cgcgaaacca agccatagca tgaaacagcg agcttgcagc | 60 |
| ctcaccgacg agtctcaact aaaagggact cccggagcta ggggtgggga ctcggcctca | 120 |
| cacagtgagt gccggctatt ggacttttgt ccagtgacag ctgagacaac aaggaccacg | 180 |
| ggaggaggtg taggagagaa cgccgcgaa cagcgatcgc ccagcaccaa gtccgcttcc | 240 |
| aggctttcgg tttctttgcc tccatcttgg gtgcgccttc ccggcgtcta ggggagcgaa | 300 |
| ggctgaggtg gcagcggcag gagagtccgg ccgcgacagg acgaactccc ccactggaaa | 360 |
| ggattctgaa agaaatgaag tcagccctca gaaatgaagt tgactgcctg ctggcttttcc | 420 |
| tgttgactgg cccggagctg tactgcaaga cccttgtgag cttccctagt ctaagagtag | 480 |

```
g atg tct gct gaa gtc atc cat cag gtt gaa gaa gca ctt gat aca gat     529
  Met Ser Ala Glu Val Ile His Gln Val Glu Glu Ala Leu Asp Thr Asp
   1               5                  10                  15 gag aag gag atg ctg ctc ttt ttg tgc cgg gat gtt gct ata gat gtg     577
Glu Lys Glu Met Leu Leu Phe Leu Cys Arg Asp Val Ala Ile Asp Val
```

-continued

```
                 20                  25                  30
gtt cca cct aat gtc agg gac ctt ctg gat att tta cgg gaa aga ggt      625
Val Pro Pro Asn Val Arg Asp Leu Leu Asp Ile Leu Arg Glu Arg Gly
             35                  40                  45 aag ctg tct gtc ggg gac ttg gct gaa ctg ctc tac aga gtg agg cga      673
Lys Leu Ser Val Gly Asp Leu Ala Glu Leu Leu Tyr Arg Val Arg Arg
 50                  55                  60 ttt gac ctg ctc aaa cgt atc ttg aag atg gac aga aaa gct gtg gag      721
Phe Asp Leu Leu Lys Arg Ile Leu Lys Met Asp Arg Lys Ala Val Glu
 65                  70                  75                  80 acc cac ctg ctc agg aac cct cac ctt gtt tcg gac tat aga gtg ctg      769
Thr His Leu Leu Arg Asn Pro His Leu Val Ser Asp Tyr Arg Val Leu
                 85                  90                  95 atg gca gag att ggt gag gat ttg gat aaa tct gat gtg tcc tca tta      817
Met Ala Glu Ile Gly Glu Asp Leu Asp Lys Ser Asp Val Ser Ser Leu
            100                 105                 110 att ttc ctc atg aag gat tac atg ggc cga ggc aag ata agc aag gag      865
Ile Phe Leu Met Lys Asp Tyr Met Gly Arg Gly Lys Ile Ser Lys Glu
            115                 120                 125 aag agt ttc ttg gac ctt gtg gtt gag ttg gag aaa cta aat ttg gtt      913
Lys Ser Phe Leu Asp Leu Val Val Glu Leu Glu Lys Leu Asn Leu Val
130                 135                 140 gcc cca gat caa ctg gat tta tta gaa aaa tgc cta aag aac atc cac      961
Ala Pro Asp Gln Leu Asp Leu Leu Glu Lys Cys Leu Lys Asn Ile His
145                 150                 155                 160 aga ata gac ctg aag aca aaa atc cag aag tac aag cag tct gtt caa     1009
Arg Ile Asp Leu Lys Thr Lys Ile Gln Lys Tyr Lys Gln Ser Val Gln
                165                 170                 175 gga gca ggg aca agt tac agg aat gtt ctc caa gca gca atc caa aag     1057
Gly Ala Gly Thr Ser Tyr Arg Asn Val Leu Gln Ala Ala Ile Gln Lys
            180                 185                 190 agt ctc aag gat cct tca aat aac ttc agg atg ata aca ccc tat gcc     1105
Ser Leu Lys Asp Pro Ser Asn Asn Phe Arg Met Ile Thr Pro Tyr Ala
        195                 200                 205 cat tgt cct gat ctg aaa att ctt gga aat tgt tcc atg tgattaacat      1154
His Cys Pro Asp Leu Lys Ile Leu Gly Asn Cys Ser Met
    210                 215                 220 ggaactgcct ctacttaatc attctgaatg attaaatcgt ttcatttct aaatgtgtta   1214 taatgtgttt agccctttct tgttgctgta tgtttagatg ctttccaatc ttttgttact   1274
actaataatg ctataaaata aatatccttg tacttcttaa aaaaaaaaa aaaaaaaaa    1334 aaaaaaaaaa aaaaaaaaa aaaaaaaaa aaaaaaaa                           1373
```

<210> SEQ ID NO 4
<211> LENGTH: 221
<212> TYPE: PRT
<213> ORGANISM: Homo sapiens

<400> SEQUENCE: 4

```
Met Ser Ala Glu Val Ile His Gln Val Glu Glu Ala Leu Asp Thr Asp
  1               5                  10                  15

Glu Lys Glu Met Leu Leu Phe Leu Cys Arg Asp Val Ala Ile Asp Val
             20                  25                  30

Val Pro Pro Asn Val Arg Asp Leu Leu Asp Ile Leu Arg Glu Arg Gly
         35                  40                  45

Lys Leu Ser Val Gly Asp Leu Ala Glu Leu Leu Tyr Arg Val Arg Arg
     50                  55                  60

Phe Asp Leu Leu Lys Arg Ile Leu Lys Met Asp Arg Lys Ala Val Glu
```

```
                65                  70                  75                  80
Thr His Leu Leu Arg Asn Pro His Leu Val Ser Asp Tyr Arg Val Leu
                    85                  90                  95

Met Ala Glu Ile Gly Glu Asp Leu Asp Lys Ser Asp Val Ser Ser Leu
                100                 105                 110

Ile Phe Leu Met Lys Asp Tyr Met Gly Arg Gly Lys Ile Ser Lys Glu
                115                 120                 125

Lys Ser Phe Leu Asp Leu Val Val Glu Leu Glu Lys Leu Asn Leu Val
            130                 135                 140

Ala Pro Asp Gln Leu Asp Leu Leu Glu Lys Cys Leu Lys Asn Ile His
145                 150                 155                 160

Arg Ile Asp Leu Lys Thr Lys Ile Gln Lys Tyr Lys Gln Ser Val Gln
                165                 170                 175

Gly Ala Gly Thr Ser Tyr Arg Asn Val Leu Gln Ala Ala Ile Gln Lys
                180                 185                 190

Ser Leu Lys Asp Pro Ser Asn Asn Phe Arg Met Ile Thr Pro Tyr Ala
            195                 200                 205

His Cys Pro Asp Leu Lys Ile Leu Gly Asn Cys Ser Met
210                 215                 220

<210> SEQ ID NO 5
<211> LENGTH: 484
<212> TYPE: PRT
<213> ORGANISM: Mus musculus

<400> SEQUENCE: 5

Met Ala Gln Ser Pro Val Ser Ala Glu Val Ile His Gln Val Glu Glu
 1               5                  10                  15

Cys Leu Asp Glu Asp Glu Lys Glu Met Met Leu Phe Leu Cys Arg Asp
                20                  25                  30

Val Thr Glu Asn Leu Ala Ala Pro Asn Val Arg Asp Leu Leu Asp Ser
            35                  40                  45

Leu Ser Glu Arg Gly Gln Leu Ser Phe Ala Thr Leu Ala Glu Leu Leu
        50                  55                  60

Tyr Arg Val Arg Arg Phe Asp Leu Leu Lys Arg Ile Leu Lys Thr Asp
65                  70                  75                  80

Lys Ala Thr Val Glu Asp His Leu Arg Arg Asn Pro His Leu Val Ser
                85                  90                  95

Asp Tyr Arg Val Leu Leu Met Glu Ile Gly Glu Ser Leu Asp Gln Asn
                100                 105                 110

Asp Val Ser Ser Leu Val Phe Leu Thr Arg Ile Thr Arg Asp Tyr Thr
            115                 120                 125

Gly Arg Gly Lys Ile Ala Lys Asp Lys Ser Phe Leu Asp Leu Val Ile
        130                 135                 140

Glu Leu Glu Lys Leu Asn Leu Ile Ala Ser Asp Gln Leu Asn Leu Leu
145                 150                 155                 160

Glu Lys Cys Leu Lys Asn Ile His Arg Ile Asp Leu Asn Thr Lys Ile
                165                 170                 175

Gln Lys Tyr Thr Gln Ser Ser Gln Gly Ala Arg Ser Asn Met Asn Thr
                180                 185                 190

Leu Gln Ala Ser Leu Pro Lys Leu Ser Ile Lys Tyr Asn Ser Arg Leu
            195                 200                 205

Gln Asn Gly Arg Ser Lys Glu Pro Arg Phe Val Glu Tyr Arg Asp Ser
210                 215                 220
```

-continued

```
Gln Arg Thr Leu Val Lys Thr Ser Ile Gln Glu Ser Gly Ala Phe Leu
225                 230                 235                 240

Pro Pro His Ile Arg Glu Thr Tyr Arg Met Gln Ser Lys Pro Leu
            245                 250                 255

Gly Ile Cys Leu Ile Ile Asp Cys Ile Gly Asn Asp Thr Lys Tyr Leu
            260                 265                 270

Gln Glu Thr Phe Thr Ser Leu Gly Tyr His Ile Gln Leu Phe Leu Phe
            275                 280                 285

Pro Lys Ser His Asp Ile Thr Gln Ile Val Arg Arg Tyr Ala Ser Met
            290                 295                 300

Ala Gln His Gln Asp Tyr Asp Ser Phe Ala Cys Val Leu Val Ser Leu
305                 310                 315                 320

Gly Gly Ser Gln Ser Met Met Gly Arg Asp Gln Val His Ser Gly Phe
            325                 330                 335

Ser Leu Asp His Val Lys Asn Met Phe Thr Gly Asp Thr Cys Pro Ser
            340                 345                 350

Leu Arg Gly Lys Pro Lys Leu Phe Phe Ile Gln Asn Tyr Glu Ser Leu
            355                 360                 365

Gly Ser Gln Leu Glu Asp Ser Ser Leu Glu Val Asp Gly Pro Ser Ile
            370                 375                 380

Lys Asn Val Asp Ser Lys Pro Leu Gln Pro Arg His Cys Thr Thr His
385                 390                 395                 400

Pro Glu Ala Asp Ile Phe Trp Ser Leu Cys Thr Ala Asp Val Ser His
            405                 410                 415

Leu Glu Lys Pro Ser Ser Ser Ser Val Tyr Leu Gln Lys Leu Ser
            420                 425                 430

Gln Gln Leu Lys Gln Gly Arg Arg Pro Leu Val Asp Leu His Val
            435                 440                 445

Glu Leu Met Asp Lys Val Tyr Ala Trp Asn Ser Gly Val Ser Ser Lys
450                 455                 460

Glu Lys Tyr Ser Leu Ser Leu Gln His Thr Leu Arg Lys Lys Leu Ile
465                 470                 475                 480

Leu Ala Pro Thr

<210> SEQ ID NO 6
<211> LENGTH: 479
<212> TYPE: PRT
<213> ORGANISM: Homo sapiens

<400> SEQUENCE: 6

Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu
        35                  40                  45

Gln Glu Lys Arg Met Leu Glu Glu Ser Asn Leu Ser Phe Leu Lys Glu
    50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Val Met Leu Tyr Gln Ile Ser Glu Glu Val
            100                 105                 110
```

```
Ser Arg Ser Glu Leu Arg Ser Phe Lys Phe Leu Leu Gln Glu Glu Ile
        115                 120                 125

Ser Lys Cys Lys Leu Asp Asp Met Asn Leu Leu Asp Ile Phe Ile
130                 135                 140

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175

Asp Tyr Glu Glu Phe Ser Lys Glu Arg Ser Ser Leu Glu Gly Ser
            180                 185                 190

Pro Asp Glu Phe Ser Asn Gly Glu Glu Leu Cys Gly Val Met Thr Ile
            195                 200                 205

Ser Asp Ser Pro Arg Glu Gln Asp Ser Glu Ser Gln Thr Leu Asp Lys
        210                 215                 220

Val Tyr Gln Met Lys Ser Lys Pro Arg Gly Tyr Cys Leu Ile Ile Asn
225                 230                 235                 240

Asn His Asn Phe Ala Lys Ala Arg Glu Lys Val Pro Lys Leu His Ser
                245                 250                 255

Ile Arg Asp Arg Asn Gly Thr His Leu Asp Ala Gly Ala Leu Thr Thr
            260                 265                 270

Thr Phe Glu Glu Leu His Phe Glu Ile Lys Pro His Asp Asp Cys Thr
        275                 280                 285

Val Glu Gln Ile Tyr Glu Ile Leu Lys Ile Tyr Gln Leu Met Asp His
    290                 295                 300

Ser Asn Met Asp Cys Phe Ile Cys Cys Ile Leu Ser His Gly Asp Lys
305                 310                 315                 320

Gly Ile Ile Tyr Gly Thr Asp Gly Gln Glu Ala Pro Ile Tyr Glu Leu
                325                 330                 335

Thr Ser Gln Phe Thr Gly Leu Lys Cys Pro Ser Leu Ala Gly Lys Pro
            340                 345                 350

Lys Val Phe Phe Ile Gln Ala Cys Gln Gly Asp Asn Tyr Gln Lys Gly
        355                 360                 365

Ile Pro Val Glu Thr Asp Ser Glu Glu Gln Pro Tyr Leu Glu Met Asp
370                 375                 380

Leu Ser Ser Pro Gln Thr Arg Tyr Ile Pro Asp Glu Ala Asp Phe Leu
385                 390                 395                 400

Leu Gly Met Ala Thr Val Asn Asn Cys Val Ser Tyr Arg Asn Pro Ala
                405                 410                 415

Glu Gly Thr Trp Tyr Ile Gln Ser Leu Cys Gln Ser Leu Arg Glu Arg
            420                 425                 430

Cys Pro Arg Gly Asp Asp Ile Leu Thr Ile Leu Thr Glu Val Asn Tyr
        435                 440                 445

Glu Val Ser Asn Lys Asp Asp Lys Lys Asn Met Gly Lys Gln Met Pro
    450                 455                 460

Gln Pro Thr Phe Thr Leu Arg Lys Lys Leu Val Phe Pro Ser Asp
465                 470                 475

<210> SEQ ID NO 7
<211> LENGTH: 479
<212> TYPE: PRT
<213> ORGANISM: Homo sapiens

<400> SEQUENCE: 7

Met Lys Ser Gln Gly Gln His Trp Tyr Ser Ser Asp Lys Asn Cys
1               5                   10                  15
```

-continued

```
Lys Val Ser Phe Arg Glu Lys Leu Leu Ile Ile Asp Ser Asn Leu Gly
             20                  25                  30

Val Gln Asp Val Glu Asn Leu Lys Phe Leu Cys Ile Gly Leu Val Pro
         35                  40                  45

Asn Lys Lys Leu Glu Lys Ser Ser Ala Ser Asp Val Phe Glu His
 50                  55                  60

Leu Leu Ala Gly Asp Leu Leu Ser Glu Glu Asp Pro Phe Phe Leu Ala
 65                  70                  75                  80

Glu Leu Leu Tyr Ile Ile Arg Gln Lys Lys Leu Leu Gln His Leu Asn
                 85                  90                  95

Cys Thr Lys Glu Glu Val Glu Arg Leu Leu Pro Thr Arg Gln Arg Val
            100                 105                 110

Ser Leu Phe Arg Asn Leu Leu Tyr Glu Leu Ser Glu Gly Ile Asp Ser
        115                 120                 125

Glu Asn Leu Lys Asp Met Ile Phe Leu Leu Lys Asp Ser Leu Pro Lys
130                 135                 140

Thr Glu Met Thr Ser Leu Ser Phe Leu Ala Phe Leu Glu Lys Gln Gly
145                 150                 155                 160

Lys Ile Asp Glu Asp Asn Leu Thr Cys Leu Glu Asp Leu Cys Lys Thr
                165                 170                 175

Val Val Pro Lys Leu Leu Arg Asn Ile Glu Lys Tyr Lys Arg Glu Lys
            180                 185                 190

Ala Ile Gln Ile Val Thr Pro Pro Val Asp Lys Glu Ala Glu Ser Tyr
        195                 200                 205

Gln Gly Glu Glu Glu Leu Val Ser Gln Thr Asp Val Lys Thr Phe Leu
    210                 215                 220

Glu Ala Leu Pro Arg Ala Ala Val Tyr Arg Met Asn Arg Asn His Arg
225                 230                 235                 240

Gly Leu Cys Val Ile Val Asn Asn His Ser Phe Thr Ser Leu Lys Asp
                245                 250                 255

Arg Gln Gly Thr His Lys Asp Ala Glu Ile Leu Ser His Val Phe Gln
            260                 265                 270

Trp Leu Gly Phe Thr Val His Ile His Asn Asn Val Thr Lys Val Glu
        275                 280                 285

Met Glu Met Val Leu Gln Lys Gln Lys Cys Asn Pro Ala His Ala Asp
    290                 295                 300

Gly Asp Cys Phe Val Phe Cys Ile Leu Thr His Gly Arg Phe Gly Ala
305                 310                 315                 320

Val Tyr Ser Ser Asp Glu Ala Leu Ile Pro Ile Arg Glu Ile Met Ser
                325                 330                 335

His Phe Thr Ala Leu Gln Cys Pro Arg Leu Ala Glu Lys Pro Lys Leu
            340                 345                 350

Phe Phe Ile Gln Ala Cys Gln Gly Glu Glu Ile Gln Pro Ser Val Ser
        355                 360                 365

Ile Glu Ala Asp Ala Leu Asn Pro Glu Gln Ala Pro Thr Ser Leu Gln
    370                 375                 380

Asp Ser Ile Pro Ala Glu Ala Asp Phe Leu Leu Gly Leu Ala Thr Val
385                 390                 395                 400

Pro Gly Tyr Val Ser Phe Arg His Val Glu Glu Gly Ser Trp Tyr Ile
                405                 410                 415

Gln Ser Leu Cys Asn His Leu Lys Lys Leu Val Pro Arg His Glu Asp
            420                 425                 430
```

```
Ile Leu Ser Ile Leu Thr Ala Val Asn Asp Asp Val Ser Arg Arg Val
            435                 440                 445
Asp Lys Gln Gly Thr Lys Lys Gln Met Pro Gln Pro Ala Phe Thr Leu
    450                 455                 460
Arg Lys Lys Leu Val Phe Pro Val Pro Leu Asp Ala Leu Ser Ile
465                 470                 475
```

<210> SEQ ID NO 8
<211> LENGTH: 249
<212> TYPE: PRT
<213> ORGANISM: Homo sapiens

<400> SEQUENCE: 8

```
Ser Gly Ile Ser Leu Asp Asn Ser Tyr Lys Met Asp Tyr Pro Glu Met
  1               5                  10                  15
Gly Leu Cys Ile Ile Asn Asn Lys Asn Phe His Lys Ser Thr Gly
                20                  25                  30
Met Thr Ser Arg Ser Gly Thr Asp Val Asp Ala Ala Asn Leu Arg Glu
             35                  40                  45
Thr Phe Arg Asn Leu Lys Tyr Glu Val Arg Asn Lys Asn Asp Leu Thr
     50                  55                  60
Arg Glu Glu Ile Val Glu Leu Met Arg Asp Val Ser Lys Glu Asp His
 65                  70                  75                  80
Ser Lys Arg Ser Ser Phe Val Cys Val Leu Leu Ser His Gly Glu Glu
                 85                  90                  95
Gly Ile Ile Phe Gly Thr Asn Gly Pro Val Asp Leu Lys Lys Ile Thr
            100                 105                 110
Asn Phe Phe Arg Gly Asp Arg Cys Arg Ser Leu Thr Gly Lys Pro Lys
        115                 120                 125
Leu Phe Ile Ile Gln Ala Cys Arg Gly Thr Glu Leu Asp Cys Gly Ile
130                 135                 140
Glu Thr Asp Ser Gly Val Asp Asp Asp Met Ala Cys His Lys Ile Pro
145                 150                 155                 160
Val Asp Ala Asp Phe Leu Tyr Ala Tyr Ser Thr Ala Pro Gly Tyr Tyr
                165                 170                 175
Ser Trp Arg Asn Ser Lys Asp Gly Ser Trp Phe Ile Gln Ser Leu Cys
            180                 185                 190
Ala Met Leu Lys Gln Tyr Ala Asp Lys Leu Glu Phe Met His Ile Leu
        195                 200                 205
Thr Arg Val Asn Arg Lys Val Ala Thr Glu Phe Glu Ser Phe Ser Phe
    210                 215                 220
Asp Ala Thr Phe His Ala Lys Lys Gln Ile Pro Cys Ile Val Ser Met
225                 230                 235                 240
Leu Thr Lys Glu Leu Tyr Phe Tyr His
                245
```

<210> SEQ ID NO 9
<211> LENGTH: 300
<212> TYPE: PRT
<213> ORGANISM: Homo sapiens

<400> SEQUENCE: 9

```
Gln Gly Val Leu Ser Ser Phe Pro Ala Pro Gln Ala Val Gln Asp Asn
  1               5                  10                  15
Pro Ala Met Pro Thr Ser Ser Gly Ser Glu Gly Asn Val Lys Leu Cys
                20                  25                  30
```

```
Ser Leu Glu Glu Ala Gln Arg Ile Trp Lys Gln Lys Ser Ala Glu Ile
         35                  40                  45

Tyr Pro Ile Met Asp Lys Ser Ser Arg Thr Arg Leu Ala Leu Ile Ile
     50                  55                  60

Cys Asn Glu Glu Phe Asp Ser Ile Pro Arg Arg Thr Gly Ala Glu Val
 65                  70                  75                  80

Asp Ile Thr Gly Met Thr Met Leu Leu Gln Asn Leu Gly Tyr Ser Val
                 85                  90                  95

Asp Val Lys Lys Asn Leu Thr Ala Ser Asp Met Thr Thr Glu Leu Glu
            100                 105                 110

Ala Phe Ala His Arg Pro Glu His Lys Thr Ser Asp Ser Thr Phe Leu
            115                 120                 125

Val Phe Met Ser His Gly Ile Arg Glu Gly Ile Cys Gly Lys Lys His
        130                 135                 140

Ser Glu Gln Val Pro Asp Ile Leu Gln Leu Asn Ala Ile Phe Asn Met
145                 150                 155                 160

Leu Asn Thr Lys Asn Cys Pro Ser Leu Lys Asp Lys Pro Lys Val Ile
                165                 170                 175

Ile Ile Gln Ala Cys Arg Gly Asp Ser Pro Gly Val Val Trp Phe Lys
            180                 185                 190

Asp Ser Val Gly Val Ser Gly Asn Leu Ser Leu Pro Thr Thr Glu Glu
        195                 200                 205

Phe Glu Asp Asp Ala Ile Lys Lys Ala His Ile Glu Lys Asp Phe Ile
    210                 215                 220

Ala Phe Cys Ser Ser Thr Pro Asp Asn Val Ser Trp Arg His Pro Thr
225                 230                 235                 240

Met Gly Ser Val Phe Ile Gly Arg Leu Ile Glu His Met Gln Glu Tyr
                245                 250                 255

Ala Cys Ser Cys Asp Val Glu Glu Ile Phe Arg Lys Val Arg Phe Ser
            260                 265                 270

Phe Glu Gln Pro Asp Gly Arg Ala Gln Met Pro Thr Thr Glu Arg Val
        275                 280                 285

Thr Leu Thr Arg Cys Phe Tyr Leu Phe Pro Gly His
    290                 295                 300

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence:fluorogenic
      substrate
<220> FEATURE:
<223> OTHER INFORMATION: Asp at position 1 is modified with an acetyl
      group; Asp at position 4 is modified with an
      a-(4-methyl-coumaryl-7-amide) group

<400> SEQUENCE: 10

Asp Glu Val Asp
  1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: PCR primer
<220> FEATURE:
<223> OTHER INFORMATION: Tyr at position 1 is modified with an acetyl
      group; Asp at position 4 may be modified with a
```

```
            CH2OC(O)-[2,6(CF3)2] Ph  group or an
            a-(4-methyl-coumaryl-7-amide) group.

<400> SEQUENCE: 11

Tyr Val Ala Asp
  1

<210> SEQ ID NO 12
<211> LENGTH: 37
<212> TYPE: DNA
<213> ORGANISM: Artificial Sequence
<220> FEATURE:
<223> OTHER INFORMATION: Description of Artificial Sequence: PCR primer

<400> SEQUENCE: 12
gactcgagtc tagagtcgac ttttttttttt tttttt                              37

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: PCR primer

<400> SEQUENCE: 13
aagtgagcag atcagaattg ag                                              22

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 14
gactcgagtc tagagtcgac                                                 20

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: PCR primer

<400> SEQUENCE: 15
gaggatcccc aaatgcaaac tggatgatga c                                    31

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: PCR primer

<400> SEQUENCE: 16
gccaccagct aaaaacattc tcaa                                            24

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: PCR primer

<400> SEQUENCE: 17
ttggatccag atggacttca gcagaaatct t                                    31
```

-continued

```
<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: PCR primer

<400> SEQUENCE: 18
attctcaaac cctgcatcca agtg                                          24

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: PCR primer

<400> SEQUENCE: 19
ggcttctcgt ggttcccaga gc                                            22

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 20
tgctcttcct gtgtagagat g                                             21
```

CASH (CASPASE HOMOLOGUE) WITH DEATH EFFECTOR DOMAIN, MODULATORS OF THE FUNCTION OF FAS

CROSS REFERENCE TO RELATED APPLICATION

The present application is a division of application Ser. No. 10/849,901, filed May 21, 2004, now abandoned which is a continuation of application Ser. No. 09/380,546, filed Nov. 29, 1999, now abandoned which is the national stage under 35 U.S.C. 371 of PCT/IL98/00098, filed Feb. 26, 1998, which claims priority from IL 120367/1997, filed Mar. 3, 1997 and IL 120759/1997, filed May 1, 1997. The entire contents of prior applications Ser. Nos. 10/849,901, 09/380,546 and PCT/IL98/00098 are herein incorporated by reference.

FIELD OF THE INVENTION

The present invention is generally in the field of receptors belonging to the TNF/NGF superfamily of receptors and the control of their biological functions. The TNF/NGF superfamily of receptors includes receptors such as the p55 and p75 tumor necrosis factor receptors (TNF-Rs, also called CD120a and CD120b, respectively, but hereinafter will be called p55-R and p75-R) and the FAS ligand receptor (also called FAS/APO1 or FAS-R or CD95, but hereinafter will be called FAS-R) and others. More specifically, the present invention further concerns novel proteins which bind to other proteins which themselves bind to the protein MORT-1 (or FADD), these also called MORT-1-binding proteins, or, which may also bind MORT-1 directly, and more specifically, it relates to one such protein, herein designated G1, (which has now also been designated 'CASH' for 'CASPASE HOMOLOG', but which will be called 'G1' herein throughout), which binds to the MORT-1-binding protein Mch4 (also designated/called CASP-10), and possibly also to another MORT-1-binding protein called MACH (also designated/called CASP-8), and possibly also directly to MORT-1 itself.

Accordingly, the present invention concerns, in general, new proteins which are capable of modulating or mediating the function of MORT-1 directly or indirectly or of other proteins which bind to MORT-1 directly or indirectly. In particular, the present invention concerns G1, its preparation and uses thereof, as well as the various novel isoforms of G1, their preparation and uses.

BACKGROUND OF THE RELATED ART

Tumor Necrosis Factor (TNF-α) and Lymphotoxin (TNF-β) (hereinafter, TNF, refers to both TNF-α and TNF-β) are multifunctional pro-inflammatory cytokines formed mainly by mononuclear phagocytes, which have many effects on cells (Wallach, D. (1986) In: *Interferon* 7 (Ion Gresser, ed.), pp. 83-122, Academic Press, London; and Beutler and Cerami (1987)). Both TNF-a and TNF-β initiate their effects by binding to specific cell surface receptors. Some of the effects are likely to be beneficial to the organism: they may destroy, for example, tumor cells or virus infected cells and augment antibacterial activities of granulocytes. In this way, TNF contributes to the defense of the organism against tumors and infectious agents and contributes to the recovery from injury. Thus, TNF can be used as an anti-tumor agent in which application it binds to its receptors on the surface of tumor cells and thereby initiates the events leading to the death of the tumor cells. TNF can also be used as an anti-infectious agent.

However, both TNF-α and TNF-β also have deleterious effects. There is evidence that overproduction of TNF-α can play a major pathogenic role in several diseases. For example, effects of TNF-α, primarily on the vasculature, are known to be a major cause for symptoms of septic shock (Tracey et al., 1986). In some diseases, TNF may cause excessive loss of weight (cachexia) by suppressing activities of adipocytes and by causing anorexia, and TNF-α was thus called cachetin. It was also described as a mediator of the damage to tissues in rheumatic diseases (Beutler and Cerami, 1987) and as a major mediator of the damage observed in graft-versus-host reactions (Piquet et al., 1987). In addition, TNF is known to be involved in the process of inflammation and in many other diseases.

Two distinct, independently expressed, receptors, the p55 and p75 TNF-Rs, which bind both TNF-α and TNF-β specifically, initiate and/or mediate the above noted biological effects of TNF. These two receptors have structurally dissimilar intracellular domains suggesting that they signal differently (See Hohmann et al., 1989; Engelmann et al., 1990; Brockhaus et al., 1990; Leotscher et al., 1990; Schall et al., 1990; Nophar et al., 1990; Smith et al., 1990; and Heller et al., 1990). However, the cellular mechanisms, for example, the various proteins and possibly other factors, which are involved in the intracellular signaling of the p55 an p75 TNF-Rs have yet to be elucidated. It is this intracellular signaling, which occurs usually after the binding of the ligand, i.e., TNF (α or β), to the receptor, that is responsible for the commencement of the cascade of reactions that ultimately result in the observed response of the cell to TNF.

As regards the above-mentioned cytocidal effect of TNF, in most cells studied so far, this effect is triggered mainly by the p55 TNF-R. Antibodies against the extracellular domain (ligand binding domain) of the p55 TNF-R can themselves trigger the cytocidal effect (see EP 412486) which correlates with the effectivity of receptor cross-linking by the antibodies, believed to be the first step in the generation of the intracellular signaling process. Further, mutational studies (Brakebusch et al., 1992; Tartaglia et al., 1993) have shown that the biological function of the p55 TNF-R depends on the integrity of its intracellular domain, and accordingly it has been suggested that the initiation of intracellular signaling leading to the cytocidal effect of TNF occurs as a consequence of the association of two or more intracellular domains of the p55 TNF-R. Moreover, TNF (α and β) occurs as a homotrimer, and as such, has been suggested to induce intracellular signaling via the p55 TNF-R by way of its ability to bind to and to cross-link the receptor molecules, i.e., cause receptor aggregation.

Another member of the TNF/NGF superfamily of receptors is the FAS receptor (FAS-R) which has also been called the FAS antigen, a cell-surface protein expressed in various tissues and sharing homology with a number of cell-surface receptors including TNF-R and NGF-R. The FAS-R mediates cell death in the form of apoptosis (Itoh et al., 1991), and appears to serve as a negative selector of autoreactive T cells, i.e., during maturation of T cells, FAS-R mediates the apoptopic death of T cells recognizing self-antigens. It has also been found that mutations in the FAS-R gene (lpr) cause a lymphoproliferation disorder in mice that resembles the human autoimmune disease systemic lupus erythematosus (SLE) (Watanabe-Fukunaga et al., 1992). The ligand for the FAS-R appears to be a cell-surface associated molecule carried by, amongst others, killer T cells (or cytotoxic T lymphocytes—CTLs), and hence when such CTLs contact cells carrying FAS-R, they are capable of inducing apoptopic cell death of the FAS-R-carrying cells. Further, a monoclonal antibody has been prepared that is specific for FAS-R, this monoclonal antibody being capable of inducing apoptopic cell death in cells carrying FAS-R, including mouse cells transformed by cDNA encoding human FAS-R (Itoh et al., 1991).

While some of the cytotoxic effects of lymphocytes are mediated by interaction of a lymphocyte-produced ligand with the widely occurring cell surface receptor FAS-R (CD95), which has the ability to trigger cell death, it has also been found that various other normal cells, besides T lymphocytes, express the FAS-R on their surface and can be killed by the triggering of this receptor. Uncontrolled induction of such a killing process is suspected to contribute to tissue damage in certain diseases, for example, the destruction of liver cells in acute hepatitis. Accordingly, finding ways to restrain the cytotoxic activity of FAS-R may have therapeutic potential.

Conversely, since it has also been found that certain malignant cells and HIV-infected cells carry the FAS-R on their surface, antibodies against FAS-R, or the FAS-R ligand, may be used to trigger the FAS-R mediated cytotoxic effects in these cells and thereby provide a means for combating such malignant cells or HIV-infected cells (see Itoh et al., 1991). Finding yet other ways for enhancing the cytotoxic activity of FAS-R may therefore also have therapeutic potential.

It has been a long felt need to provide a way for modulating the cellular response to TNF ($\alpha$ or $\beta$) and FAS-R ligand. For example, in the pathological situations mentioned above, where TNF or FAS-R ligand is overexpressed, it is desirable to inhibit the TNF- or FAS-R ligand-induced cytocidal effects, while in other situations, e.g., wound healing applications, it is desirable to enhance the TNF effect, or in the case of FAS-R, in tumor cells or HIV-infected cells, it is desirable to enhance the FAS-R mediated effect.

A number of approaches have been made by the applicants (see for example, European Application Nos. EP 186833, EP 308378, EP 398327 and EP 412486) to regulate the deleterious effects of TNF by inhibiting the binding of TNF to its receptors using anti-TNF antibodies or by using soluble TNF receptors (being essentially the soluble extracellular domains of the receptors) to compete with the binding of TNF to the cell surface-bound TNF-Rs. Further, on the basis that TNF-binding to its receptors is required for the TNF-induced cellular effects, approaches by applicants (see for example EPO 568925) have been made to modulate the TNF effect by modulating the activity of the TNF-Rs.

Briefly, EPO 568925 relates to a method of modulating signal transduction and/or cleavage in TNF-Rs whereby peptides or other molecules may interact either with the receptor itself or with effector proteins interacting with the receptor, thus modulating the normal function of the TNF-Rs. In EPO 568925, there is described the construction and characterization of various mutant p55 TNF-Rs, having mutations in the extracellular, transmembrane, and intracellular domains of the p55 TNF-R. In this way, regions within the above domains of the p55 TNF-R were identified as being essential to the functioning of the receptor, i.e., the binding of the ligand (TNF) and the subsequent signal transduction and intracellular signaling which ultimately results in the observed TNF-effect on the cells. Further, there is also described a number of approaches to isolate and identify proteins, peptides or other factors which are capable of binding to the various regions in the above domains of the TNF-R, which proteins, peptides and other factors may be involved in regulating or modulating the activity of the TNF-R. A number of approaches for isolating and cloning the DNA sequences encoding such proteins and peptides; for constructing expression vectors for the production of these proteins and peptides; and for the preparation of antibodies or fragments thereof which interact with the TNF-R or with the above proteins and peptides that bind various regions of the TNF-R, are also set forth in EPO 568925. However, EPO 568925 does not specify the actual proteins and peptides which bind to the intracellular domains of the TNF-Rs (e.g., p55 TNF-R), nor does it describe the yeast two-hybrid approach to isolate and identify such proteins or peptides which bind to the intracellular domains of TNF-Rs. Similarly, in EPO 568925 there is no disclosure of proteins or peptides capable of binding the intracellular domain of FAS-R.

Thus, when it is desired to inhibit the effect of TNF, or the FAS-R ligand, it would be desirable to decrease the amount or the activity of TNF-Rs or FAS-R at the cell surface, while an increase in the amount or the activity of TNF-Rs or FAS-R would be desired when an enhanced TNF or FAS-R ligand effect is sought. To this end the promoters of both the p55 TNF-R and the p75 TNF-R have been sequenced, analyzed and a number of key sequence motifs have been found that are specific to various transcription regulating factors, and as such the expression of these TNF-Rs can be controlled at their promoter level, i.e., inhibition of transcription from the promoters for a decrease in the number of receptors, and an enhancement of transcription from the promoters for an increase in the number of receptors (EP 606869 and WO 9531206). Corresponding studies concerning the control of FAS-R at the level of the promoter of the FAS-R gene have yet to be reported.

While it is known that the tumor necrosis factor (TNF) receptors, and the structurally-related receptor FAS-R, trigger in cells, upon stimulation by leukocyte-produced ligands, destructive activities that lead to their own demise, the mechanisms of this triggering are still little understood. Mutational studies indicate that in FAS-R and the p55 TNF receptor (p55-R) signaling for cytotoxicity involve distinct regions within their intracellular domains (Brakebusch et al., 1992; Tartaglia et al., 1993; Itoh and Nagata, 1993). These regions (the 'death domains' or 'death effector domains' called 'DED') have sequence similarity. The 'death domains' of both FAS-R and p55-R tend to self-associate. Their self-association apparently promotes that receptor aggregation which is necessary for initiation of signaling (see Song et al., 1994; Wallach et al., 1994; Boldin et al., 1995), and at high levels of receptor expression can result in triggering of ligand-independent signaling (Boldin et al., 1995).

Some of the cytotoxic effects of lymphocytes are mediated by interaction of a lymphocyte-produced ligand with FAS-R (CD-95), a widely occurring cell surface receptor which has the ability to trigger cell death (see also Nagata and Golstein, 1995); and that cell killing by mononuclear phagocytes involves a ligand-receptor couple, TNF and its receptor p55-R (CD120), that is structurally related to FAS-R and its ligand (see also Vandenabeele et al., 1995). Like other receptor-induced effects, cell death induction by the TNF receptors and FAS-R occurs via a series of protein-protein interactions, leading from ligand-receptor binding to the eventual activation of enzymatic effector functions, which in the case studies have elucidated non-enzymatic protein-protein interactions that intiate signaling for cell death:binding of trimeric TNF or the FAS-R ligand molecules to the receptors, the resulting interactions of their intracellular domains (Brakebusch et al., 1992; Tartaglia et al., 1993; Itoh and Nagata, 1993) augmented by a propensity of the death-domain motifs (or death effector domains, DED) to self-associate (Boldin et al., 1995a), and induced binding of two cytoplasmic proteins (which can also bind to each other) to the receptors' intracellular domains—MORT-1 (or FADD) to FAS-R (Boldin et al., 1995b; Chinnaiyan et al., 1995; Kischkel et al., 1995) and TRADD to p55-R (Hsu et al., 1995; Hsu et al., 1996). Three proteins that bind to the intracellular domain of FAS-R and p55-R at the 'death domain' region involved in cell-death induction by the receptors through hetero-association of homologous regions and that independently are also capable of triggering cell death were identified by the yeast two-hybrid screening procedure. One of these is the protein, MORT-1 (Boldin et al. 1995b), also known as FADD (Chinnaiyan et al., 1995) that binds specifically to FAS-R. The second one, TRADD (see also Hsu et al., 1995, 1996), binds to p55-R, and the third, RIP (see also Stanger et al., 1995), binds to both FAS-R and p55-R. Besides their binding to FAS-R and p55-R, these proteins are also capable of binding to each other, which provides for a functional "cross-talk" between FAS-R and p55-R. These bindings occur through a conserved sequence motif, the 'death domain module' (also called 'DED' for 'Death Effector Domain') common to the receptors and their associated proteins. Furthermore, although in the yeast two-hybrid test MORT-1 was shown to bind spontaneously to FAS-R, in mammalian cells, this binding takes place only after stimulation of the receptor, suggesting that MORT-1 participates in the initiating events of FAS-R signaling. MORT-1 does not contain any sequence motif characteristic of enzymatic activity, and therefore, its ability to trigger cell death seems not to involve an intrinsic activity of MORT-1 itself, but rather, activation of some other protein(s) that bind MORT-1 and act further downstream in the signaling cascade. Cellular expression of MORT-1 mutants lacking the N-terminal part of the molecule has been shown to block cytotoxicity induction by FAS/APO1 (FAS-R) or p55-R (Hsu et al., 1996; Chinnaiyan et al., 1996), indicating that this N-terminal region transmits the signaling for the cytocidal effect of both receptors through protein-protein interactions.

Recent studies have implicated a group of cytoplasmic thiol proteases which are structurally related to the *Caenorhabditis elegans* protease CED3 and to the mammalian interleukin-1β converting enzyme (ICE) in the onset of various physiological cell death processes (reviewed in Kumar, 1995 and Henkart, 1996). There have also been some indications that protease(s) of this family may take part in the cell-cytotoxicity induced by FAS-R and TNF-Rs. Specific peptide inhibitors of the proteases and two virus-encoded proteins that block their function, the cowpox protein crmA and the Baculovirus p35 protein, were found to provide protection to cells against this cell-cytotoxicity (Enari et al., 1995; Los et al., 1995; Tewari et al., 1995; Xue et al., 1995; Beidler et al., 1995). Rapid cleavage of certain specific cellular proteins, apparently mediated by protease(s) of the CED3/ICE family, could be demonstrated in cells shortly after stimulation of FAS-R or TNF-Rs.

It should be noted that these CED3/ICE proteases, also called caspases, are produced as inactive precursors and become activated by proteolytic processing upon death induction. These caspases are conserved cysteine proteases that cleave specific cellular proteins downstream of aspartate residues thereby playing a critical role in all known programmed cell death processes. In addition to their homologous C-terminal region from which the mature proteases are derived, the precursor proteins contain unique N-terminal regions. Interactions of these 'prodomains' with specific regulatory molecules allow differential activation of the various caspases by different death-inducing signals (Boldin et al., 1996; Muzio et al., 1996; Duan and Dixit, 1997; Van Criekinge et al., 1996; Ahmad et al., 1997).

One such protease and various isoforms thereof (including inhibitory ones), designated MACH (also called CASP-8) which is a MORT-1 binding protein and which serves to modulate the activity of MORT-1 and hence of FAS-R and p55-R, and which may also act independently of MORT-1, has been recently isolated, cloned, characterized, and its possible uses also described, as is set forth in detail and incorporated herein in their entirety by reference, in co-owned, copending Israel Patent Application Nos. IL 114615, 114986, 115319, 116588 and 117932, as well as their corresponding PCT counterpart No. PCT/US96/10521, and in a recent publication of the present inventors (Boldin et al., 1996). Another such protease and various isoforms thereof (including inhibitory ones), designated Mch4 (also called CASP-10) has also recently been isolated and characterized by the present inventors (unpublished) and others (Fernandes-Alnemri et al., 1996; Srinivasula et al., 1996). This Mch4 protein is also a MORT-1 binding protein which serves to modulate the activity of MORT-1 and hence likely also of FAS-R and p55-R, and which may also act independently of MORT-1. Thus, details concerning all aspects, features, characteristics and uses of Mch4 are set forth in the above noted publications, all of which are incorporated herein in their entirety by reference.

It should also be noted that the caspases, MACH (CASP-8) and Mch4 (CASP-10), which have similar prodomains (see Boldin et al., 1996; Muzio et al., 1996; Fernandes-Alnemri et al., 1996; Vincent and Dixit, 1997) interact through their prodomains with MORT-1, this interaction being via the 'death domain motif' or 'death effector domain', DED, present in the N-terminal part of MORT-1 and present in duplicate in MACH (CASP-8) and Mch4 (CASP-10) (see Boldin et al., 1995b; Chinnalyan et al., 1995).

It should also be mentioned, in view of the above, that the various proteins/enzymes/receptors involved in the intracellular signaling processes leading to cell death, have been given a variety of names. In order to precent confusion, the following is a list of the various names, including new names decided upon by a new convention, of each of these proteins, or parts thereof, and the names which are used herein throughout for convenience:

| Common or first name | Other names | New Convention name | Name used herein |
|---|---|---|---|
| p55 TNF receptor | p55-R | CD120a | p55-R |
| p75 TNF receptor | p75-R | CD120b | p75-R |
| FAS receptor | FAS-R, FAS/APO1 | CD95 | FAS-R |
| MORT-1 | FADD | — | MORT-1 |
| MACH | FLICE1, Mch5 | CASP-8 | MACH |
| Mch4 | FLICE2 | CASP-10 | Mch4 |
| G1 | — | CASH | G1 |

-continued

| Common or first name | Other names | New Convention name | Name used herein |
|---|---|---|---|
| 'death domain' | death domain motif, MORT motif, death effector domain (DED), MORT modules | — | death domain/death domain motif/ MORT modules |
| CED3/ICE proteases | caspases | CASP | CED3/ICE proteases |

SUMMARY OF THE INVENTION

It is an object of the invention to provide novel proteins, including all isoforms, analogs, fragments or derivatives thereof, which are capable of binding to MORT-1-binding proteins such as, for example, the above noted Mch4 and MACH proteins and their isoforms, or which are capable of binding to MORT-1 itself. As MORT-1 itself binds to the intracellular domain of the FAS-R, the novel proteins of the present invention by binding to the MORT-1-binding proteins and hence indirectly to MORT-1, or by binding directly to the MORT-1 protein are therefore capable of affecting the intracellular signaling process initiated by the binding of the FAS ligand to its receptor, and as such the new proteins of the present invention are modulators of the FAS-R-mediated effect on cells. MORT-1 is also involved in the modulation of the TNF effect on cells via its involvement in the modulation of p55-R and hence the new proteins of the present invention are also conceived as modulators of the TNF-effect, mediated by the p55-R, on cells. Likewise, by analogy to the above modulation of the FAS-R and p55-R mediated effect on cells, the proteins of the present invention may also be mediators or modulators of other cytotoxic mediators or inducers by way of operating via common or related intracellular signaling pathways in which the proteins (e.g. G1 and its isoforms) of the invention are involved. These novel proteins of the present invention are designated "G1" proteins, and as noted above include the G1 protein (exemplified hereinbelow), all its isoforms, analogs, fragments or derivatives thereof.

Another object of the invention is to provide antagonists (e.g., antibodies, peptides, organic compounds, or even some isoforms) to the above novel G1 proteins, isoforms, analogs, fragments and derivatives thereof, which may be used to inhibit the signaling process, or, more specifically, the cell-cytotoxicity, when desired.

A further object of the invention is to use the above novel G1 proteins, isoforms, analogs, fragments and derivatives thereof, to isolate and characterize additional proteins or factors, which may be involved in regulation of receptor activity, e.g., other proteases which cleave the novel proteins to render then biologically active, and/or to isolate and identify other receptors further upstream in the signaling process to which these novel proteins, analogs, fragments and derivatives bind (e.g., other FAS-Rs or related receptors), and hence, in whose function they are also involved.

A still further object of the invention is to provide inhibitors which can be introduced into cells to bind or interact with the G1 protein and possible G1 isoforms having protease activity (the G1 protein has a region that is homologous to the proteolytic regions of Mch4 and MACH) and inhibit their intracellular activity which, at least for some possible G1 isoforms, may be a proteolytic activity.

Moreover, it is an object of the present invention to use the above-mentioned novel G1 proteins, isoforms and analogs, fragments and derivatives thereof as antigens for the preparation of polyclonal and/or monoclonal antibodies thereto.

The antibodies, in turn, may be used, for example, for the purification of the new proteins from different sources, such as cell extracts or transformed cell lines.

Furthermore, these antibodies may be used for diagnostic purposes, e.g., for identifying disorders related to abnormal functioning of cellular effects mediated by the FAS-R or other related receptors.

A further object of the invention is to provide pharmaceutical compositions comprising the above novel G1 proteins, isoforms, or analogs, fragments or derivatives thereof, as well as pharmaceutical compositions comprising the above noted antibodies or other antagonists.

In accordance with the present invention, a novel protein, G1, which is capable of binding to or, or interacting with, Mch4, which itself binds to MORT-1, which binds to the intracellular domain of the FAS-R, was isolated. G1 also may interact with another MORT-1-binding protein called MACH, and may also be capable of binding or interacting directly with MORT-1. G1 probably functions as a modulator component of the cell-death pathway initiated by the binding of FAS ligand to FAS-R at the cell surface, and this by virtue of the fact that it has a proteolytic region similar to the proteolytic regions of Mch4 and MACH, and hence G1 may also be an active intracellular protease. Further, depending on the transcription/translation processes in the expression of G1, especially its proteolytic region, some isoforms of G1 may be expressed without an active proteolytic region and as such may serve as antagonists of proteolytic activity mediated by, for example, Mch4 and MACH. Proteases of the CED3/ICE family have been implicated in the apoptopic processes triggered by FAS-R. MORT-1 (or FADD) binds to the intracellular domain of FAS-R upon activation of this receptor and the novel G1 protein of the present invention binds to MORT-1-binding proteins such as Mch4 and possibly also MACH or possibly directly to MORT-1. The G1 protein, cloned and characterized in accordance with the present invention, may exist in multiple isoforms, some of which isoforms have a CED3/ICE homology region which has proteolytic activity (proteolytic domain), similar to those of Mch4 and some isoforms of MACH, and which may cause the death of cells when expressed in the cells. Thus, activation of this novel CED3/ICE homolog (i.e., the various G1 isoforms having the proteolytic domain) by FAS-R (via direct or indirect MORT-1 interaction) appears to constitute an effector component of the FAS-R-mediated cell-death pathway.

Moreover, G1 also appears to function as an effector component of the cell-death pathway initiated by the binding of TNF to p55-R at the cell surface, this by way of indirect mechanism of MORT-1 binding to TRADD, a protein which binds to the intracellular domain of p55-R (Hsu et al., 1995), followed by or together with G1 binding to MORT-1-binding proteins such as, for example, Mch4 or MACH, or binding to MORT-1 directly, with the activation of G1 into an active protease involved in effecting cell death.

It should also be noted that while G1 displays at least some of the sequence features critical of the function of the CED3/

ICE proteases, it does, however, have some distinctive sequence features of its own which may endow it with a unique and possibly tissue/cell specific mode of action.

Thus, in accordance with the present invention, a new protein designated G1 is provided. This G1 protein was isolated and cloned by the two-hybrid screening assay and characterized as a molecule which binds Mch4. Mch4, as noted above, is a MORT-1-binding protein which is capable of effecting cell death, although however, it should also be noted that some isoforms of Mch4 have the opposite effect, namely, they inhibit the killing of cells. Further, the sequencing of G1 has so far revealed that it has in its N-terminal region two so-called 'MORT MODULES' (MM) which are also found in the MORT-1-binding proteins MACH and Mch4. These MORT MODULES in G1 appear to account for its ability to bind to Mch4, and may also be the basis for its possible binding to MORT-1 directly and for its binding to MACH or to specific MACH isoforms (specific splice variants of MACH). In the G1 sequence downstream of the N-terminus region containing the MORT MODULES there also appears to be a long region displaying similarity to proteolytic region of MACH and Mch4. Moreover, from an initial analysis of the possible location of the G1 sequence in the human chromosomes, it appears that G1 is located on chromosome No. 2 very close to the positions of Mch4 and MACH which is also indicative of a relationship between G1, MACH and Mch4.

More specifically, at least three possible isoforms of G1 have been found in accordance with the present invention (see Example 1 below). Two of these have been isolated and cloned and appear to represent two splice variants of a novel protein, designated G1 (or CASH). These two isoforms are called G1α (or CASHα) for the larger isoform and G1β (or CASHβ) for the shorter isoform (although there appears to be more than one short isoform, hence G1β is also designated G1β1, and the other short isoform is designated G1β2—see Example 1 below). These G1α and β isoforms each contain two N-terminal death domain motifs/MORT MODULES and can bind to each other via these death domain motifs, and can also bind to MORT1, MACH and Mch4 via these death domain motifs. The longer G1α isoform has a unique C-terminal portion (in comparison to the shorter G1β isoform) this unique C-terminal portion having sequence homology to the caspase protease activity region. With respect to biological activity, the shorter G1β isoform inhibits cell death/cytotoxicity mediated by p55-R and FAS-R, while, in contrast, the longer G1α isoform has a cytotoxic effect on at least some types of cells (e.g. 293 cells) which cytotoxicity involved its protease-homology region. However, it should also be noted that the longer G1α isoform is also capable of inhibiting cytotoxicity mediated by FAS-R and p55-R in other types of cells (e.g. HeLa cells). These results indicate that G1 (namely, its various isoforms) acts as an attenuator/inhibitor and/or an initiator/enhancer of p55-R- and FAS-R-mediated signaling for cell death.

It should also be noted that for the sake of clarity the various isoforms of G1, for example G1α and G1β, will often be referred to herein as simply 'G1', but it is to be understood that in these cases all the isoforms of G1 are to be included in the meaning of 'G1' so that this could mean both inducers/enhancers of cell cytotoxicity as well as inhibitors/attenuators of cell cytotoxicity. When a specific G1 isoform is intended, then it will be named specifically, e.g. G1α or G1β, as the case may be). As such 'G1' when used collectively to refer to the various isoforms will also often be referred to herein as a 'modulator', this meaning that it can be inhibitory or augmentory to the biological activity in question.

In view of the above-mentioned, it therefore arises, as noted above and as set forth hereinbelow, that G1 is apparently a modulator of MORT-1 activity and hence a modulator of the cellular effects mediated by the FAS-R and also the p55-R as well as possibly other receptors of the TNF/NGF receptor family and others as well which may share common intracellular signaling components and mechanisms.

Thus, as G1 apparently has a protease-like region (at least the long isoform) it may be responsible directly for cell cytotoxicity and inflammation caused or induced by various stimuli including those transmitted via receptors of the TNF/NGF receptor family and possibly others as well.

G1 may also serve as an inhibitor of cell cytotoxicity and inflammation by virtue of its being present as part of a complex of other proteins and as such may effect the cytotoxicity or inflammatory effects of these other proteins (e.g. MACH and Mch4 or even MORT-1), ultimately resulting in an inhibition of their cytotoxic activity or their activity in inflammation.

G1 may yet also serve as an enhancer or augmentor of cell cytotoxicity and inflammation and this by augmenting the activity of other proteins (e.g. Mch4 and MACH or even MORT-1) by binding to them and recruiting them to bind MORT-1 or to act independently of MORT-1, in either case the recruitment serving to augment the cytotoxic activity of the various proteins or to augment their inflammatory effects.

Likewise, in an analogous fashion G1 may also serve as an inhibitor or an augmentor of other intracellular mediators or modulators having pathways in which G1 is actively involved.

MORT-1 (for 'Mediator of Receptor Toxicity', Boldin et al., 1995b), is capable of binding to the intracellular domain of the FAS-R. This FAS-binding protein appears to act as a mediator or modulator of the FAS-R ligand effect oncells by way of mediating or modulating the intracellular signaling process which usually occurs following the binding of the FAS-R ligand at the cell surface. In addition to its FAS-binding specificity, MORT-1 was shown to have other characteristics (see Reference Example 1), for example, it has a region homologous to the "death domain" (DD) regions of the p55-TNF-R and FAS-R (p55-DD and FAS-DD), and thereby is also capable of self-association. MORT-1 is also capable of activating cell cytotoxicity on its own, an activity possibly related to its self-association capability. It has also been found that co-expression of the region in MORT-1 that contains the "death domain" homology sequence (MORT-DD, present in the C-terminal part of MORT-1) strongly interferes with FAS-induced cell death, as would be expected from its ability to bind to the "death domain" of the FAS-IC. Further, in the same experimental conditions, it was found that co-expression of the part of MORT-1 that does not contain the MORT-DD region (the N-terminal part of MORT-1, amino acids 1-117, "MORT-1 head") resulted in no interference of the FAS-induced cell death and, if at all, a somewhat enhanced FAS-induced cell cytotoxicity.

Accordingly, it is likely that MORT-1 also binds to other proteins involved in the intracellular signaling process. These MORT-1-binding proteins may therefore also act as indirect mediators or modulators of the FAS-R ligand effect on cells by way of mediating or modulating the activity of MORT-1; or these MORT-1-binding proteins may act directly as mediators or modulators of the MORT-1-associated intracellular signaling process by way of mediating or modulating the activity of MORT-1, which, as noted above, has an apparently independent ability to activate cell cytotoxicity. These MORT-1-binding proteins may also be used in any of the standard screening procedures to isolate, identify and characterize additional proteins, peptides, factors, antibodies, etc., which may be involved in the MORT-1-associated or FAS-R-associated signaling process or may be elements of other intracellular signaling processes. Such MORT-1-binding proteins have been isolated and have been described as noted above in the co-owned co-pending Israel application Nos. IL 114,615, 114,986, 115,319, 116,588, 117,932 and their corresponding PCT application PCT/US96/10521 (as regards MACH and its isoforms), and by others such as Fernandes-Alnemr et al. (1996) and Srinivasula et al. (1996) (as regards Mch4 and other such 'Mch' proteins). One of these MORT-1-binding proteins, and above noted MACH, was initially cloned, sequenced, and partially characterized as having the following properties : The MACH cDNA encodes the ORF-B open-reading frame; MACH binds to MORT-1 in a very strong and specific manner; the MACH binding site in MORT-1 occurs upstream of the MORT-1 "death domain" motif; the ORF-B region of MACH is the MORT-1-interacting part thereof; and MACH is capable of self-association and of inducing cell cytotoxicity on its own. Further, later analysis as set forth in the above co-owned, co-pending patent applications as well as Boldin et al. (1996) showed that MACH actually exists in a number of isoforms. Moreover, the MACH ORF-B noted above is in fact one of the MACH isoforms designated as MACHβ1. In the above publications concerning Mch4 it was also shown that this protein also binds MORT-1 (or FADD) and is directly involved in cell-cytotoxicity with MORT-1 or independent thereof and this by virtue of its proteolytic activity.

Accordingly, the present invention provides a DNA sequence encoding a G1 protein, analogs or fragments thereof, capable of binding to or interacting directly or indirectly with MORT-1 and/or any of the MORT-1-binding proteins, such as, for example, Mch4 or MACH, said G1 protein, analogs or fragments thereof being capable of mediating the intracellular effect mediated by the FAS-R or p55-TNF-R, said G1 protein, analogs or fragments thereof, also being capable of modulating or mediating the intracellular effect of other intracellular proteins to which it is capable of binding directly or indirectly.

In particular, the present invention provides a DNA sequence selected from the group consisting of:

(a) a cDNA sequence derived from the coding region of a native G1 protein;

(b) DNA sequences capable of hybridization to a sequence of (a) under moderately stringent conditions and which encode a biologically active G1 protein; and (c) DNA sequences which are degenerate as a result of the genetic code to the DNA sequences defined in (a) and (b) and which encode a biologically active G1 protein.

Another specific embodiment of the above DNA sequence of the invention is a DNA sequence comprising at least part of the sequence encoding at least one isoform of the G1 protein. Another embodiment of the above DNA sequence is the sequence encoding the G1 protein as depicted in FIG. 1, (the G1α isoform). Another such embodiment is a second G1 isoform depicted in FIG. 2 (the G1β isoform).

The present invention provides G1 proteins, and analogs, fragments or derivatives thereof encoded by any of the above sequences of the invention, said proteins, analogs, fragments and derivatives being capable of binding to or interacting directly or indirectly with MORT-1 and/or any of the MORT-1-binding proteins such as, for example, Mch4 or MACH, and mediating the intracellular effect mediated by the FAS-R or p55 TNF-R, or any other cytotoxic mediator of inducer to which said G1 proteins, analogs, fragments or derivatives are capable of binding directly or indirectly.

A specific embodiment of the invention is the G1 protein, analogs, fragments and derivatives thereof. Another embodiment is any isoform of the G1 protein, analogs, fragments and derivatives thereof.

Also provided by the present invention are vectors encoding the above G1 protein, and analogs, fragments or derivatives of the invention, which contain the above DNA sequence of the invention, these vectors being capable of being expressed in suitable eukaryotic or prokaryotic host cells; transformed eukaryotic or prokaryotic host cells containing such vectors; and a method for producing the G1 protein, or analogs, fragments or derivatives of the invention by growing such transformed host cells under conditions suitable for the expression of said protein, analogs, fragments or derivatives, effecting post-translational modifications of said protein as necessary for obtaining said protein and extracting said expressed protein, analogs, fragments or derivatives from the culture medium of said transformed cells or from cell extracts of said transformed cells. The above definitions are intended to include all isoforms of the G1 protein.

In another aspect, the present invention also provides antibodies or active derivatives or fragments thereof specific the G1 protein, and analogs, fragments and derivatives thereof, of the invention.

By yet another aspect of the invention, there are provided various uses of the above DNA sequences or the proteins which they encode, according to the invention, which uses include, in general, amongst others:

(A) A method for the modulation of cell death or inflammatory processes, comprising treating said cells with one or more G1 proteins, analogs, fragments or derivatives of the invention as noted above, wherein said treating of said cells comprises introducing into said cells said one or more proteins, analogs, fragments or derivatives in a form suitable for intracellular introduction thereof, or introducing into said cells a nucleotide sequence encoding said one or more proteins, analogs, fragments, or derivatives in the form of a suitable vector carrying said sequence, said vector capable of effecting the insertion of said sequence into said cells in a way that said sequence is expressed in said cells; and (B) A method for the modulation of cell death or inflammatory processes, comprising treating said cells with one or more inhibitors of one or more proteins/enzymes mediating said cell death or inflammatory processes, said inhibitors being selected from the group consisting of: (i) one or more G1 proteins, analogs, fragments or derivatives of the invention, capable of inhibiting said cell death or inflammatory processes; and (ii) inhibitors of one or more G1 proteins of the invention when said one or more G1 proteins augments/enhances or mediates said cell death or inflammatory processes.

More particularly, the above methods of the present invention include the following specific embodiments:

(i) A method for the modulation of the FAS-R ligand or TNF effect on cells carrying a FAS-R or p55-R, comprising treating said cells with one or more G1 proteins, analogs, fragments or derivatives of the invention, capable of binding to MORT-1, directly or indirectly or capable of binding to MORT-1 binding proteins such as Mch4 or MACH, which MORT-1, in turn, directly binds to the intracellular domain of FAS-R, or capable of binding directly or indirectly to MORT-1 or to MORT-1-binding proteins as noted above, which MORT-1, in turn, binds to TRADD which binds to the intracellular domain of p55-R, and thereby being capable of modulating/mediating the activity of said FAS-R or p55 TNF-R, wherein said treating of said cells comprises introducing into said cells said one or more proteins, analogs, fragments or derivatives in a form suitable for intracellular introduction thereof, or introducing into said cells a DNA sequence encoding said one or more proteins, analogs, fragments or derivatives in the form of a suitable vector carrying said sequence, said vector being capable of effecting the insertion of said sequence into said cells in a way that said sequence is expressed in said cells.

(ii) A method for the modulation of the FAS-R ligand or TNF effect on cells according to (i) above, wherein said treating of cells comprises introducing into said cells said G1 protein, or analogs, fragments or derivatives thereof, in a form suitable for intracellular introduction, or introducing into said cells a DNA sequence encoding said G1 protein, or analogs, fragments or derivatives in the form of a suitable vector carrying said sequence, said vector being capable of effecting the insertion of said sequence into said cells in a way that said sequence is expressed in said cells.

(iii) A method as in (ii) above wherein said treating of said cells is by transfection of said cells with a recombinant animal virus vector comprising the steps of:

(a) constructing a recombinant animal virus vector carrying a sequence encoding a viral surface protein (ligand) that is capable of binding to a specific cell surface receptor on the surface of a FAS-R- or p55-R-carrying cell and a second sequence encoding a protein selected from G1 protein, and analogs, fragments and derivatives thereof, that when expressed in said cells ia capable of modulating/mediating the activity of said FAS-R or p55-R; and (b) infecting said cells with said vector of (a).

(iv) A method for modulating the FAS-R ligand of TNF effect on cells carrying a FAS-R or a p55-R comprising treating said cells with antibodies or active fragments or derivatives thereof, according to the invention, said treating being by application of a suitable composition containing said antibodies, active fragments or derivatives thereof to said cells, wherein when at least part of the G1 protein is exposed on the extracellular surface, said composition is formulated for extracellular application, and when said G1 proteins are entirely intracellular, said composition is formulated for intracellular application.

(v) A method for modulating the FAS-R ligand or TNF effect on cells carrying a FAS-R or p55-R comprising treating said cells with an oligonucleotide sequence encoding an antisense sequence of at least part of the G1 protein sequence of the invention, said oligonucleotide sequence being capable of blocking the expression of the G1 protein.

(vi) A method as in (ii) above for treating tumor cells or HIV-infected cells or other diseased cells, comprising:

(a) constructing a recombinant animal virus vector carrying a sequence encoding a viral surface protein capable of binding to a specific tumor cell surface receptor or HIV-infected cell surface receptor or receptor carried by other diseased cells and a sequence encoding a protein selected from G1 protein, analogs, fragments and derivatives of the invention, that when expressed in said tumor, HIV-infected, or other diseased cell is capable of killing said cell; and (b) infecting said tumor or HIV-infected cells or other diseased cells with said vector of (a).

(vii) A method for modulating the FAS-R ligand or TNF effect on cells comprising applying the ribozyme procedure in which a vector encoding a ribozyme sequence capable of interacting with a cellular mRNA sequence encoding a G1 protein according to the invention, is introduced into said cells in a form that permits expression of said ribozyme sequence in said cells, and wherein when said ribozyme sequence is expressed in said cells it interacts with said cellular mRNA sequence and cleaves said mRNA sequence resulting in the inhibition of expression of said G1 protein in said cells.

(viii) A method selected from the method according to the invention, wherein said G1 protein encoding sequence comprises at least one of the G1 isoforms, analogs, fragments and derivatives of any thereof according to the invention which are capable of binding directly or indirectly to MORT-1 or MORT-1-binding proteins such as, for example, Mch4 and MACH, which MORT-1, in turn, binds specifically to FAS-IC, or which are capable of binding directly or indirectly to MORT-1 or the above MORT-1-binding proteins, which MORT-1, in turn, binds to TRADD and which in turn binds to the p55-IC.

(ix) A method for isolating and identifying proteins, according to the invention capable of binding directly or indirectly to the MORT-1 protein or the MORT-1-binding proteins, comprising applying the yeast two-hybrid procedure in which a sequence encoding said MORT-1 protein or MORT-1-binding proteins is carried by one hybrid vector and sequence from a cDNA or genomic DNA library is carried by the second hybrid vector, the vectors then being used to transform yeast host cells and the positive transformed cells being isolated, followed by extraction of the said second hybrid vector to obtain a sequence encoding a protein which binds to said MORT-1 protein or said MORT-1-binding proteins.

(x) A method according to any of the (i)-(ix) above wherein said G1 protein is any one of the isoforms of G1, analogs, fragments and derivatives of any thereof.

(xi) A method according to any of the above (i)-(x) wherein the G1 protein or any of its isoforms, analogs, fragments or derivatives is involved in the modulation of the cellular effect mediated or modulated by any other cytotoxic mediator or inducer to which said G1 protein, isoform, analog, fragment or derivative is capable of binding directly or indirectly.

(xii) A method for screening other substances such as, for example, peptides, organic compounds, antibodies, etc. to obtain specific drugs which are capable of inhibiting the activity of G1, e.g. inhibiting G1α protease activity thereby inhibiting cell cytotoxicity, or inhibiting G1β activity thereby enhancing cell cytotoxicity.

Embodiments of the above screening method of (xii) include:

(1) A method for screening of a ligand capable of binding to a G1 protein of the invention as noted above, comprising contacting an affinity chromatography matrix to which said protein is attached with a cell extract whereby the ligand is bound to said matrix, and eluting, isolating and analyzing said ligand.

(2) A method for screening of a DNA sequence coding for a ligand capable of binding to a G1 protein of the invention, comprising applying the yeast two-hybrid procedure in which a sequence encoding said protein is carried by one hybrid vector and sequences from a cDNA or genomic DNA library are carried by the second hybrid vector, transforming yeast host cells with said vectors, isolating the positively transformed cells, and extracting said second hybrid vector to obtain a sequence encoding said ligand.

(3) A method for identifying and producing a ligand capable of modulating the cellular activity modulated/mediated by MORT-1 or MORT-1-binding proteins comprising:

a) screening for a ligand capable of binding to a polypeptide comprising at least a portion of MORT-1 or MORT-1-binding proteins selected from MACH proteins, Mch4 proteins and other MORT-1-binding proteins;
b) identifying and characterizing a ligand, other than MORT-1 or said MORT-1-binding proteins or portions of a receptor of the TNF/NGF receptor family, found by said screening step to be capable of said binding; and
c) producing said ligand in substantially isolated and purified form.
(4) A method for identifying and producing a ligand capable of modulating the cellular activity modulated or mediated by a G1 protein of the invention, comprising:
a) screening for a ligand capable of binding to a polypeptide comprising at least a portion of the G1α sequence depicted in FIG. 1 or at least a portion of the G1β sequence depicted in FIG. 2;
b) identifying and characterizing a ligand, other than MORT-1 or MORT-1-binding proteins or portions of a receptor of the TNF/NGF receptor family, found by said screening step to be capable of said binding; and
c) producing said ligand in substantially isolated and purified form.
(5) A method for identifying and producing a ligand capable of modulating the cellular activity modulated/mediated by G1 comprising:
a) screening for a ligand capable of binding to at least a portion of the G1α sequence depicted in FIG. 1 or the G1β sequence depicted in FIG. 2;
b) identifying and characterizing a ligand, other than MORT-1 or MORT-1-binding proteins or portions of a receptor of the TNF/NGF receptor family, found by said screening step to be capable of said binding; and
c) producing said ligand in substantially isolated and purified form.
(6) A method for identifying and producing a molecule capable of directly or indirectly modulating the cellular activity modulated/mediated by G1, comprising:
a) screening for a molecule capable of modulating activities modulated/mediated by G1
b) identifying and characterizing said molecule; and
c) producing said molecule in substantially isolated and purified form.
(7) A method for identifying and producing a molecule capable of directly or indirectly modulating the cellular activity modulated/mediated by a G1 protein of the invention, comprising:
a) screening for a molecule capable of modulating activities modulated/mediated by said G1 protein;
b) identifying and characterizing said molecule; and
c) producing said molecule in substantially isolated and purified form.

The present invention also provides a pharmaceutical composition for the modulation of the FAS-R ligand- or TNF-effect on cells or the effect of any other cytotoxic mediator or inducer on cells as noted above, comprising, as active ingredient any one of the following:
(i) a G1 protein according to the invention, and biologically active fragments, analogs, derivatives of mixtures thereof;
(ii) a recombinant animal virus vector encoding a protein capable of binding a cell surface receptor and encoding a G1 protein or biologically active fragments or analogs, according to the invention;
(iii) an oligonucleotide sequence encoding an anti-sense sequence of the G1 protein sequence according to the invention, wherein said oligonucleotide may be the second sequence of the recombinant animal virus vector of (ii) above.

The present invention also provides:
I. a method for the modulation of the MORT-1-induced effect or MORT-1-binding protein-induced effect, or the effect of any other cytotoxic mediator or inducer, on cells comprising treating said cells in accordance with a method of any one of (i)-(x) above, with G1 proteins, analogs, fragments or derivatives thereof or with sequences encoding G1 proteins, analogs or fragments thereof, said treatment resulting in the enhancement or inhibition of said MORT-1-mediated effect, and thereby also of the FAS-R or p55-R-mediated effect, or of said other cytotoxic mediator or inducer.

II. a method as above wherein said G1 protein, analog, fragment or derivative thereof is that part of the G1 protein which is specifically involved in binding to MORT-1 or MORT-1-binding proteins, or said other cytotoxic mediator or inducer, or said G1 protein sequence encodes that part of G1 protein which is specifically involved in binding to MORT-1 or the MORT-1-binding proteins, or said other cytotoxic mediator or inducer.

III. a method as above wherein said G1 protein is any one of the G1 isoforms, said isoforms capable of enhancing the MORT-1-associated effect, or other cytotoxic mediator or inducer associated effect on cells and thereby also of enhancing the FAS-R- or p55-R-associated effect on cells, or the other cytotoxic mediator or inducer effect on cells.

IV. a method as above wherein said G1 protein is any one of the G1 isoforms, said isoforms capable of inhibiting the MORT-1-associated effect, or other cytotoxic mediator or inducer associated effect on cells and thereby also of inhibiting the FAS-R- or p55-R-associated effect on cells, or the other cytotoxic mediator or inducer effect on cells.

As arises from all the above-mentioned, as well as from the detailed description hereinbelow, G1 may also be used in a MORT-1 independent fashion to treat cells or tissues. Isolation of the G1 proteins, their identification and characterization may be carried out by any of the standard screening techniques used for isolating and identifying proteins, for example, the yeast two-hybrid method, affinity chromatography methods, and any of the other well-known standard procedures used for this purpose.

Furthermore, some isoforms of G1 may have only a protease-like region (with homology to the above mentioned protease regions of other known proteases) but which has no actual protease activity, with the result that such isoforms may serve primarily an inhibitory role as noted above.

Moreover, as G1 or any of its isoforms may be involved in modulating MORT-1-independent intracellular pathways, G1 or any of its isoforms may be involved in the modulation of the signaling of any other intracellular pathways or mechanisms.

Other aspects and embodiments of the present invention are also provided as arising from the following detailed description of the invention.

It should be noted that, where used throughout, the following terms: "Modulation of the FAS-ligand or TNF effect on cells"; and "Modulation of the MORT-1 or MORT-1-binding protein effect on cells" are understood to encompass in vitro as well as in vivo treatment and, in addition, also to emcompass inhibition or enhancement/augmentation.

BRIEF DESCRIPTION OF THE DRAWINGS

FIGS. 1A-1C depict schematically a comparison of the amino acid sequences of the human (hCASHα, hCASHβ) G1 (or CASH) and mouse (mCASHα) splice variants, and conserved motifs found in these proteins. In FIGS. 1A-1C, there is shown a co-linear amino acid sequence alignment of mouse G1α (mCASHα) (SEQ ID NO:5), human G1α(hCASHα) (SEQ ID NO:2) and G1β (hCASHβ) (SEQ ID NO:4), CASP-8 (MACH/FLICE1/Mch5) (SEQ ID NO:6), CASP-10 (Mch4/FLICE2) (SEQ ID NO:7), CASP-3 (CPP32/Apopain/Yama) (SEQ ID NO:8) and CASP-1 (ICE) prodomain regions. Amino acid residues are numbered to the right of each sequence. Dotted lines indicate gaps in the sequence to allow optimal alignment. The 'death domain' modules (DED) are shaded. Amino acids that are identical in more than three of the proteins shown are boxed. Within the region of protease homology, amino acids aligned with CASP-1 residues that were implicated in catalytic activity by X-ray crystallography are denoted as follows: The residues putatively involved in catalysis, corresponding to His237 and Cys285 in CASP-1, are darkly shaded and marked by closed circles below the alignment. The residues constituting the binding pocket for the carboxylate side chain of the P1 Asp, corresponding to Arg179, Gln 238, Arg341and Ser347 in CASP-1, are less heavily shaded and marked by open circles. Known and suggested Asp-X cleavage sites and the potential site of cleavage found at a similar location in G1 (CASH) are shaded. Horizontal arrows indicate the N- and C-terminal ends of the small and large subunits of the CASP-1. The C-termini of the proteins are denoted by asterisks.

FIGS. 4A-4D are presentations of the results showing the effects of G1α (CASHα), G1β (CASHβ) and G1α (CASHα) mutants on cell viability and cell death induction. Quantification of cell death induced in HeLa-Fas cells (results depicted schematically as bar-graphs in FIG. 4A) and in 293-T cells (results depicted schematically as bar-graphs in FIGS. 4B and 4C) by transfection of these cells with the indicated constructs was performed as noted in Example 1. Cells ($5 \times 10^5$ 293T cells or $3 \times 10^5$ HeLa cells per 6-cm dishes) were transiently transfected with the cDNAs of the indicated proteins together with the pCMV-β-gal, using the calcium phosphate precipitation method. Each dish was transfected with 5 μg of the pcDNA3 construct of interest or, when transfecting two different constructs, 2.5 μg of each, and 1.5 μg of β-galactosidase expression vector. Cells were rinsed 6 to 10 h after transfection and then incubated for a further 14 h without additional treatment. Anti-CD95 (Anti-Fas-R) monoclonal antibody (CH11 (Oncor (Gaithersburg, Md.)), 0.5 μ.ml) and human recombinant TNFα (100 ng/ml) were applied to the cells together with cycloheximide (CHX, 10 μg/ml) and incubated for an additional 4 h. Cells were then stained with 5-bromo-4-chloro-3-indoxyl-β-D-galactopyranoside (X-Gal) and examined by phase contrast microscopy. In all experiments shown, death was assessed 24 h after transfection for HeLa-Fas cells and 20 h after transfection for 293T cells. Data shown (mean±SD; n equals at least three experiments) are the percentage of blue cells counted that showed membrane blebbing.

In FIG. 4D there are shown reproductions of micrographs depicting the morphology of 293-T cells transiently expressing the indicated constructs. Pictures were taken 20 h after transfection.

DETAILED DESCRIPTION OF THE INVENTION

Figure 2B:
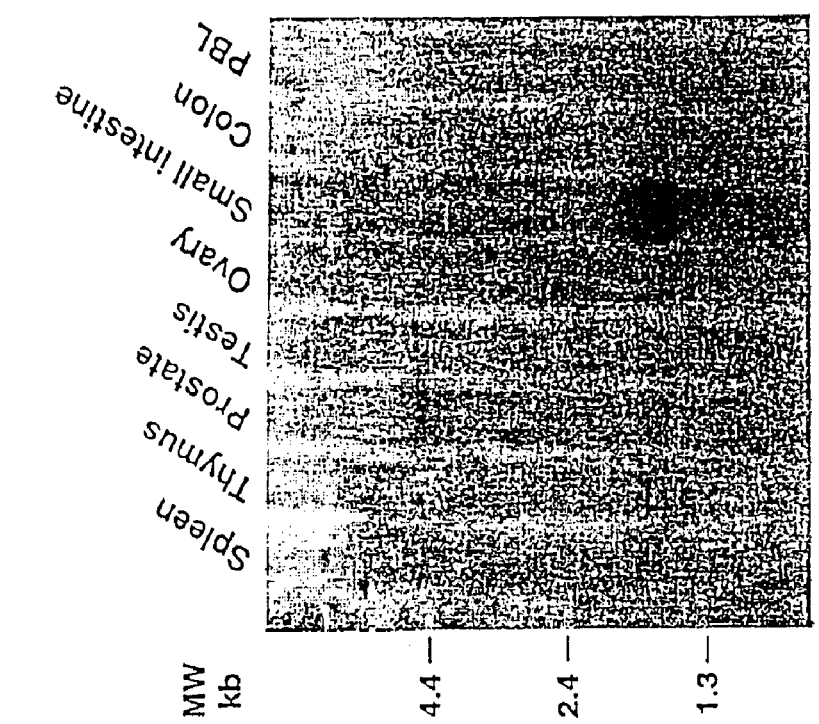
FIGS. 2A and 2B show reproductions of autoradiograms of Northern blots depicting the identification of G1 transcripts in various human tissues (heart, brain, placenta, lung, liver, skeletal muscle, kidney, pancreas, spleen, thymus, prostate, testis, ovary, small intestine, colon and peripheral blood lymphocytes—PBL). The Northern blot analysis was performed as follows: A radiolabeled mRNA probe corresponding to the 'death domain' (DED) module region of G1 (from nucleotide nos. 482-1070 in G1β (SEQ ID NO:2), a region common to both G1 (CASH) splice variants cloned) was prepared using the T7 RNA polymerase (Promega) and used for analysis of human multiple tissue blots (Clontech), containing poly(A)+ RNA (2 μg per lane) of various human tissues.

The present invention relates, in one aspect, to novel G1 proteins which are capable of binding to or interacting directly or indirectly with MORT-1 or with MORT-1-binding proteins such as, for example, Mch4 and MACH and thereby of binding to the intracellular domain of the FAS-R receptor, to which MORT-1 binds, or of binding to the intracellular domain of the p55 TNF-R, to which the protein TRADD binds and to which TRADD protein MORT-1 binds. Hence, the G1 proteins of the present invention are considered as mediators or modulators of FAS-R, having a role in, for example, the signaling process that is initiated by the binding of FAS ligand to FAS-R, and likewise also having a role in the signaling process that is initiated by the binding of TNF to p55-R. Of the G1 proteins of the present invention are included the newly discovered G1 and its isoforms.

More particularly, in accordance with the present invention, a new protein G1 (also called CASH), which is apparently a homolog of the nematode protease CED3 has been disclosed. This new G1 protein which, although being closely related, does however display some differences of structure and of substrate specificity, and as such may serve somewhat different functions in mammalian cells. Indeed, two different activities of the proteases are known. The main role of ICE (also called CASP-1) seems to be the processing of the IL-1β precursor, while CED3 has been clearly shown to serve as an effector of programmed cell death. This latter role also appears to be the role of at least some of the mammalian homologs, for example some of the MACH (also called CASP-8) isoforms of the above noted co-owned co-pending patent applications, as well as the above mentioned related Mch4 (also called CASP-10) to which G1 of the present invention binds. The amino acid sequence of the MACHα1 shows closest resemblance to CPP32 (also called CASP-3), the closest known mammalian homolog of CED3. The substrate specificity of MACH is also similar to that of CPP32, except that MACHα1 seems to have a more restricted substrate specificity than that of CPP32. CPP32 cleaves preferentially the substrate peptide corresponding to a cleavage site in poly (ADP ribose) polymerase (PARP), yet also has some proteolytic activity against the peptide corresponding to the ICE cleavage site in the IL-1β precursor. MACHα1 seems, however, to be solely capable of cleaving the PARP-derived sequence. These relationships of MACHα1 to CPP32 and CED3, and its dissimilarities to ICE, are consistent with the idea that MACHα1 serves, similarly to CED3, as regulator of cell death. MACHα1 displays, though, some sequence features which distinguish it from CED3 and from CPP32, as well as from all other members of the CED3/ICE family. The C terminal part of MACHα1, upstream to its CED3/ICE homology region, shows no resemblance at all to the upstream region of any of the other homologs. There are also some unique sequence features to the CED3/ICE homology region of the protein. These differences suggest that MACHα1 belongs to a distinct evolutionary branch of the family and that its contribution to cell death somewhat differs from that of the previously described CED3/ICE homologs. Likewise the G1 protein of the present invention and its possible isoforms also show some distinct differences in the CED3/ICE homology region within the G1 sequence and as such these differences may represent unique features reflecting specificity of activity for G1 in mammalian cells.

One important difference may concern the way in which the function of the protease is regulated. Being involved both in developmentally related cell death processes and in receptor-induced immune cytolysis, the cleavage of proteins by proteases of the CED3/ICE family should be amenable to regulation both by signals that are formed within the cell and by signals emanating from cell surface receptors. In developmental cell death processes, the activation of such proteases seems to involve mechanisms that affect gene expression, resulting in enhanced synthesis of the proteases, as well as in decreased synthesis of proteins like BCL-2, that antagonize their apoptopic effect. This is clearly not the case, however, for the cytotoxicity triggered by FAS-R or the TNF receptors. Cells can be killed by TNF or the FAS-R ligand even when their protein synthesis activity is fully blocked (they are in fact killed more effectively then) and remain stimulus-dependent under these conditions. Activation of proteases of the CED3/ICE family by the TNF receptors and FAS-R may thus occur by a mechanism which is protein-synthesis-independent. The unique sequence properties of MACHα1 may allow it to take part in such a mechanism. Similarly, the unique sequence properties of the G1 protein of the present invention may also endow it with an ability to take part in such a mechanism.

Thus, the new G1 protein may be yet another member of the recently found group of proteases including the above mentioned MACH (and its isoforms) and Mch4 which have been found to associate, either directly or through an adapter protein, with the intracellular domain of a cell surface receptor. By inference from the way of action of receptor-associated proteins that have other enzymatic activities, it seems plausible that the binding of G1 to Mch4 or of G1 to MACH (or isoform Machα1) and, in turn, the binding of Mch4 of Mach to MORT-1, or the direct binding of G1 to MORT1 allows the stimulation of the G1 and/or Mch4 and/or the MACH protease activity upon triggering of FAS-R by Fas ligand. It may also allow activation of the protease by the p55-R, through the binding of MORT1 to TRADD, which binds to p55-R.

Other members of the CED3/ICE family were found to exhibit full activity only after proteolytic processing, which occurs either by their self-cleavage or by effects of other proteases of this family (reviewed in Kumas, 1995; Henkart, 1996). For example, as detailed in the above mentioned co-owned and co-pending patent applications regarding MACH, the cytotoxic effect resulting from co-expression of the two major potential self-cleavage products of MACHα1, as opposed to the lack of cytotoxicity in cells that express the full-length CED3/ICE homology region, is consistent with the possibility that also MACHα1 gains full activity only after its processing. The enzymatic activity observed in lysates of bacteria that express the full length region apparently reflect self processing of the protein produced under these conditions or processing by some bacterial proteases. In what way this processing occurs within the mammalian cell, and how it can be brought about by triggering of FAS-R and p55-R, is not known, nor is it clear yet what relative contribution the protease activity of MACHα1 makes to the FAS-R- and and TNF-induced cytotoxicity. Evaluation of this contribution is complicated by the fact that also expression of MACHβ1, which lacks the CED3/ICE homology region, results in marked cytotoxicity. Presumably, this cytotoxicity reflects the ability of MACHβ1 to bind to MACHα1. Due to this ability, transfected MACH molecules may impose, upon aggregation, a conformational change in the MACHα1 molecules that are endogenous to the transfected cell. Such a mechanism may well account also for the cytotoxicity observed when molecules that act upstream to MACH, (MORT1, TRADD or the death domains of either the p55-R or FAS-R) are over-expressed in cells. At the moment, however, one cannot exclude that the cytotoxicity observed upon induced expression of MACH or of molecules that act upstream to it reflect, besides the proteolytic activity of the CED3/ICE homology region in MACH, also activation of some of the other mechanisms believed to take part in the FAS-R and p55-R cytotoxic effect (for example, activation of the neutral or acid sphingomyelinase). One also cannot exclude that the proteolytic activity of the CED3/ICE homology region serves other functions besides cytotoxicity induction. A clearer idea of the function of MACHα1 should be gained by identification of the endogenous substrate proteins that are cleaved upon activation of MACHα1. Finding ways to ablate the activity of MACHα1 at will, for example by expression of inhibitory molecules, will also contribute to understanding of the function of this protein, and serve as a way for regulating its activity when desired.

Hence, the G1 protein of the present invention and its possible isoforms may behave in an analogous fashion to that mentioned for the above MACH proteins with or without direct interaction with other proteins, namely, G1 may act directly via binding to MORT-1 or may act indirectly via binding to Mch4 and/or MACH and in turn by the binding of Mch4 and/or MACH to MORT-1 or in some other as yet not elucidated mechanism specific for G1. Similarly, the regulation of G1 activity may be analogous to that envisioned above for MACH protein regulation.

There may well exist within cells that express G1 natural inhibitors of the protease encompassed in this protein. Existence of alternatively spliced isoforms for some of the other members of the CED3/ICE family has been shown to constitute a way of physiological restriction of the function of these proteases. Some of the isoforms of these other proteases were reported to act as natural inhibitors of the full-length isoforms, apparently by forming inactive heterodimers, with them. This may well be the case also for G1 and some of its posible isoforms, for example those isoforms in which the potential N-terminal cleavage site is missing. Expression of such inhibitory isoforms may constitute a mechanism of cellular self-protection against the FAS-R and TNF cytotoxicity.

G1 may have yet other functions, for example, G1 or any of its isoforms may have an enhancing or augmenting effect on other proteins with enzymatic activity, e.g. the proteolytic activities of various Mch4 and MACH isoforms, this enhancing or augmenting activity being via a mechanism whereby G1 serves to recruit other proteins to bind MORT-1 (e.g. Mch4 and MACH proteins). Further, G1 or any of its isoforms may also serve roles not related to cytotoxicity, but rather may act as docking sites for molecules that are involved in other non-cytotoxic, effects of FAS-R and TNF.

Some of the specific G1 isoforms in accordance with the present invention are exemplified in Example 1 below. One of these called G1α (CASHα) isolated from human and mouse (hG1α/hCASHα and mG1α/mCASHα, respectively) is apparently a 1 mg splice variant having a protease homology region and, at least in some cells (e.g. 293 cells), has cytotoxic activity. Another of these is called G1β (CASHβ) isolated from human, is apparently a short splice variant without a protease homology region and which actually inhibits cell-death signaling pathways.

Due to the unique ability of FAS-R and the TNF receptors to cause cell death, as well as the ability of the TNF receptors to trigger various other tissue-damaging activities, aberration of the function of these receptors can be particularly deleterious to the organism. Indeed, both excessive and deficient function of these receptors have been shown to contribute to the pathological manifestations of various diseases. Identifying molecules that take part in the signaling activity of these receptors, and finding ways to modulate the function of these molecules, constitutes a potential clue for new therapeutical approaches to these diseases. In view of the suspected important role of G1 in FAS-R and TNF toxicity, it seems particularly important to design drugs that can block the proteolytic function of this molecule, as has been done for some other members of the CED3/ICE family. The unique sequence features of the CED3/ICE homolog encompassed in the G1 molecules may allow designing drugs that can affect its protection from excessive immune-mediated cytotoxicity without interfering with physiological cell death processes, in which other members of the CED3/ICE family are involved.

As mentioned above, G1 or any of its isoforms may also be involved in the modulation of other intracellular signaling pathways, such as, for example, of other cytotoxic mediators or inducers, or other proteins in a MORT-1 or MORT-1-binding protein-independent fashion. Further, G1 or at least its isoforms which have a protease-like region without actual protease activity may be involved in primarily an inhibitory function, namely, inhibiting those pathways, e.g. signaling pathways in general or cytotoxic pathways in particular, in which G1 or its isoforms are involved either by binding directly to members of these pathways or by binding indirectly to other proteins, which, in turn, bind to members of these pathways.

Thus, the present invention also concerns the DNA sequence encoding a G1 protein and the G1 proteins encoded by the DNA sequences.

Moreover, the present invention further concerns the DNA sequences encoding biologically active analogs, fragments and derivatives of the G1 protein, and the analogs, fragments and derivatives encoded thereby. The preparation of such analogs, fragments and derivatives is by standard procedure (see for example, Sambrook et al., 1989) in which in the DNA sequences encoding the G1 protein, one or more codons may be deleted, added or substituted by another, to yield analogs having at least one amino acid residue change with respect to the native protein.

A polypeptide or protein "substantially corresponding" to G1 protein includes not only G1 protein but also polypeptides or proteins that are analogs of G1.

Analogs that substantially correspond to G1 protein are those polypeptides in which one or more amino acid of the G1 protein's amino acid sequence has been replaced with another amino acid, deleted and/or inserted, provided that the resulting protein exhibits substantially the same or higher biological activity as the G1 protein to which it corresponds.

In order to substantially correspond to G1 protein, the changes in the sequence of G1 proteins, such as isoforms are generally relatively minor. Although the number of changes may be more than ten, preferably there are no more than ten changes, more preferably no more than five, and most preferably no more than three such changes. While any technique can be used to find potentially biologically active proteins which substantially correspond to G1 proteins, one such technique is the use of conventional mutagenesis techniques on the DNA encoding the protein, resulting in a few modifications. The proteins expressed by such clones can, then be screened for their ability to bind to various MORT-1-binding proteins, such as, for example, Mch4 and MACH, or even directly to MORT-1, and/or FAS-R and p55-R mediating activity, and/or to mediating activity of any other intracellular pathway in ways noted above.

"Conservative" changes are those changes which would not be expected to change the activity of the protein and are usually the first to be screened as these would not be expected to substantially change the size, charge or configuration of the protein and thus would not be expected to change the biological properties thereof.

Conservative substitutions of G1 proteins include an analog wherein at least one amino acid residue in the polypeptide has been conservatively replaced by a different amino acid. Such substitutions preferably are made in accordance with the following list as presented in Table IA, which substitutions may be determined by routine experimentation to provide modified structural and functional properties of a synthesized polypeptide molecule while maintaining the biological activity characteristic of G1 protein.

TABLE IA

| Original Residue | Exemplary Substitution |
|---|---|
| Ala | Gly; Ser |
| Arg | Lys |
| Asn | Gln; His |
| Asp | Glu |
| Cys | Ser |
| Gln | Asn |
| Glu | Asp |
| Gly | Ala; Pro |
| His | Asn; Gln |
| Ile | Leu; Val |
| Leu | Ile; Val |
| Lys | Arg; Gln; Glu |
| Met | Leu; Tyr; Ile |
| Phe | Met; Leu; Tyr |
| Ser | Thr |
| Thr | Ser |
| Trp | Tyr |
| Tyr | Trp; Phe |
| Val | Ile; Leu |

Alternatively, another group of substitutions of G1 protein are those in which at least one amino acid residue in the polypeptide has been removed and a different residue inserted in its place according to the following Table IB. The types of substitutions which may be made in the polypeptide may be based on analysis of the frequencies of amino acid changes between a homologous protein of different species, such as those presented in Table 1-2 of Schulz et al., G. E., Principles of Protein Structure Springer-Verlag, New York, N.Y., 1798, and FIGS. 3-9 of Creighton, T. E., Proteins: Structure and Molecular Properties, W.H. Freeman & Co., San Francisco, Calif. 1983. Based on such an analysis, alternative conservative substitutions are defined herein as exchanges within one of the following five groups:

TABLE IB

1. Small aliphatic, nonpolar or slightly polar residues: Ala, Ser, Thr (Pro, Gly);
2. Polar negatively charged residues and their amides: Asp, Asn, Glu, Gln;
3. Polar, positively charged residues: His, Arg, Lys;
4. Large aliphatic nonpolar residues: Met, Leu, Ile, Val (Cys); and
5. Large aromatic residues: Phe, Tyr, Trp.

The three amino acid residues in parentheses above have special roles in protein architecture. Gly is the only residue lacking any side chain and thus imparts flexibility to the chain. This however tends to promote the formation of secondary structure other than a-helical. Pro, because of its unusual geometry, tightly constrains the chain and generally tends to promote β-turn-like structures, although in some cases Cys can be capable of participating in disulfide bond formation which is important in protein folding. Note that Schulz et al., supra, would merge Groups 1 and 2, above. Note also that Tyr, because of its hydrogen bonding potential, has significant kinship with Ser, and Thr, etc.

Conservative amino acid substitutions according to the present invention, e.g., as presented above, are known in the art and would be expected to maintain biological and structural properties of the polypeptide after amino acid substitution. Most deletions and substitutions according to the present invention are those which do not produce radical changes in the characteristics of the protein or polypeptide molecule. "Characteristics" is defined in a non-inclusive manner to define both changes in secondary structure, e.g. a-helix or β-sheet, as well as changes in biological activity, e.g., binding of MORT-1-binding proteins or of MORT-1 or mediation of FAS-R ligand or TNF effect on cells.

Examples of production of amino acid substitutions in proteins which can be used for obtaining analogs of G1 proteins for use in the present invention include any known method steps, such as presented in U.S. patent RE 33,653, U.S. Pat. Nos. 4,959,314, 4,588,585 and 4,737,462, to Mark et al.; U.S. Pat. No. 5,116,943 to Koths et al., U.S. Pat. No. 4,965,195 to Namen et al.; U.S. Pat. No. 4,879,111 to Chong et al.; and U.S. Pat. No. 5,017,691 to Lee et al.; and lysine substituted proteins presented in U.S. Pat. No. 4,904,584 (Shaw et al.).

Besides conservative substitutions discussed above which would not significantly change the activity of G1 protein, either conservative substitutions or less conservative and more random changes, which lead to an increase in biological activity of the analogs of G1 proteins, are intended to be within the scope of the invention.

When the exact effect of the substitution or deletion is to be confirmed, one skilled in the art will appreciate that the effect of the substitution(s), deletion(s), etc., will be evaluated by routine binding and cell death assays. Screening using such a standard test does not involve undue experimentation.

Acceptable analogs are those which retain at least the capability of binding to MORT-1-binding proteins as noted above or binding to MORT-1 or other proteins, and thereby, as noted above mediate the activity of the FAS-R and p55-R or other proteins as noted above. In such a way, analogs can be produced which have a so-called dominant-negative effect, namely, an analog which is defective either in binding to MORT-1-binding proteins (e.g. Mch4 or MACH) or binding to MORT-1, or other proteins, or in subsequent signaling or protease activity following such binding. Such analogs can be used, for example, to inhibit the FAS-ligand-effect or effect of other proteins by competing with the natural MORT-1-binding proteins or other proteins. For example, it appears likely that the MACH isoforms, MACHα2 and MACHα3 are "natural" analogs which serve to inhibit MACH activity by competing with the binding of the active (protease) MACH isoforms to MORT-1 which appears to be essential for the activation of these MACH isoforms. Once the active MACH isoforms cannot bind to MORT-1, the intracellular signaling pathways mediated by FAS-R and p55-R will thereby also be inhibited. In a similar fashion G1 or any of its isoforms may also serve as inhibitors of the FAS-ligand effect by competing with various of the MORT-1-binding proteins to bind MORT-1 or by interacting with them in a way that prevents their binding to MORT-1. Likewise, so-called dominant-positive G1 analogs may be produced which would serve to enhance the FAS ligand or TNF effect. These would have the same or better ability to bind MORT-1-binding proteins or even the same or better MORT-1-binding properties and the same or better signaling properties of the natural G1 proteins.

At the genetic level, these analogs are generally prepared by site-directed mutagenesis of nucleotides in the DNA encoding the G1 protein, thereby producing DNA encoding the analog, and thereafter synthesizing the DNA and expressing the polypeptide in recombinant cell culture. The analogs typically exhibit the same or increased qualitative biological activity as the naturally occurring protein, Ausubel et al., Current Protocols in Molecular Biology, Greene Publications and Wiley Interscience, New York, N.Y., 1987-1995; Sambrook et al., Molecular Cloning: A Laboratory Manual, Cold Spring Harbor Laboratory, Cold Spring Harbor, N.Y., 1989.

Preparation of a G1 protein in accordance herewith, or an alternative nucleotide sequence encoding the same polypeptide but differing from the natural sequence due to changes permitted by the known degeneracy of the genetic code, can be achieved by site-specific mutagenesis of DNA that encodes an earlier prepared analog or a native version of a G1 protein. Site-specific mutagenesis allows the production of analogs through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 complementing nucleotides on each side of the sequence being altered. In general, the technique of site-specific mutagenesis is well known in the art, as exemplified by publications such as Adelman et al., *DNA* 2:183 (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, Editor A. Walton, Elsevier, Amsterdam (1981), the disclosure of which is incorporated herein by reference. These phage are readily available commercially and their use is generally well known to those skilled in the art. Alternatively, plasmid vectors that contain a single-stranded phage origin of replication (Veira et al., *Meth. Enzymol.* 153:3, 1987) may be employed to obtain single-stranded DNA.

In general, site-directed mutagenesis in accordance herewith is performed by first obtaining a single-stranded vector that includes within its sequence a DNA sequence that encodes the relevant polypeptide. An oligonucleotide primer bearing the desired mutated sequence is prepared synthetically by automated DNA/oligonucleotide synthesis. This primer is then annealed with the single-stranded protein-sequence-containing vector, and subjected to DNA-polymerizing enzymes such as $E.$ $coli$ polymerase I Klenow fragment, to complete the synthesis of the mutation-bearing strand. Thus, a mutated sequence and the second strand bears the desired mutation. This heteroduplex vector is then used to transform appropriate cells, such as $E.$ $coli$ JM101 cells, and clones are selected that include recombinant vectors bearing the mutated sequence arrangement.

After such a clone is selected, the mutated G1 protein may be removed and placed in an appropriate vector, generally a transfer or expression vector of the type that may be employed for transfection of an appropriate host.

Accordingly, a gene or nucleic acid encoding for a G1 protein can also be detected, obtained and/or modified, in vitro, in situ and/or in vivo, by the use of known DNA or RNA amplification techniques, such as PCR and chemical oligonucleotide synthesis. PCR allows for the amplification (increase in number) of specific DNA sequences by repeated DNA polymerase reactions. This reaction can be used as a replacement for cloning; all that is required is a knowledge of the nucleic acid sequence. In order to carry out PCR, primers are designed which are complementary to the sequence of interest. The primers are then generated by automated DNA synthesis. Because primers can be designed to hybridize to any part of the gene, conditions can be created such that mismatches in complementary base pairing can be tolerated. Amplification of these mismatched regions can lead to the synthesis of a mutagenized product resulting in the generation of a peptide with new properties (i.e., site directed mutagenesis). See also, e.g., Ausubel, supra, Ch. 16. Also, by coupling complementary DNA (cDNA) synthesis, using reverse transcriptase, with PCR, RNA can be used as the starting material for the synthesis of the extracellular domain of a prolactin receptor without cloning.

Furthermore, PCR primers can be designed to incorporate new restriction sites or other features such as termination codons at the ends of the gene segment to be amplified. This placement of restriction sites at the 5' and 3' ends of the amplified gene sequence allows for gene segments encoding G1 protein or a fragment thereof to be custom designed for ligation to other sequences and/or cloning sites in vectors.

PCR and other methods of amplification of RNA and/or DNA are well known in the art and can be used according to the present invention without undue; experimentation, based on the teaching and guidance presented herein. Known methods of DNA or RNA amplification include, but are not limited to polymerase chain reaction (PCR) and related amplification processes (see, e.g., U.S. Pat. Nos. 4,683,195, 4,683,202, 4,800,159, 4,965,188, to Mullis et al.; U.S. Pat. Nos. 4,795,699 and 4,921,794 to Tabor et al.; U.S. Pat. No. 5,142,033 to Innis; U.S. Pat. No. 5,122,464 to Wilson et al.; U.S. Pat. No. 5,091,310 to Innis; U.S.Pat No. 5,066,584 to Gyllensten et al.; U.S. Pat. No. 4,889,818 to Gelfand et al.; U.S. Pat. No. 4,994,370 to Silver et al.; U.S. Pat. No. 4,766,067 to Biswas; U.S. Pat. No. 4,656,134 to Ringold; and Innis et al., eds., *PCR Protocols: A Guide to Method and Applications*) and RNA mediated amplification which uses anti-sense RNA to the target sequence as a template for double stranded DNA synthesis (U.S. Pat. No. 5,130,238 to Malek et al., with the tradename NASBA); and immuno-PCR which combines the use of DNA amplification with antibody labeling (Ruzicka et al., *Science* 260:487 (1993); Sano et al., *Science* 258:120 (1992); Sano et al., *Biotechniques* 9:1378 (1991)), the entire contents of which patents and reference are entirely incorporated herein by reference.

In an analogous fashion, biologically active fragments of G1 proteins (e.g. those of any of the G1 or its isoforms) may be prepared as noted above with respect to the analogs of G1 proteins. Suitable fragments of G1 proteins are those which retain the G1 capability and which can mediate the biological activity of FAS-R and p55-R or other proteins as noted above. Accordingly, G1 protein fragments can be prepared which have a dominant-negative or a dominant-positive effect as noted above with respect to the analogs. It should be noted that these fragments represent a special class of the analogs of the invention, namely, they are defined portions of G1 proteins derived from the full G1 protein sequence (e.g., from that of any one of the G1 or its isoforms), each such portion or fragment having any of the above-noted desired activities. Such fragment may be, e.g., a peptide.

Similarly, derivatives may be prepared by standard modifications of the side groups of one or more amino acid residues of the G1 protein, its analogs or fragments, or by conjugation of the G1 protein, its analogs or fragments, to another molecule e.g. an antibody, enzyme, receptor, etc., as are well known in the art. Accordingly, "derivatives" as used herein covers derivatives which may be prepared from the functional groups which occur as side chains on the residues or the N- or C-terminal groups, by means known in the art, and are included in the invention. Derivatives may have chemical moieties such as carbohydrate or phosphate residues, provided such a fraction has the same or higher biological activity as G1 proteins.

For example, derivatives may include aliphatic esters of the carboxyl groups, amides of the carboxyl groups by reaction with ammonia or with primary or secondary amines, N-acyl derivatives or free amino groups of the amino acid residues formed with acyl moieties (e.g., alkanoyl or carbocyclic aroyl groups) or O-acyl derivatives of free hydroxyl group (for example that of seryl or threonyl residues) formed with acyl moieties.

The term "derivatives" is intended to include only those derivatives that do not change one amino acid to another of the twenty commonly occurring natural amino acids.

Although G1 protein is a protein or polypeptide, it is a sequence of amino acid residues. A polypeptide consisting of a larger sequence which includes the entire sequence of a G1 protein, in accordance with the definitions herein, is intended to be included within the scope of such a polypeptide as long as the additions do not affect the basic and novel characteristics of the invention, i.e., if they either retain or increase the biological activity of G1 protein or can be cleaved to leave a protein or polypeptide having the biological activity of G1 protein. Thus, for example, the present invention is intended to include fusion proteins of G1 protein with other amino acids or peptides.

The new G1 protein, their analogs, fragments and derivatives thereof, have a number of possible uses, for example:

(i) G1 protein, its analogs, fragments and derivatives thereof, may be used to mimic or enhance the function of MORT-1-binding proteins such as, for example, Mch4 and MACH (including its various isoforms), or even of MORT-1 itself, and hence the FAS-R ligand or TNF, or other proteins, in situations where an enhanced FAS-R ligand or TNF or other protein effect is desired, such as in anti-tumor, anti-inflammatory, anti-HIV applications, etc., where the FAS-R ligand- or TNF- or other protein-induced cytotoxicity is desired. In this case the G1 protein, its analogs, fragments or derivatives thereof, which enhance the FAS-R ligand or TNF or other protein effect, i.e., cytotoxic effect, may be introduced to the cells by standard procedures known per se. For example, when the G1 protein is entirely intracellular (as suspected) and should be introduced only into the cells where the FAS-R ligand or TNF or other protein effect is desired, a system for specific introduction of this protein into the cells is necessary. One way of doing this is by creating a recombinant animal virus, e.g., one derived from Vaccinia, to the DNA of which the following two genes will be introduced: the gene encoding a ligand that binds to cell surface proteins specifically expressed by the cells, e.g., ones such as the AIDs (HIV) virus gp120 protein which binds specifically to some cells (CD4 lymphocytes and related leukemias), or any other ligand that binds specifically to cells carrying a FAS-R or p55-R, such that the recombinant virus vector will be capable of binding such FAS-R- or p55-R -carrying cells; and the gene encoding the G1 protein. Thus, expression of the cell-surface-binding protein on the surface of the virus will target the virus specifically to the tumor cell or other FAS-R- or p55-R-carrying cell, following which the G1 protein encoding sequence (e.g. G1α sequence) will be introduced into the cells via the virus, and once expressed in the cells, will result in enhancement of the FAS-R ligand or TNF effect leading to the death of the tumor cells or other FAS-R- or p55-R-carrying cells it is desired to kill. Construction of such recombinant animal virus is by standard procedures (see for example, Sambrook et al., 1989). Another possibility is to introduce the sequences of the G1 protein (e.g., any one of the G1 or its isoforms) in the form of oligonucleotides which can be absorbed by the cells and expressed therein.

A further way of enhancing such cell cytotoxicity would be to inhibit the activity of G1 isoforms (e.g. G1β) which themselves are inhibitory on cell cytotoxicity. Ways of inhibiting such G1 isoforms are numerous and include those listed under (ii) below as applied specifically to inhibit such inhibitory G1 isoforms such as, for example, G1β.

(ii) They may be used to inhibit the FAS-R ligand or TNF or other protein effect, e.g., in cases such as tissue damage in septic shock, graft-vs.-host rejection, or acute hepatitis, in which it is desired to block the FAS-R ligand or TNF induced FAS-R or p55-R intracellular signaling or other protein-mediated signaling. In this situation, it is possible, for example, to introduce into the cells, by standard procedures, oligonucleotides having the anti-sense coding sequence for the G1 protein, which would effectively block the translation of mRNAs encoding the G1 protein and thereby block its expression and lead to the inhibition of the FAS-R ligand-or TNF- or other protein-effect. Such oligonucleotides may be introduced into the cells using the above recombinant virus approach, the second sequence carried by the virus being the oligonucleotide sequence Further, as noted above and as exemplified below, at least one G1 isoform has been isolated which is a 'natural inhibitor' of cell cytotoxicity, namely, G1β. Hence, such a G1 isoform may be administered directly to cells, or a suitable vector carrying a nucleotide sequence encoding this isoform may be introduced into cells, so that when expressed in the cells this G1 isoform will serve to inhibit cell cytotoxicity.

Another possibility is to use antibodies specific for the G1 protein to inhibit its intracellular signaling activity.

Yet another way of inhibiting the FAS-R ligand or TNF effect is by the recently developed ribozyme approach. Ribozymes are catalytic RNA molecules that specifically cleave RNAs. Ribozymes may be engineered to cleave target RNAs of choice, e.g., the mRNAs encoding the G1 protein of the invention. Such ribozymes would have a sequence specific for the G1 protein mRNA and would be capable of interacting therewith (complementary binding) followed by cleavage of the mRNA, resulting in a decrease (or complete loss) in the expression of the G1 protein, the level of decreased expression being dependent upon the level of ribozyme expression in the target cell. To introduce ribozymes into the cells of choice (e.g., those carrying FAS-R or p55-R), any suitable vector may be used, e.g., plasmid, animal virus (retrovirus) vectors, that are usually used for this purpose (see also (i) above, where the virus has, as second sequence, a cDNA encoding the ribozyme sequence of choice). (For reviews, methods etc. concerning ribozymes see Chen et al., 1992; Zhao and Pick, 1993; Shore et al., 1993; Joseph and Burke, 1993; Shimayama et al., 1993; Cantor et al., 1993; Barinaga, 1993; Crisell et al., 1993 and Koizumi et al., 1993).

(iii) The G1 protein, its analogs, fragments or derivatives may also be used to isolate, identify and clone other proteins of the same class, i.e., those binding to FAS-R intracellular domain or to functionally related receptors, or those binding to the above noted MORT-1-binding proteins, or those binding to MORT-1 and thereby to functionally related receptors such as FAS-R and p55-R, and involved in the intracellular signaling process. In this application the above noted yeast two-hybrid system may be used, or there may be used a recently developed system employing non-stringent Southern hybridization followed by PCR cloning (Wilks et al., 1989). In the Wilks et al. publication, there is described the identification and cloning of two putative protein-tyrosine kinases by application of non-stringent southern hybridization followed by cloning by PCR based on the known sequence of the kinase motif, a conceived kinase sequence. This approach may be used, in accordance with the present invention using the sequence of the G1 protein to identify and clone those of related MORT-1-binding proteins.

(iv) Yet another approach to utilizing the G1 protein, or its analogs, fragments or derivatives thereof, of the invention is to use them in methods of affinity chromatography to isolate and identify other proteins or factors to which they are capable of binding, e.g., MORT-1, MORT-1-binding proteins, or other proteins or factors involved in the intracellular signaling process. In this application, the G1 protein, its analogs, fragments or derivatives thereof, of the present invention, may be individually attached to affinity chromatography matrices and then brought into contact with cell extracts or isolated proteins or factors suspected of being involved in the intracellular signaling process. Following the affinity chromatography procedure, the other proteins or factors which bind to the G1 protein, or its analogs, fragments or derivatives thereof of the invention, can be eluted, isolated and characterized.

(v) As noted above, the G1 protein, or its analogs, fragments or derivatives thereof, of the invention may also be used as immunogens (antigens) to produce specific antibodies thereto. These antibodies may also be used for the purposes of purification of the G1 protein (e.g., G1 or any of its isoforms) either from cell extracts or from transformed cell lines producing G1 protein, or its analogs or fragments. Further, these antibodies may be used for diagnostic purposes for identifying disorders related to abnormal functioning of the FAS-R ligand or TNF system, e.g., overactive or underactive FAS-R ligand- or TNF-induced cellular effects. Thus, should such disorders be related to a malfunctioning intracellular signaling system involving the MORT-1 protein, or various other, above noted MORT-1-binding proteins or G1 protein itself, such antibodies would serve as an important diagnostic tool.

It should also be noted that the isolation, identification and characterization of the G1 protein of the invention may be performed using any of the well known standard screening procedures. For example, one of these screening procedures, the yeast two-hybrid procedure as is set forth herein below, was used to identify the MORT-1 protein and subsequently the various MORT-1-binding proteins and the G1 protein of the invention. Likewise as noted above and below, other procedures may be employed such as affinity chromatography, DNA hybridization procedures, etc. as are well known in the art, to isolate, identify and characterize the G1 protein of the invention or to isolate, identify and characterize additional proteins, factors, receptors, etc. which are capable of binding to the G1 proteins of the invention.

As set forth hereinabove, the G1 protein may be used to generate antibodies specific to G1 proteins, e.g., G1 and its isoforms. These antibodies or fragments thereof may be used as set forth hereinbelow in detail, it being understood that in these applications the antibodies or fragments thereof are those specific for G1 proteins.

Based on the findings in accordance with the present invention that at least some of the G1 or its possible isoforms are proteases related to the proteases of the CED3/ICE family of proteases, the following specific medical applications are envisioned for these G1 proteins and isoforms: it has been found that specific inhibitors of other CED3/ICE proteases, some of which are cell permeable, already exist, which can block effectively programmed cell death processes. Hence, it is possible in accordance with the present invention to design inhibitors that can prevent FAS-R ligand- or TNF-induced cell death, the pathways in which the G1 protease isoforms are involved. Further, in view of the unique sequence features of these new G1 proteases, it seems possible to design inhibitors that will be highly specific to the TNF- and FAS-R ligand-induced effects. The findings of the present invention also provide a way to study the mechanism in which the "killing protease" is activated in response to FAS-R ligand and TNF, this allowing subsequent development of drugs that can control the extent of this activation. There are many diseases in which such drugs can be of great help. Amongst others, acute hepatitis in which the acute damage to the liver seems to reflect FAS-R ligand-mediated death of the liver cells; autoimmune-induced cell death such as the death of the β Langerhans cells of the pancreas, that results in diabetes; the death of cells in graft rejection (e.g., kidney, heart and liver); the death of oligodendrocytes in the brain in multiple sclerosis; and AIDS-inhibited T cell suicide which causes proliferation of the AIDS virus and hence the AIDS disease.

As mentioned hereinabove, it is possible that G1 or one or more of its possible isoforms (e.g. the G1β isoform) may serve as "natural" inhibitors of the G1 protease or G1 protease isoforms, and these may thus be employed as the above noted specific inhibitors of these G1 proteases. Likewise, other substances such as peptides, organic compounds, antibodies, etc. may also be screened to obtain specific drugs which are capable of inhibiting the G1 proteases.

A non-limiting example of how peptide inhibitors of the G1 proteases would be designed and screened is based on previous studies on peptide inhibitors of ICE or ICE-like proteases, the substrate specificity of ICE and strategies for epitope analysis using peptide synthesis. The minimum requirement for efficient cleavage of peptide by ICE was found to involve four amino acids to the left of the cleavage site with a strong preference for aspartic acid in the $P_1$ position and with methylamine being sufficient to the right of the $P_1$ position (Sleath et al., 1990; Howard et al., 1991; Thornberry et al., 1992). Furthermore, the fluorogenic substrate peptide (a tetrapeptide), acetyl-Asp-Glu-Val-Asp-a-(4-methyl-coumaryl-7-amide) abbreviated Ac-DEVD-AMC (SEQ ID NO:10), corresponds to a sequence in poly (ADP-ribose) polymerase (PARP) found to be cleaved in cells shortly after FAS-R stimulation, as well as other apoptopic processes (Kaufmann, 1989; Kaufmann et al., 1993; Lazebnik et al., 1994), and is cleaved effectively by CPP32 (a member of the CED3/ICE protease family) and MACH proteases (and likewise also possibly by G1 proteases).

As Asp in the $P_1$ position of the substrate appears to be important, tetrapeptides having Asp as the fourth amino acid residue and various combinations of amino acids in the first three residue positions can be rapidly screened for binding to the active site of G1 proteases using, for example, the method developed by Geysen (Geysen, 1985; Geysen et al., 1987) where a large number of peptides on solid supports were screened for specific interactions with antibodies. The binding of MACH proteases to specific peptides can be detected by a variety of well known detection methods within the skill of those in the art, such as radiolabeling of the G1 proteases, etc. This method of Geysen's was shown to be capable of testing at least 4000 peptides each working day.

Since it may be advantageous to design peptide inhibitors that selectively inhibit G1 proteases without interfering with physiological cell death processes in which other members of the CED3/ICE family of proteases are involved, the pool of peptides binding to G1 proteases in an assay such as the one described above can be further synthesized as a fluorogenic substrate peptide to test for selective cleavage by G1 proteases without being cleaved by other CED3/ICE proteases. Peptides which are determined to be selectively cleaved by the G1 proteases, can then be modified to enhance cell permeability and inhibit the cell death activity of G1 either reversibly or irreversibly. Thornberry et al. (1994) reported that a tetrapeptide (acyloxy) methyl ketone Ac-Tyr-Val-Ala-Asp-$CH_2OC$ (O)-[2,6-$(CF_3)_2$] Ph (SEQ ID NO:11) was a potent inactivator of ICE. Similarly, Milligan et al. (1995) reported that tetrapeptide inhibitors having a chloromethylketone (irreversibly) or aldehyde (reversibly) groups inhibited ICE. In addition, a benzyloxycarboxyl-Asp-$CH_2OC$ (O)-2,6-dichlorobenzene (DCB) was shown to inhibit ICE (Mashima et al., 1995). Accordingly, tetrapeptides that selectively bind to G1 proteases can be modified with, for example, an aldehyde group, chloromethylketone, (acyloxy) methyl ketone or a $CH_2OC$ (O)-DCB group to create a peptide inhibitor of G1 protease activity.

While some specific inhibitors of other CED3/ICE proteases are cell permeable, the cell permeability of peptide inhibitors may need to be enhanced. For instance, peptides can be chemically modified or derivatized to enhance their permeability across the cell membrane and facilitate the transport of such peptides through the membrane and into the cytoplasm. Muranishi et al. (1991) reported derivatizing thyrotropin-releasing hormone with lauric acid to form a lipophilic lauroyl derivative with good penetration characteristics across cell membranes. Zacharia et al. (1991) also reported the oxidation of methionine to sulfoxide and the replacement of the peptide bond with its ketomethylene isoester ($COCH_2$) to facilitate transport of peptides through the cell membrane. These are just some of the known modifications and derivatives that are well within the skill of those in the art.

Furthermore, drug or peptide inhibitors, which are capable of inhibiting the cell death activity of G1 or its possible isoforms can be conjugated or complexed with molecules that facilitate entry into the cell.

U.S. Pat. No. 5,149,782 discloses conjugating a molecule to be transported across the cell membrane with a membrane blending agent such as fusogenic polypeptides, ion-channel forming polypeptides, other membrane polypeptides, and long chain fatty acids, e.g. myristic acid, palmitic acid. These membrane blending agents insert the molecular conjugates into the lipid bilayer of cellular membranes and facilitate their entry into the cytoplasm.

Low et al., U.S. Pat. No. 5,108,921, reviews available methods for transmembrane delivery of molecules such as, but not limited to, proteins and nucleic acids by the mechanism of receptor mediated endocytotic activity. These receptor systems include those recognizing galactose, mannose, mannose 6-phosphate, transferrin, asialoglycoprotein, transcobalamin (vitamin $B_{12}$), α-2 macroglobulins, insulin and other peptide growth factors such as epidermal growth factor (EGF). Low et al. teaches that nutrient receptors, such as receptors for biotin and folate, can be advantageously used to enhance transport across the cell membrane due to the location and multiplicity of biotin and folate receptors on the membrane surfaces of most cells and the associated receptor mediated transmembrane transport processes. Thus, a complex formed between a compound to be delivered into the cytoplasm and a ligand, such as biotin or folate, is contacted with a cell membrane bearing biotin or folate receptors to initiate the receptor mediated trans-membrane transport mechanism and thereby permit entry of the desired compound into the cell.

ICE is known to have the ability to tolerate liberal substitutions in the $P_2$ position and this tolerance to liberal substitutions was exploited to develop a potent and highly selective affinity label containing a biotin tag (Thornberry et al., 1994). Consequently, the $P_2$ position as well as possibly the N-terminus of the tetrapeptide inhibitor can be modified or derivatized, such as to with the addition of a biotin molecule, to enhance the permeability of these peptide inhibitors across the cell membrane.

In addition, it is known in the art that fusing a desired peptide sequence with a leader/signal peptide sequence to create a "chimeric peptide" will enable such a "chimeric peptide" to be transported across the cell membrane into the cytoplasm.

As will be appreciated by those of skill in the art of peptides, the peptide inhibitors of G1 proteolytic activity according to the present invention is meant to include peptidomimetic drugs or inhibitors, which can also be rapidly screened for binding to G1 protease to design perhaps more stable inhibitors.

It will also be appreciated that the same means for facilitating or enhancing the transport of peptide inhibitors across cell membranes as discussed above are also applicable to the G1 or its isoforms themselves as well as other peptides and proteins which exerts their effects intracellularly.

As regards the antibodies mentioned herein throughout, the term "antibody" is meant to include polyclonal antibodies, monoclonal antibodies (mAbs), chimeric antibodies, anti-idiotypic (anti-Id) antibodies to antibodies that can be labeled in soluble or bound form, as well as fragments thereof provided by any known technique, such as, but not limited to enzymatic cleavage, peptide synthesis or recombinant techniques.

Polyclonal antibodies are heterogeneous populations of antibody molecules derived from the sera of animals immunized with an antigen. A monoclonal antibody contains a substantially homogeneous population of antibodies specific to antigens, which populations contains substantially similar epitope binding sites. MAbs may be obtained by methods known to those skilled in the art. See, for example Kohler and Milstein, *Nature,* 256:495-497 (1975); U.S. Pat. No. 4,376,110; Ausubel et al., eds., Harlow and Lane ANTIBODIES: A LABORATORY MANUAL, Cold Spring Harbor Laboratory (1988); and Colligan et al., eds., Current Protocols in Immunology, Greene Publishing Assoc. and Wiley Interscience N.Y., (1992-1996), the contents of which references are incorporated entirely herein by reference. Such antibodies may be of any immunoglobulin class including IgG, IgM, IgE, IgA, GILD and any subclass thereof. A hybridoma producing a mAb of the present invention may be cultivated in vitro, in situ or in vivo. Production of high titers of mAbs in vivo or in situ makes this the presently preferred method of production.

Chimeric antibodies are molecules of which different portions are derived from different animal species, such as those having the variable region derived from a murine mAb and a human immunoglobulin constant region. Chimeric antibodies are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (Cabilly et al., *Proc. Natl. Acad. Sci. USA* 81:3273-3277 (1984); Morrison et al., *Proc. Natl. Acad. Sci. USA* 81:6851-6855 (1984); Boulianne et al., *Nature* 312:643-646 (1984); Cabilly et al., European Patent Application 125023 (published Nov. 14, 1984); Neuberger et al., *Nature* 314:268-270 (1985); Taniguchi et al., European Patent Application 171496. (published Feb. 19, 1985); Morrison et al., European Patent Application 173494 (published Mar. 5, 1986); Neuberger et al., PCT Application WO 8601533, (published Mar. 13, 1986); Kudo et al., European Patent Application 184187 (published Jun. 11, 1986); Sahagan et al., *J. Immunol.* 137:1066-1074 (1986); Robinson et al., International Patent Application No. WO8702671 (published May 7, 1987); Liu et al., *Proc. Natl. Acad. Sci USA* 84:3439-3443 (1987); Sun et al., *Proc. Natl. Acad. Sci USA* 84:214-218 (1987); Better et al., *Science* 240:1041-1043 (1988); and Harlow and Lane, ANTIBODIES:A LABORATORY MANUAL, supra. These references are entirely incorporated herein by reference.

An anti-idiotypic (anti-Id) antibody is an antibody which recognizes unique determinants generally associated with the antigen-binding site of an antibody. An Id antibody can be prepared by immunizing an animal of the same species and genetic type (e.g. mouse strain) as the source of the mAb to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference.

The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

Accordingly, mAbs generated against the G1 proteins, analogs, fragments or derivatives thereof, of the present invention may be used to induce anti-Id antibodies in suitable animals, such as BALB/c mice. Spleen cells from such immunized mice are used to produce anti-Id hybridomas secreting anti-Id mAbs. Further, the anti-Id mAbs can be coupled to a carrier such as keyhole limpet hemocyanin (KLH) and used to immunize additional BALB/c mice. Sera from these mice will contain anti-anti-Id antibodies that have the binding properties of the original mAb specific for an epitope of the above G1 protein, or analogs, fragments and derivatives thereof.

The anti-Id mAbs thus have their own idiotypic epitopes, or "idiotopes" structurally similar to the epitope being evaluated, such as GRB protein-a.

The term "antibody" is also meant to include both intact molecules as well as fragments thereof, such as, for example, Fab and F(ab')2, which are capable of binding antigen. Fab and F(ab')2 fragments lack the Fc fragment of intact antibody, clear more rapidly from the circulation, and may have less non-specific tissue binding than an intact antibody (Wahl et al., *J. Nucl. Med.* 24:316-325 (1983)).

It will be appreciated that Fab and F(ab')2 and other fragments of the antibodies useful in the present invention may be used for the detection and quantitation of the G1 protein according to the methods disclosed herein for intact antibody molecules. Such fragments are typically produced by proteolytic cleavage, using enzymes such as papain (to produce Fab fragments) or pepsin (to produce F(ab')2 fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies which may be evoked by other antigens.

The antibodies, including fragments of antibodies, useful in the present invention may be used to quantitatively or qualitatively detect the G1 protein in a sample or to detect presence of cells which express the G1 protein of the present invention. This can be accomplished by immunofluorescence techniques employing a fluorescently labeled antibody (see below) coupled with light microscopic, flow cytometric, or fluorometric detection.

The antibodies (or fragments thereof) useful in the present invention may be employed histologically, as in immunofluorescence or immunoelectron microscopy, for in situ detection of the G1 protein of the present invention. In situ detection may be accomplished by removing a histological specimen from a patient, and providing the labeled antibody of the present invention to such a specimen. The antibody (or fragment) is preferably provided by applying or by overlaying the labeled antibody (or fragment) to a biological sample. Through the use of such a procedure, it is possible to determine not only the presence of the G1 protein, but also its distribution on the examined tissue. Using the present invention, those of ordinary skill will readily perceive that any of wide variety of histological methods (such as staining procedures) can be modified in order to achieve such in situ detection.

Such assays for the G1 protein of the present invention typically comprises incubating a biological sample, such as a biological fluid, a tissue extract, freshly harvested cells such as lymphocytes or leukocytes, or cells which have been incubated in tissue culture, in the presence of a detectably labeled antibody capable of identifying the G1 protein, and detecting the antibody by any of a number of techniques well known in the art.

The biological sample may be treated with a solid phase support or carrier such as nitrocellulose, or other solid support or carrier which is capable of immobilizing cells, cell particles or soluble proteins. The support or carrier may then be washed with suitable buffers followed by treatment with a detectably labeled antibody in accordance with the present invention, as noted above. The solid phase support or carrier may then be washed with the buffer a second time to remove unbound antibody. The amount of bound label on said solid support or carrier may then be detected by conventional means.

By "solid phase support", "solid phase carrier", "solid support", "solid carrier", "support" or "carrier" is intended any support or carrier capable of binding antigen or antibodies. Well-known supports or carriers, include glass, polystyrene, polypropylene, polyethylene, dextran, nylon amylases, natural and modified celluloses, polyacrylamides, gabbros and magnetite. The nature of the carrier can be either soluble to some extent or insoluble for the purposes of the present invention. The support material may have virtually any possible structural configuration so long as the coupled molecule is capable of binding to an antigen or antibody. Thus, the support or carrier configuration may be spherical, as in a bead, cylindrical, as in the inside surface of a test tube, or the external surface of a rod. Alternatively, the surface may be flat such as a sheet, test strip, etc. Preferred supports or carriers include polystyrene beads. Those skilled in the art will know may other suitable carriers for binding antibody or antigen, or will be able to ascertain the same by use of routine experimentation.

The binding activity of a given lot of antibody, of the invention as noted above, may be determined according to well known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which an antibody in accordance with the present invention can be detectably labeled is by linking the same to an enzyme and used in an enzyme immunoassay (EIA). This enzyme, in turn, when later exposed to an appropriate substrate, will react with the substrate in such a manner as to produce a chemical moiety which can be detected, for example, by spectrophotometric, fluorometric or by visual means. Enzymes which can be used to detectably label the antibody include, but are not limited to, malate dehydrogenase, staphylococcal nuclease, delta-5-steroid isomeras, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6- phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactive labeling the antibodies or antibody fragments, it is possible to detect R-PTPase through the use of a radioimmunoassay (RIA). A good description of RIA may be found in Laboratory Techniques and Biochemistry in Molecular Biology, by Work, T. S. et al., North Holland Publishing Company, NY (1978) with particular reference to the chapter entitled "An Introduction to Radioimmune Assay and Related Techniques" by Chard, T., incorporated by reference herein. The radioactive isotope can be detected by such means as the use of a g counter or a scintillation counter or by autoradiography.

It is also possible to label an antibody in accordance with the present invention with a fluorescent compound. When the fluorescently labeled antibody is exposed to light of the proper wavelength, its presence can be then detected due to fluorescence. Among the most commonly used fluorescent labeling compounds are fluorescein isothiocyanate, rhodamine, phycoerythrine, pycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriamine pentaacetic acid (ETPA).

The antibody can also be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

An antibody molecule of the present invention may be adapted for utilization in an immunometric assay, also known as a "two-site" or "sandwich" assay. In a typical immunometric assay, a quantity of unlabeled antibody (or fragment of antibody) is bound to a solid support or carrier and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen from the sample by formation of a binary solid phase antibody-antigen complex. After a suitable incubation period, the solid support or carrier is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support or carrier through the unlabeled antibody, the solid support or carrier is washed a second time to remove the unreacted labeled antibody.

In another type of "sandwich" assay, which may also be useful with the antigens of the present invention, the so-called "simultaneous" and "reverse" assays are used. A simultaneous assay involves a single incubation step as the antibody bound to the solid support or carrier and labeled antibody are both added to the sample being tested at the same time. After the incubation is completed, the solid support or carrier is washed to remove the residue of fluid sample and uncomplexed labeled antibody. The presence of labeled antibody associated with the solid support or carrier is then determined as it would be in a conventional "forward" sandwich assay.

In the "reverse" assay, stepwise addition first of a solution of labeled antibody to the fluid sample followed by the addition of unlabeled antibody bound to a solid support or carrier after a suitable incubation period is utilized. After a second incubation, the solid phase is washed in conventional fashion to free it of the residue of the sample being tested and the solution of unreacted labeled antibody. The determination of labeled antibody associated with a solid support or carrier is then determined as in the "simultaneous" and "forward" assays.

The G1 proteins of the invention may be produced by any standard recombinant DNA procedure (see for example, Sambrook, et al., 1989 and Ansabel et al., 1987-1995, supra) in which suitable eukaryotic or prokaryotic host cells well known in the art are transformed by appropriate eukaryotic or prokaryotic vectors containing the sequences encoding for the proteins. Accordingly, the present invention also concerns such expression vectors and transformed hosts for the production of the proteins of the invention. As mentioned above, these proteins also include their biologically active analogs, fragments and derivatives, and thus the vectors encoding them also include vectors encoding analogs and fragments of these proteins, and the transformed hosts include those producing such analogs and fragments. The derivatives of these proteins, produced by the transformed hosts, are the derivatives produced by standard modification of the proteins or their analogs or fragments.

The present invention also relates to pharmaceutical compositions comprising recombinant animal virus vectors encoding the G1 proteins, which vector also encodes a virus surface protein capable of binding specific target cell (e.g., cancer cells) surface proteins to direct the insertion of the G1 protein sequences into the cells. Further pharmaceutical compositions of the invention comprises as the active ingredient (a) an oligonucleotide sequence encoding an anti-sense sequence of the G1 protein sequence, or (b) drugs that block the proteolytic activity of G1 or its isoforms.

Pharmaceutical compositions according to the present invention include a sufficient amount of the active ingredient to achieve its intended purpose. In addition, the pharmaceutical compositions may contain suitable pharmaceutically acceptable carriers comprising excipients and auxiliaries which facilitate processing of the active compounds into preparations which can be used pharmaceutically and which can stabilize such preparations for administration to the subject in need thereof as well known to those of skill in the art.

The G1 protein and its isoforms or isotypes are suspected to be expressed in different tissues at markedly different levels and apparently also with different patterns of isotypes in an analogous fashion to the expression of MACH protein and its various isotypes as indicated in the above listed co-owned co-pending patent applications. These differences may possibly contribute to the tissue-specific features of response to the Fas/APO1-ligand and TNF. As in the case of other CED3/ICE homologs (Wang et al., 1994; Alnemri et al., 1995), the present inventors have previously shown (in the above mentioned patent applications) that MACH isoforms that contain incomplete CED3/ICE regions (e.g., MACHα3) are found to have an inhibitory effect on the activity of co-expressed MACHα1 or MACHα2 molecules; they are also found to block death induction by Fas/APO1 and p55-R. Expression of such inhibitory isoforms in cells may constitute a mechanism of cellular self-protection against Fas/APO1- and TNF-mediated cytotoxicity. An analogous inhibitory effect of at least some G1 isoforms is thus suspected. The wide heterogeneity of MACH isoforms, and likewise the suspected, analogous heterogeneity of G1 isoforms, which greatly exceeds that observed for any of the other proteases of the CED3/ICE family, should allow a particularly fine tuning of the function of the active MACH isoforms, and by analogy also the active G1 isoforms in accordance with the present invention.

It is also possible that some of the possible G1 isoforms serve other functions. For example, the previously found (present inventors as noted above) ability of MACHβ1 to bind to both MORT1 and MACHα1 suggests that this isoform could actually enhance the activity of the enzymatically active isoforms. The mild cytotoxicity observed in 293-EBNA and MCF7 cultures transfected with this isoform and the rather significant cytotoxic effect that it exerts in HeLa cells are likely to reflect activation of endogenously-expressed MACHα molecules upon binding to the transfected MACHβ1 molecules. Conceivably, some of the MACH isoforms could also act as docking sites for molecules that are involved in other, non-cytotoxic effects of Fas/APO1 and TNF receptors. Hence, in an analogous fashion G1 and/or its isoforms may also have such enhancing activities or serve as docking sites for other such molecules.

Due to the unique ability of Fas/APO1 and TNF receptors to cause cell death, as well as the ability of the TNF receptors to trigger other tissue-damaging activities, aberrations in the function of these receptors could be particularly deleterious to the organism. Indeed, both excessive and deficient functioning of these receptors have been shown to contribute to pathological manifestations of various diseases (Vassalli, 1992; Nagata and Golstein, 1995). Identifying the molecules that participate in the signaling activity of the receptors, and finding ways to modulate the activity of these molecules, could direct new therapeutic approaches. In view of the suspected central role of G1 in Fas/APO1- and TNF-mediated toxicity, it seems particularly important to design drugs that can block the possible proteolytic function of G1, as was done for some other proteins of the CED3/ICE family (Thornberry et al., 1994; Miller et al., 1995; Mashima et al., 1995; Milligan et al., 1995; Enari et al., 1995; Los et al., 1995). The unique sequence features of the CED3/ICE homolog apparently existing within G1 molecules could permit the design of drugs that would specifically affect its activity. Such drugs could provide protection from excessive immune-mediated cytotoxicity involving G1, without interfering with the physiological cell-death processes in which other members of the CED3/ICE family are involved.

Other aspects of the invention will be apparent from the following examples.

The invention will now be described in more detail in the following non-limiting examples and the accompanying drawings.

It should also be noted that the procedures of:
i) two-hybrid screen and two-hybrid β-galactosidase expression test; (ii) induced expression, metabolic labeling and immunoprecipitation of proteins; (iii) in vitro binding; (iv) assessment of the cytotoxicity; and (v) Northern and sequence analyses, as set forth in Reference Examples 1 (see also Boldin et al., 1995b) 2, and 3 (see also Boldin et al., 1996) below, with respect to MORT-1 and a MORT-1 binding protein, (e.g. MACH), respectively, are equally applicable (with some modifications) for the corresponding isolation, cloning and characterization of G1 and its possible isoforms of the present invention. These procedures are thus to be construed as the full disclosure of the same procedures used for the isolation, cloning and characterization of G1 in accordance with the present invention, as detailed in Example 1 below. (Reference Examples 1-3 below also appear in the same or equivalent form in the co-owned co-pending Israel Application Nos. 114,615, 114,986, 115,319, 116588, and 117,932, as well as the corresponding PCT application No. PCT/US96/10521). Moreover, in the above section entitled 'Brief Description of the Drawings' there is also included some details of the experimental procedures carried out in accordance with the present invention and these form part of Example 1 below with respect to the full disclosure of the present invention and hance should be considered together with the disclosure in Example 1.

REFERENCE EXAMPLE 1

Cloning and Isolation of the MORT-1 Protein Which Binds to the Intracellular Domain of the FAS-R (i) Two-hybrid Screen and Two-hybrid β-Galactosidase Expression Test To isolate proteins interacting with the intracellular domain of the FAS-R, the yeast two-hybrid system was used (Fields and Song, 1989). Briefly, this two-hybrid system is a yeast-based genetic assay to detect specific protein-protein interactions in vivo by restoration of a eukaryotic transcriptional activator such as GAL4 that has two separate domains, a DNA binding and an activation domain, which domains when expressed and bound together to form a restored GAL4 protein, is capable of binding to an upstream activating sequence which in turn activates a promoter that controls the expression of a reporter gene, such as lacZ or HIS3, the expression of which is readily observed in the cultured cells. In this system, the genes for the candidate interacting proteins are cloned into separate expression vectors. In one expression vector, the sequence of the one candidate protein is cloned in phase with the sequence of the GAL4 DNA-binding domain to generate a hybrid protein with the GAL4 DNA-binding domain, and in the other vector, the sequence of the second candidate protein is cloned in phase with the sequence of the GAL4 activation domain to generate a hybrid protein with the GAL4-activation domain. The two hybrid vectors are then co-transformed into a yeast host strain having a lacZ or HIS3 reporter gene under the control of upstream GAL4 binding sites. Only those transformed host cells (cotransformants) in which the two hybrid proteins are expressed and are capable of interacting with each other, will be capable of expressing the reporter gene. In the case of the lacZ reporter gene, host cells expressing this gene will become blue in color when X-gal is added to the cultures. Hence, blue colonies are indicative of the fact that the two cloned candidate proteins are capable of interacting with each other.

Using this two-hybrid system, the intracellular domain, FAS-IC, was cloned, separately, into the vector pGBT9 (carrying the GAL4 DNA-binding sequence, provided by CLONTECH, USA, see below), to create fusion proteins with the GAL4 DNA-binding domain. For the cloning of FAS-R into pGBT9, a clone encoding the full-length cDNA sequence of FAS-R (WO 9531544) was used from which the intracellular domain (IC) was excised by standard procedures using various restriction enzymes and then isolated by standard procedures and inserted into the pGBT9 vector, opened in its multiple cloning site region (MCS), with the corresponding suitable restriction enzymes. It should be noted that the FAS-IC extends from amino acid residues 175-319 of the intact FAS-R, this portion containing residues 175-319 being the FAS-IC inserted into the pGBT9 vector.

The above hybrid (chimeric) vector was then cotransfected together with a cDNA library from human HeLa cells cloned into the pGAD GH vector, bearing the GAL4 activating domain, into the HF7c yeast host strain (all the above-noted vectors, pGBT9 and pGAD GH carrying the HeLa cell cDNA library, and the yeast strain were purchased from Clontech Laboratories, Inc., USA, as a part of MATCHMAKER Two-Hybrid System, #PT1265-1). The co-transfected yeasts were selected for their ability to grow in medium lacking Histidine (His⁻ medium), growing colonies being indicative of positive transformants. The selected yeast clones were then tested for their ability to express the lacZ gene, i.e., for their LACZ activity, and this by adding X-gal to the culture medium, which is catabolized to form a blue colored product by β-galactosidase, the enzyme encoded by the lacZ gene. Thus, blue colonies are indicative of an active lacZ gene. For activity of the lacZ gene, it is necessary that the GALA transcription activator be present in an active form in the transformed clones, namely that the GAL4 DNA-binding domain encoded by the above hybrid vector be combined properly with the GAL4 activation domain encoded by the other hybrid vector. Such a combination is only possible if the two proteins fused to each of the GAL4 domains are capable of stably interacting (binding) to each other. Thus, the His⁺ and blue (LACZ⁺) colonies that were isolated are colonies which have been cotransfected with a vector encoding FAS-IC and a vector encoding a protein product of human HeLa cell origin that is capable of binding stably to FAS-IC.

The plasmid DNA from the above His⁺, LACZ⁺ yeast colonies was isolated and electroporated into *E. coli* strain HB101 by standard procedures followed by selection of Leu⁺ and Ampicillin resistant transformants, these transformants being the ones carrying the hybrid pGAD GH vector which has both the Amp$^R$ and Leu2 coding sequences. Such transformants therefore are clones carrying the sequences encoding newly identified proteins capable of binding to the FAS-IC. Plasmid DNA was then isolated from these transformed *E. coli* and retested by:

(a) retransforming them with the original FAS-R intracellular domain hybrid plasmid (hybrid pGTB9 carrying the FAS-IC) into yeast strain HF7 as set forth hereinabove. As controls, vectors carrying irrelevant protein encoding sequences, e.g., pACT-lamin or pGBT9 alone were used for cotransformation with the FAS-IC-binding protein (i.e., MORT-1)-encoding plasmid. The cotransformed yeasts were then tested for growth on His⁻ medium alone, or with different levels of 3-aminotriazole; and (b) retransforming the plasmid DNA and original FAS-IC hybrid plasmid and control plasmids described in (a) into yeast host cells of strain SFY526 and determining the LACZ⁺ activity (effectivity of β-gal formation, i.e., blue color formation).

The results of the above tests revealed that the pattern of growth of colonies in His⁻ medium was identical to the pattern of LACZ activity, as assessed by the color of the colony, i.e., His⁺ colonies were also LACZ⁺. Further, the LACZ activity in liquid culture (preferred culture conditions) was assessed after transfection of the GAL4 DNA-binding and activation-domain hybrids into the SFY526 yeast hosts which have a better LACZ inducibility with the GAL4 transcription activator than that of the HF7 yeast host cells.

Using the above procedure, a protein previously designated HF1, and now referred to as MORT-1 for "Mediator of Receptor-induced Toxicity", was identified, isolated and characterized.

Furthermore, it should also be mentioned that in a number of the above two-hybrid β-galactosidase expression tests, the expression of β-galactosidase was also assessed by a preferred filter assay. In the screening, five of about $3 \times 10^6$ cDNAs were found to contain the MORT-1 insert. The so-isolated cloned MORT-1 cDNA inserts were then sequenced using standard DNA sequencing procedures. The amino acid sequence of MORT-1 was deduced from the DNA sequence (for the MORT-1 DNA and amino acid sequences, see co-owned, co-pending Israel Application Nos. 112,022, 112, 692, and 114,615 and their corresponding PCT application No. WO96/18641). Residue numbering in the proteins encoded by the cDNA inserts are as in the Swiss-Prot data bank. Deletion mutants were produced by PCR, and point mutants by oligonucleotide-directed mutagenesis (Current Protocols in Molec. Biol., 1994).

(ii) Induced Expression, Metabolic Labeling and Immunoprecipitation of Proteins

MORT-1, N-linked to the FLAG octapeptide (FLAG-MORT-1; Eastman Kodak, New Haven, Conn., USA), Fas-IC, FAS-R, p55-R, a chimera comprised of the extracellular domain of p55-R (amino acids 1-168) fused to the transmembrane and intracellular domain of FAS-R (amino acids 153-319), and the luciferase cDNA which serves as a control, were expressed in HeLa cells. Expression was carried out using a tetracycline-controlled expression vector, in a HeLa cell clone (HtTA-1) that expresses a tetracycline-controlled transactivator (Gossen and Bujard, 1992; see also Boldin et al., 1995). Metabolic labeling with [$^{35}$S]methionine and [$^{35}$S]cysteine (DUPONT, Wilmington, Del., USA and Amersham, Buckinghamshire, England) was performed 18 hours after transfection, by a further 4 h incubation at 37° C. in Dulbecco's modified Eagle's medium lacking methionine and cysteine, but supplemented with 2% dialyzed fetal calf serum. The cells were then lysed in RIPA buffer (10 mM Tris-HCl, pH 7.5, 150 mM NaCl, 1% NP-40, 1% deoxycholate, 0.1% SDS and 1 mM EDTA) and the lysate was precleared by incubation with irrelevant rabbit antiserum (3 μl/ml) and Protein G Sepharose beads (Pharmacia, Uppsala, Sweden; 60 μl/ml). Immunoprecipitation was performed by 1 h incubation at 4° C. of 0.3 ml aliquots of lysate with mouse monoclonal antibodies (5 μl/aliquot) against the FLAG octopeptide (M2; Eastman Kodak), p55-R (#18 and #20; Engelmann et al., 1990), or FAS-R (ZB4; Kamiya Southand Oaks, Calif., USA), or with isotype matched mouse antibodies as a control, followed by a further 1 h incubation with Protein G Sepharose beads (30 μl/aliquot).

(iii) In Vitro Binding

Glutathione S-transferase (GST) fusions with the wild type or a mutated Fas-IC were produced and adsorbed to glutathione-agarose beads; see Boldin et al., 1995; Current Protocols in Molecular Biology, 1994; Frangioni and Neel, 1993). Binding of metabolically-labeled FLAG-MORT-1 fusion protein to GST-Fas-IC was assessed by incubating the beads for 2 h at 4° C. with extracts of HeLa cells, metabolically labeled with [$^{35}$S]methionine (60 μCi/ml), that express FLAG-MORT-1. The extracts were prepared in a buffer containing 50 mM Tris-HCl, pH 7.5, 150 mM NaCl, 0.1% NP-40, 1 mM dithiotreitol, 1 mM EDTA, 1 mM phenylmethylsulfonyl fluoride, 20 μg/ml Aprotonin, 20 μg/ml Leupeptin, 10 mM sodium fluoride and 0.1 mM sodium vanadate (1 ml per $5 \times 10^5$ cells).

(iv) Assessment of the Cytotoxicity Triggered by Induced Expression of MORT-1

MORT-1, Fas-IC, p55-IC and luciferase cDNAs were inserted into a tetracycline-controlled expression vector and transfected to HtTA-1 cells (a HeLa cell line) (Gossen and Bujard, 1992) together with the secreted placental alkaline phosphatase cDNA, placed under control of SV40 promoter (the pSBC-2 vector, Dirks et al., 1993). Cell death was assessed 40 hours after transfection, either by the neutral-red uptake assay (Wallach, 1984) or, for assessing specifically the death in those cells that express the transfected cDNAs, by determining the amounts of placental alkaline phosphatase (Berger et al., 1988) secreted to the growth medium at the last 5 hours of incubation.

In another set of experiments to analyze the region of the MORT-1 protein involved in the binding to the FAS-IC, the following proteins were expressed transiently in HeLa cells that contain a tetracycline-controlled transactivator (HtTA-1), using a tetracycline-controlled expression vector (pUHD10-3): Human FAS-R alone; Human FAS-R as well as the N-terminal part of MORT-1 (amino acids 1-117, the "MORT-1 head"); Human FAS-R as well as the C-terminal part of MORT-1, which contains its 'death domain' homology region (amino acids 130-245, the "MORT-1 DD"); FLAG-55.11 (amino acids 309-900 of protein 55.11 fused at the N-terminus to the FLAG octapeptide, the protein 55.11 being a p55-IC-specific binding protein. Twelve hours after transfection, the cells were trypsinized and re-seeded at a concentration of 30,000 cells/well. After 24 hrs further incubation, the cells were treated for 6 hrs with a monoclonal antibody against the extracellular domain of FAS-R (monoclonal antibody CH-11, Oncor, Gaithersburg, Md., USA) at various concentrations (0.001-10 μg/ml monoclonal antibody), in the presence of 10 μg/ml cycloheximide. Cell viability was then determined by the neutral-red uptake assay and the results were presented in terms of % viable cells as compared to cells that had been incubated with cycloheximide alone (in the absence of anti-FAS-R monoclonal antibody CH-11).

(v) Northern and Sequence Analyses

Poly A$^+$ RNA was isolated from total RNA of HeLa cells (Oligotex-dT mRNA kit. QIAGEN, Hilden, Germany). Northern analysis using the MORT-1 cDNA as a probe was performed by conventional methods (see Boldin et al., 1995). The nucleotide sequence of MORT-1 was determined in both directions by the dideoxy chain termination method.

Sequence analysis of the MORT-1 cDNA cloned by the two-hybrid procedure indicated that it encodes a novel protein. Applying the two-hybrid test further to evaluate the specificity of the binding of this protein (MORT-1 for "Mediator of Receptor-induced Toxicity") to Fas-IC, and to define the particular region in Fas-IC to which it binds, led to the following findings: (a) The MORT-1 protein binds both to human and to mouse Fas-IC, but not to several other tested proteins, including three receptors of the TNF/NGF receptor family (p55 and p75 TNF receptors and CD40); (b) Replacement mutations at position 225 (Ile) in the 'death domain' of FAS-R, shown to abolish signaling both in vitro and in vivo (the lpr$^{cg}$ mutation (Watanabe-Fukunaga et al., 1992; Itoh and Nagata, 1993), also prevents binding of MORT-1 to the FAS-IC; (c) The MORT-1 binding-site in FAS-R occurs within the 'death domain' of this receptor; and (d) MORT-1 binds to itself. This self-binding, and the binding of MORT-1 to FAS-R involve different regions of the protein: A fragment of MORT-1 corresponding to residues 1-117 binds to the full-length MORT-1, but does not bind to itself nor to the FAS-IC. Conversely, a fragment corresponding to residues 130-245 binds to FAS-R, yet does not bind to MORT-1. Furthermore, it also arose from the results that the 'death domain' region of FAS-R is critical for FAS-IC self-association, as is the 'death domain' region of p55-R for p55-IC self-association. The deletions on both sides of these 'death domains' does not affect the self-association ability thereof while, however, a deletion within these 'death domains' does affect the self-association. In the case of MORT-1, the binding of MORT-1 to FAS-IC is also dependent upon the complete (fill) 'death domain' of FAS-R, while however, it is also not dependent on the regions outside of the FAS-R 'death domain' region for FAS-IC binding.

The interaction of the proteins encoded by the Gal4 DNA binding domain and activation-domain constructs (pGBT9 and pGAD-GH) within transfected SFY526 yeasts was assessed by β-galactosidase expression filter assay. The DNA-binding-domain constructs included four constructs of the human Fas-IC, four constructs of the mouse Fas-IC including two full-length constructs having Ile to Leu or Ile to Ala replacement mutations at position 225 (I225N and I225A, respectively), and three MORT-1 constructs. The activation-domain constructs included three MORT-1 constructs, the MORT-1 portion being as in the DNA-binding-domain constructs; and a full-length human Fas-IC construct, the Fas-IC portion being the same as in the above DNA-binding domain construct. The intracellular domains of human p55 TNF receptor (p55-IC residues 206-426), human CD40 (CD40-IC, residues 216-277) and human p75 TNF receptor (p75-IC, residues 287-461) as well as lamin, cyclin D and "empty" Gal4 (pGBT9) vectors served as negative controls in the form of DNA-binding domain constructs. SNF-1 and SNF4 served as positive controls in the form of DNA-binding-domain (SNF1) and activation-domain (SNF4) constructs. "Empty" Gal4 vectors (pGAD-GH) also served as negative controls in the form of activation domain constructs. The symbols "++" and "+" used in the presentation of the results of the above analysis denote the development of strong color within 30 and 90 min of the assay, respectively; and "–" denotes no development of color within 24 h.

Expression of MORT-1 molecules fused at their N-terminus with the FLAG octapeptide (FLAG-MORT-1) yielded in HeLa cells proteins of four distinct sizes—about 27, 28, 32, and 34 kD. The interaction of MORT-1 with Fas-IC in vitro was observed by performing an immunoprecipitate of proteins from extracts of HeLa cells transfected with the FLAG-MORT-1 fusion protein or with luciferase cDNA as a control, the immunoprecipitation being performed with anti-FLAG antibody (aFLAG). The interaction in vitro was also demonstrated between MORT-1 and FAS-IC wherein MORT-1 is in the form of [$^{35}$S] methionine-metabolically labeled FLAG-MORT-1 fusion proteins obtained from extracts of transfected HeLa cells and FAS-IC is in the form of human and mouse GST-FAS-IC fusion proteins including one having a replacement mutation at position 225 in FAS-IC, all of which GST-FAS-IC fusion proteins were produced in *E. coli*. The GST-fusion proteins were attached to glutathione beads before interaction with the extracts containing the MORT-1-FLAG fusion protein following this interaction, SDS-PAGE was performed. Thus, the in vitro interaction was evaluated by assessing, by autoradiography following SDS-PAGE, the binding of [$^{35}$S] metabolically labeled MORT-1, produced in transfected HeLa cells as a fusion with the FLAG octapeptide (FLAG-MORT-1), to GST, GST fusion with the human or mouse Fas-IC (GST-huFas-IC, GST-mFas-IC) or to GST fusion with Fas-IC containing a Ile to Ala replacement mutation at position 225. It was shown that all four FLAG-MORT-1 proteins showed ability to bind to Fas-IC upon incubation with a GST-Fas-IC fusion protein. As in the yeast two-hybrid test, MORT-1 did not bind to a GST-Fas-IC fusion protein with a replacement at the lpr$^{cg}$ mutation site (I225A).

The proteins encoded by the FLAG-MORT-1 cDNA showed also an ability to bind to the intracellular domain of FAS-R, as well as to the intracellular domain of FAS-R chimera whose extracellular domain was replaced with that of p55-R (p55-FAS), when co-expressed with these receptors in HeLa cells. In this case, interaction of MORT-1 with FAS-IC in transfected HeLa cells, i.e., in vivo, as observed with immunoprecipitates of various transfected HeLa cells demonstrated the in vivo interaction and specificity of the interaction between MORT-1 and FAS-IC in cells co-transfected with constructs encoding these proteins. Thus, FLAG-MORT-1 fusion protein was expressed and metabolically labeled with [$^{35}$S] cystein (20 μCi/ml) and [$^{35}$S]methionine (40 μCi/ml) in HeLa cells, alone, or together with human FAS-R, FAS-R chimera in which the extracellular domain of FAS-R was replaced with the corresponding region in the human p55-R (p55-FAS), or the human p55-R, as negative control. Cross immunoprecipitation of MORT-1 with the co-expressed receptor was performed using various specific antibodies. The results indicated that, FLAG-MORT-1 is capable of binding to the intracellular domain of FAS-R, as well as to the intracellular domain of a FAS-R-p55-R chimera having the extracellular domain of p55-R and the intracellular domain of FAS-R, when co-expressed with these receptors in the HeLa cells. Further, immunoprecipitation of FLAG-MORT-1 from extracts of the transfected cells also resulted in precipitation of the co-expressed FAS-R or the co-expressed p55-FAS chimera. Conversely, immunoprecipitation of these receptors resulted in the coprecipitation of the FLAG-MORT-1.

Northern analysis using the MORT-1 cDNA as probe revealed a single hybridizing transcript in HeLa cells. In a Northern blot in which poly A$^+$ RNA (0.3 μg) from transfected cells was hybridized with MORT-1 cDNA, the size of the RNA transcript (about 1.8 kb) was found to be close to the size of the MORT-1 cDNA (about 1702 nucleotides).

In sequence analysis, the cDNA was found to contain an open reading frame of about 250 amino acids. In the above co-owned co-pending applications, the MORT-1 DNA and amino acid sequences are shown (see WO96/18641). In these sequences the 'death domain' motif is underlined, as is a possible start Met residue (position 49; bold, underlined M) and the translation stop codon (the asterik under the codon at position 769-771). This 'death domain' motif shares homology with the known p55-R and FAS-R 'death domain' motifs (p55DD and FAS-DD). In order to determine the precise C-terminal end of MORT-1 and to obtain evidence concerning the precise N-terminal (initial Met residue) end of MORT-1, additional experiments were carried out as follows:

Using the methods described above, a number of constructs encoding MORT-1 molecules fused at their N-terminus with the FLAG octapeptide (FLAG-MORT-1) were constructed and expressed in HeLa cells with metabolic labeling of the expressed proteins using $^{35}$S-cysteine and $^{35}$S-methionine. The MORT-1-FLAG molecules were encoded by the following cDNAs containing different portions of the MORT-1-encoding sequence:
i) The FLAG octapeptide cDNA linked to the 5' end of the MORT-1 cDNA from which nucleotides 1-145 were deleted;
ii) The FLAG octapeptide cDNA linked to the 5' end of the MORT-1 full length cDNA;
iii) The FLAG octapeptide cDNA linked to the 5' end of the MORT-1 cDNA from which nucleotides 1-145 as well as nucleotides 832-1701 were deleted and the codon GCC at position 142-144 was mutated to TCC to prevent start of translation at this site.

Following expression of the above FLAG-MORT-1 fusion products, immunoprecipitation was carried out as mentioned above, using either anti-FLAG monoclonal antibodies or as a control, anti-p75 TNF-R antibodies, followed by SDS-PAGE (10% acrylamide) and autoradiography. The results of the analysis with the above FLAG-MORT-1 fusion products confirmed (validated) the C-terminal end of MORT-1 and provided evidence that the N-terminal end of MORT-1 may be at position 49 of the sequence.

Indeed, it has been shown by additional expression experiments of MORT-1 without the FLAG octapeptide fused to its 5'-end, that Met$^{49}$ serves as an effective site of translation initiation.

A search conducted in the 'Gene Bank' and 'Protein Bank' DataBases revealed that at the time, there was no sequence corresponding to that of the above isolated MORT-1 sequence. Thus, MORT-1 represented a new FAS-IC-specific binding protein.

High expression of p55-IC results in triggering of a cytocidal effect (Boldin et al., 1995). The expression of Fas-IC in HeLa cells also has such an effect, though to a lower extent, which could be detected only with the use of a sensitive assay. The ligand independent triggering of cytocidal effects in cells transfected with MORT-1, as well as human p55-IC and FAS-IC, was thus analyzed. The effect of transient expression of MORT-1, human Fas-IC, human p55-IC, or luciferase that served as a control, on the viability of HeLa cells was assessed using a tetracycline-controlled expression vector. Cell viability was evaluated 40 min after transfecting these cDNAs either in the presence or absence of tetracycline (1 μg/ml, to block expression), together with a cDNA encoding the secreted placental alkaline phosphatase. Cell viability was determined either by the neutral red uptake assay or, for determining specifically the viability of those particular cells that express the transfected DNA, by measuring the amounts of placental alkaline phosphatase secreted to the growth medium.

The above analysis revealed that the expression of MORT-1 in HeLa cells resulted in significant cell death, greater than that caused by FAS-IC expression. These cytotoxic effects of all of p55-IC, FAS-IC and MORT-1 seem to be related to the 'death domain' regions, present in all of these proteins, which 'death domains' have a propensity to self-associate, and thereby possibly prompting the cytotoxic effects.

In view of the above mentioned characteristics of MORT-1, namely, the specific association of MORT-1 with that particular region in FAS-R which is involved in cell death induction, and the fact that even a slight change of structure in that region, which prevents signaling (the lpr$^{cg}$ mutation) abolishes also the binding of MORT-1, indicates that this protein plays a role in the signaling or triggering of cell death. This notion is further supported by the observed ability of MORT-1 to trigger by itself a cytocidal effect. Thus, MORT-1 may function as (i) a modulator of the self-association of FAS-R by its own ability to bind to FAS-R as well as to itself, or (ii) serve as a docking site for additional proteins that are involved in the FAS-R signaling, i.e., MORT-1 may be a 'docking' protein and may therefore bind other receptors besides FAS-R, or (iii) constitutes part of a distinct signaling system that interacts with FAS-R signaling.

In order to further analyze the regions of MORT-1 involved in FAS-IC binding and modulation of the FAS-R-mediated cellular effects (cytotoxicity), the above-mentioned experiments were carried out, using vectors encoding portions of MORT-1 (the 'MORT-1 head', amino acids 1-117 and the 'MORT-1 dd', amino acids 130-245) (separately), with a vector encoding the human FAS-R for co-transfections of HeLa cells. In these experiments, the various proteins and combinations of proteins were expressed transiently in HeLa cells that contain a tetracycline-controlled transactivator (HtTA-1) by inserting the sequences encoding the proteins into a tetracycline-controlled expression vector pUHD10-3. Control transfections employed vectors encoding only the FAS-R and vectors encoding the FLAG-55.11 fusion protein (the 55.11 protein being a p55-IC-specific binding protein of which a portion containing amino acids 309-900 was fused (at its N-terminal) to the FLAG octapeptide).

Following the transfection and incubation periods, the transfected cells were treated with various concentrations of an anti-FAS-R monoclonal antibody (CH-11) which binds specifically to the extracellular domain of FAS-R expressed by cells. This binding of anti-FAS-R antibody induces the aggregation of the FAS-R at the cell surface (much like the FAS-R ligand) and induces the intracellular signaling pathway mediated by the FAS-IC, resulting, ultimately, in cell death (FAS-R mediated cell cytotoxicity). The concentrations of the anti-FAS-R monoclonal antibody (CH-11) used were in the range of 0.01-10 μg/ml, usually concentrations such as 0.005; 0.05; 0.5 and 5 μg/ml. The cells were treated with the anti-FAS antibody in the presence of 10 μg/ml cycloheximide.

The results of the above analysis show that the expression of FAS-R in the transfected cells conveys an increased sensitivity to the cytocidal effects of the anti-FAS-R antibodies. Further, the co-expression of the region in MORT-1 that contains the 'death domain' homology region and FAS-R strongly interferes with FAS-induced (i.e. FAS-R mediated) cell death as would be expected from the ability of the MORT-1 'death domain' (DD) region to bind to the FAS-R 'death domain' (FAS-DD). Moreover, co-expression of the N-terminal part of MORT-1 and FAS-R does not interfere with FAS-R-mediated cell death and, if at all, somewhat enhances the cytotoxicity (i.e., slightly increased cell death).

Thus, the above results clearly indicated that the MORT-1 protein has two distinct regions as far as binding to the FAS-IC and mediation of the cell-cytotoxic activity of the FAS-IC are concerned.

These results therefore also provide a basis for the use of different parts (i.e., active fragments or analogs) of the MORT-1 protein for different pharmaceutical applications. For example, the analogs or fragments or derivatives thereof of the MORT-1 protein which contain essentially only the C-terminal portion of MORT-1 inclusive of its 'death domain' region may be used for inhibiting FAS-R-mediated cytotoxic effects in FAS-R containing cells or tissues and thereby protect these cells or tissues from the deleterious effects of the FAS-R ligand in cases such as, for example, acute hepatitis. Alternatively, the analogs or fragments or derivatives thereof of the MORT-1 protein which contain essentially only the N-terminal portion of MORT-1 may be used for enhancing the FAS-R-mediated cytotoxic effects in FAS-R containing cells and tissues, thereby leading to the enhanced destruction of these cells or tissues when desired in cases such as, for example, tumor cells and autoreactive T and B cells. As detailed herein above, the above uses of the different regions of MORT-1 may be carried out using the various recombinant viruses (e.g., Vaccinia) to insert the MORT-1 region-encoding sequence into specific cells or tissues it is desired to treat.

Furthermore, it is also possible to prepare and use various other molecules such as, antibodies, peptides and organic molecules which have sequences or molecular structures corresponding to the above noted MORT-1 regions in order to achieve the same desired effects mediated by these MORT-1 regions.

Moreover, MORT-1 may be utilized to specifically identify, isolate and characterize other proteins which are capable of binding to MORT-1 (i.e., MORT-1-binding proteins); see Reference Examples 2 and 3.

REFERENCE EXAMPLE 2

Isolation of a MORT-1 Binding Protein (i) Two-hybrid Screen and Two-hybrid β-Galactosidase Expression Test In a manner analogous to the procedure described in Reference Example 1, using the intracellular domain of p55 TNF-R (p55 IC) and MORT-1 as baits, and screening a human B-cell library, two cDNA clones were obtained, which encode a protein product capable of binding to both MORT-1 and p55-IC. Both clones were shown to have identical nucleotide sequences at the 5' end (see co-owned, co-pending WO96/18641 and PCT/US96/10521).

(ii) Binding Properties of the Newly Cloned cDNA, in Two Hybrid Screens

Using the above-mentioned yeast two-hybrid procedure a construct containing the new MORT-1-binding protein cDNA was used as a "prey" to which were added constructs of a number of "baits" in separate reactions, to determine the binding specificity of the MORT-1-binding protein encoded by this cDNA. These "baits" included constructs encoding MORT-1, portions of MORT-1 (MORT 'head', aa1-117, MORT 'tail', aa 130-245), the p55 IC (206-426 p55) or portion thereof (the 'death domain', 326-426 p55; and others upstream of the 'death domain' i.e. 206-326). The results are shown below in Table 2.

TABLE 2

| Bait | β-galactosidase expression data |
|---|---|
| MORT-1 | +++ |
| 130-245 MORT-1 | + |
| 1-117 MORT-1 | − |
| 206-426 p55 | +++ |
| 326-426 p55 | +++ |
| 206-326 p55 | − |
| 206-308 p55 | − |
| 206-345 p55 | − |
| p55 L351NI | − |
| Fas IC | − |
| 233-319 Fas | − |
| p75 IC | − |
| CD40 IC | − |
| pGBT10 | − |
| SNF1 | − |
| Cycline D | − |
| Lamin | − |

The above results of the two-hybrid β-galactosidase expression test of the binding of the clone to a large panel of baits confirmed that the protein encoded by this clone binds specifically to the death domains of both the p55 TNF-R and MORT-1.

In general, the MORT-1 binding protein may be utilized directly to modulate or mediate the MORT-1 associated effects on cells, or, indirectly, to modulate or mediate the FAS-R ligand effect on cells when this effect is modulated or mediated by MORT-1. The same holds true with respect to other intracellular proteins or intracellular domains of transmembrane proteins, as specifically demonstrated for the p55 TNF-R herein.

MORT-1-binding proteins include those which bind specifically to the entire MORT-1 protein or those which bind to different regions of the MORT-1 protein, e.g., the above-noted N- and C-terminal regions of MORT-1. The MORT-1-binding proteins which bind specifically to such regions may be used to modulate the activity of these regions and hence the specific activity of MORT-1 as determined by these regions.

REFERENCE EXAMPLE 3

Isolation and Characterization of the MACH Protein, Another MORT-1 Binding Protein (i) Two-hybrid Screen, Two-hybrid β-Galactosidase Test, Sequencing and Sequence Analysis Using the procedure set forth in Reference Examples 1 and 2 above, a full length construct encoding human MORT-1 protein was employed as a "bait" in the yeast two-hybrid system to isolate a cDNA clone encoding an additional new MORT-1 binding protein. This new protein was originally designated MORT-2, and now redesignated and referred to as MACH (for MORT-1 associated CED3 homolog), by virtue of its characteristics as detailed herein below.

This cDNA clone was sequenced by standard procedures as set forth in Reference Examples 1 and 2 above. Sequence analysis by standard procedures and computer programs (see Reference Examples 1 and 2) revealed that this cDNA has a novel sequence and encodes a novel protein (neither the DNA nor the amino acid sequences was found in GENBANK or PROTEIN BANK sequence databases). Further, the cDNA encoding MACH revealed an ORF-B open reading frame which has strong homology to the region preceeding (5' upstream) the 'death domain' motif of the MORT-1 protein (see Reference Example 1). In co-owned co-pending Israel Application Nos. 114615, 114986, 115319, 116588 and 117932 as well as their corresponding PCT application No. PCT/US96/10521 there is shown the structure of that part of the MACH cDNA clone which contains ORF-B (235 aa residues); the deduced amino acid sequence of the MACH ORF-B; and the nucleotide sequence of the MACH cDNA molecule. A region of ORF-B shares high homology with the region of MORT-1 upstream of the MORT-1 'death domain" motif.

The yeast two-hybrid test was further applied to evaluate the specificity of binding of MACH to MORT-1, in particular, to define the region in MORT-1 to which MACH binds, as well as to determine which of the MACH ORFs interacts with MORT-1, the procedures being as set forth herein above in Reference Examples 1 and 2. Briefly, various MORT-1 and MACH constructs were prepared for testing the interaction of the proteins encoded by the Gal4 DNA-binding domain and activation domain constructs within transfected SFY526 yeast cells as assessed by the β-galactosidase expression filter assay. The DNA-binding domain constructs were prepared in pGBT9 vectors and the activation domain constructs were prepared in pGAD-GM vectors. For the activation domain constructs, the full-length MACH cDNA was used (MACH), as was a construct encoding only the ORF-B (MACH B) region. Control activation domain constructs were those containing the full-length MORT-1 coding sequence (MORT 1, positive control) and those having no inserts, i.e. "empty" vectors (pGAD-GM). For the DNA-binding domain constructs, the full-length MORT-1 cDNA was used (MORT 1), as were constructs encoding only the MORT-1 upstream region (MORT-1DD aa 130-245). Control DNA-binding domain constructs, which were constructed to determine also the specificity of the MACH binding, included constructs encoding lamin (Lamin), residues 287-461 of the intracellular domain of the human p75 TNF-R (human p75 IC), cyclic D (cycD), SNF1, residues 206-426 of the intracellular domain of the human p55 TNF-R (human p55 IC), the 'death domain' region of the intracellular domain of the human Fas-R (human Fas DD), residues 216-277 of the intracellular domain of the human CD40 (human CD40 IC), vectors without insert or "empty" pGBT9 vectors (pGBT9, negative control), and a construct encoding the ORF-B region of MACH (MACH B). In the assay, the development of color was determined, where the greater the color development, the greater the interaction between the constructs encoded by the DNA-binding domain and activation domain. Color development was depicted by symbols, where "+++" and "+" indicate the development of a strong color within 30 and 90 min. of the assay, respectively, and "---" indicates the lack of development of color within 24 hrs. of the assay. In cases where interactions were not tested, no symbol was indicated. The results of the various interactions for the above case are set forth in Table 3 below, and the results of the various interactions of the MACH isoforms are shown in above mentioned co-owned co-pending PCT/US96/10521 and its IL counterparts.

TABLE 3

| | DOMAIN HYBRID | | | |
| --- | --- | --- | --- | --- |
| | MACH | MACH B | MORT 1 | pGAD-GH |
| DNA-Binding Domain Hybrid | | | | |
| MORT-1 Binding region in MORT-1 | +++ | +++ | +++ | --- |
| MORT1 (-117) MORT1DD (130-245) Specificity tests | --- | --- | | |
| Lamin | --- | --- | | |
| human p75 IC | --- | | | |
| cyc D | | | | |
| SNF1 | | | | |
| human p55 IC | | | | |
| human FAS DD | --- | | | |
| human CD40 IC | --- | | | |
| pGBT9 | --- | | | |
| MACH B | | + | + | --- |

Thus, as arises from the results shown in Table 3 above, it is apparent that:

(a) MACH binds to MORT-1 in a very strong and specific manner;

(b) The MACH binding site in MORT-1 occurs before (upstream of) the 'death domain' motif in MORT-1, i.e., it is in the region of MORT-1 defined by aa 1-117 of MORT-1;

(c) The ORF-B region of MACH is the MORT-1-interacting region of the MACH protein; and (d) The MACH ORF-B region is capable of self-association.

(ii) Cell-cytotoxic Effects Mediated by the Self-association Capability of the MACH Protein The observation that MACH can self-associate, in particular, that the ORF-B region of MACH self-associates and the previous correlation between self-association and cell-cytotoxicity as observed for the intracellular domains of p55 TNF-R and FAS-R, and as observed for MORT-1 (see Reference Example 1), suggested that MACH self-association may also be involved in cell-cytotoxicity.

In order to test this possibility, constructs encoding MACH were prepared with a tetracycline-controlled expression vector (for details see Reference Example 1). These constructs were used to transfect HeLa cells in which the vectors were transiently expressed. Besides the MACH constructs, other control constructs were used to evaluate the effect of transient expression on the viability of the HeLa cells to which the effect of the MACH constructs could be compared. These other constructs included MORT-1, human FAS-IC and luciferase (Luc). In addition, co-transfection of the HeLa cells was also tested by using MORT-1 and MACH constructs to determine what effects the interaction between these proteins would cause. After transfection the HeLa cells were incubated and cell viability was evaluated 48 hrs. after transfection either in the presence or the absence of tetracycline (1 μg/ml) to block expression. Cell viability was determined by the neutral red uptake assay.

From the results of the above analysis, it was apparent that MACH induces a dramatic cytotoxic effect in HeLa cells, i.e., the induced overexpression of MACH cDNA in HeLa cells, results in a dramatic cytotoxic effect. This cytotoxic effect is likely to be related to the self-association capability of MACH.

(iii) Northern Analysis

Using well-known procedures (see Reference Example 1), Northern analysis of several cell lines was carried out using the MACH cDNA as a probe. The results of this analysis show that in a large number of cell lines, in particular, CEM, Raji, Daudi, HeLa, Alexander, Jurkat and A673 cell lines, there exist two hybridizing transcripts of approximately 3.2 kb in size.

In view of the above, the MACH protein, particularly the MACHβ1 protein (ORF-B of MACH) may be utilized directly to modulate or mediate the MORT-1 associated effects on cells, or, indirectly, to modulate or mediate the FAS-R ligand effect on cells when this effect is modulated or mediated by MORT-1. The fact that MACH binds specifically to the upstream region of MORT-1 and shares homology with MORT-1 provides for a specific way in which MACH or MACH ORF-B may be used to modulate this specific region of MORT-1 and hence the specific activity of MORT-1 determined by this upstream region. Further, MACH or MACH ORF-B may be used as a modulator or mediator of intracellular effects in an analogous way to MORT-1 itself (see above) by virtue of MACH's ability to self-associate and induce cell-cytotoxicity on its own.

Further analyses of the MACH protein and the DNA sequences encoding it have been performed as set forth herein below. Further, it was revealed that ORF-B of MACH represents but one of a number of MACH isoforms. Hence, the MACH protein and the DNA sequences encoding it have now been renamed, as will become apparent from the following.

(a) Two Hybrid Screen for Proteins that Bind to MORT-1 Reveals a Novel Protein Which Shares a Sequence Motif with MORT-1:

As mentioned above, to identify proteins which participate in the induction of cell death by MORT-1, the two-hybrid technique was used to screen cDNA libraries for proteins that bind to MORT-1. A two-hybrid screen of a human B cell library (Dufee et al., 1993) using MORT-1 cDNA as bait yielded cDNA clones of MORT-1 itself, reflecting the ability of this protein to self-associate as well as clones of TRADD, to which MORT-1 binds effectively (see Reference Example 2). The screen also yielded cDNA clones of a novel sequence whose product specifically bound to MORT-1. The protein, which initially was called MACH, and later, after finding that it occurs in multiple isoforms (see below), renamed MACHβ1, showed also an ability to bind in a two hybrid test to itself, yet was unable to bind to FAS-R (see above noted co-owned co-pending PCT/US96/10521, which also includes all of the following analyses and results obtained therefrom).

MORT-1 and MACHβ1 and their deletion constructs, as well as MACHα1, a MACHα1 mutant in which the catalytic cysteine $Cys_{360}$ is replaced by Ser (MACHα1 (C360S)) and the intracellular domain of human FAS-R (Fas-IC), were expressed within transfected SFY526 yeast in Gal4 DNA binding domain and activation domain constructs (pGBT9 and pGAD-GH). Their interaction was assessed by a β-galactosidase expression filter assay as described in Boldin et al., (1995b). The results are presented in terms of the time required for the development of strong color. None of the inserts examined interacted with a number of tested negative controls, including the intracellular domains of human p55 TNF receptor, p75 TNF receptor and CD40, and lamin, cyclin D and 'empty' Gal4 vectors. MACHβ1 was cloned by two hybrid screening of a Gal4 AD-tagged human B cell library (Durfee et al., 1993) for proteins that bind to MORT-1, using the HF7c yeast reporter strain. Except where otherwise indicated, all experimental procedures for the findings presented are as described above (see also Boldin et al., 1995). Deletion analysis showed that MACHβ1 binds to the N-terminal part of MORT-1, which is involved in cell death induction (Chinnaiyan et al., 1995). MACHβ1 also self-associated in the transfected yeast. However, it did not bind to several control proteins and unlike MORT-1 was unable to bind to FAS-R. Expression of MACHβ1 molecules in mammalian cells yielded a 34 kDa protein that bound to MORT-1 molecules co-expressed with it. It was also able to bind to a GST-MORT-1 fusion protein in vitro.

Comparison of the amino acid sequences in MACHβ1 and MORT-1 revealed a shared sequence motif (designated "Mort module") in these two proteins, distinct from the death motif through which MORT-1 binds to FAS-R. This motif occurs once in MORT-1 and twice in MACHβ1. The same motif is found also in PEA-15, an astrocyte phosphoprotein of unknown function. Preliminary data suggest that the MORT motif is involved in the binding of MACHβ1 (and of other MACH isoforms) to MORT-1.

The deduced amino acid sequence of MACHβ1 is presented in the above noted PCT/US96/10521 and its corresponding IL counterparts particularly IL 117932. The two MORT modules are shown and the C-termini of the two MACHβ1 deletion mutants employed are indicated. The sequence homology of the modules in MACHβ1, MORT-1 and the PEA-15 gene (accession number X86809) was also presented in the above co-owned co-pending applications, in which identical and similar residues were denoted by boxed and shaded areas, respectively.

A diagrammatic representation of the death domain and MORT modules and of the CED3/ICE homology region in Fas/APO1, MACHβ1 and MACHα1, is also presented in the above co-owned applications.

The region in MORT-1 that contains this 'MORT module' has been shown to take part in cell death induction by this protein (see Reference Example 1 above). It has been shown also to contribute to, though not to suffice in, the self association of MORT-1 (see Reference Example 1). Analysis of the binding properties of deletion constructs of MACHβ1 in transfected yeasts revealed similar involvement of the MORT modules in self-association of MACHβ1, as well as in its binding to MORT-1: Deletion constructs, in which the region below (downstream of) the MORT module was missing, were unable to bind to each other, yet maintained the ability to bind to the full length MORT-1 and to the full length MACHβ1. A further truncation in which part of the MORT module sequence was also deleted, resulted in loss of the binding ability of the proteins. To further assess the involvement of the MORT modules in these interactions, deletion mutants of MACHβ1, fused with the FLAG octapeptide (FLAG-MACHβ1), were expressed in HeLa cells and assessed for their binding in vitro to bacterial-produced glutathione-S-transferase-MORT-1 fusion protein (GST-MORT-1). Similarly to the binding observed in the yeast two-hybrid test, this in vitro binding was found to depend on interaction of the region within MACHβ1 modules. $^{35}$[S]-Metabolically labeled MACHβ1, MACHβ1 fused at its N-terminus to the FLAG octapeptide (FLAG-MACHβ1), C-terminus truncation mutants of FLAG-MACHβ1, and, as a control, luciferase, were produced in transfected HeLa cells. Expression was done using a tetracycline-controlled expression vector, in a HeLa cell clone (HtTA-1) that expresses a tetracycline-controlled transactivator.

Assessment of the expression of the proteins and their molecular sizes was performed by immunoprecipitation from cell lysates, using anti-FLAG antibody. The antibodies used are as follows: Rabbit anti-MACHβ1 and anti-MORT1 antisera were raised against GST-MACHβ1 and GST-MORT1 fusion proteins. Mouse monoclonal antibodies against the FLAG octapeptide (M2) and against FAS/APO1 (CH11, Yonehara et al., 1989) were purchased from Eastman Kodak and Oncor (Gaithersburg, Md.) respectively. Mouse monoclonal anti-HA epitope antibody (12CA5, Field et al., 1988) and anti-TNF antibody were produced in our laboratory according to the usual methods well known in the art. Results showing the affinity binding of the proteins to GST-MORT-1, adsorbed to glutathione-agarose beads (or, as a control, to GST or GST-fused to the intracellular domain of Fas-APO1); and the immuno-precipitations of the various MORT-1 and MACH fusion constructs using the various specific antibodies, are presented in the above noted co-owned co-pending applications, in particular, in PCT/US96/10521 and IL 117932.

(b) MACH Occurs in Multiple Isoforms:

Northern analysis using MACHβ1 cDNA as a probe revealed low abundant transcript(s) of approximately 3 kb in size in several different cell lines. Briefly, Northern blot analysis of total RNA (14 µg/lane) or poly A$^+$RNA (2 µg) from several cell lines, using MACHβ1 cDNA as probe was performed. The cell lines examined, T47D, CEM, Raji, Daudi, HeLa, Alexander, Jurkat and A673, are all of human origin and were derived from a ductal carcinoma of the breast, an acute lymphoblastic T cell leukemia, a Burkitt lymphoma, a Burkitt lymphoma, an epitheloid carcinoma, a human hepatoma, an acute T cell leukemia and a rhabdomyosarcoma, respectively. The rather diffuse shape of the hybridizing band on Northern blots suggested that these transcripts are of heterogeneous sizes ranging between 2.85 and 3.5 Kb. Both the amounts and the sizes of the transcripts varied among different human tissues and were not correlated with the expression of MORT1 or of FAS/APO1 (Watanabe et al., 1992). In the testis and skeletal muscle, for example, MACH transcripts were barely detectable, even though these tissues express significant amounts of MORT1. Conversely, resting peripheral blood mononuclear leukocytes, in which MORT1 expression is very low, were found to express MACH at high levels. Lectin activation of the leukocytes results in a marked change in the size pattern of MACH transcripts, along with an induction of MORT-1.

Exploring the nature of this size heterogeneity, cDNA libraries were screened for transcripts that hybridize with the MACHβ1 cDNA probe. MACHα1 and MACHα2 were cloned from a Charon BS cDNA library derived from the mRNA of human thymus. The library was screened under stringent conditions with a MACHβ1 cDNA probe, labeled using a random-priming kit (Boehringer Mannheim). The other MACH isoforms were cloned by RT-PCR, performed on total RNA from Raji (MACHα1, α2, α3, β3, and β4) and Daudi (MACHα2, β2, β3, β4, and β5) human lymphoblastoid cells. Reverse transcriptase reaction was performed with an oligo-dT adapter primer (5'-GACTCGAGTCTAGAGTC-GAC(T)$_{17}$-3') (SEQ ID NO:12) and the SuperScript II reverse transcriptase (GIBCO-BRL), used according to the manufacturer's instructions. The first round of PCR was performed with the Expand Long Template PCR System (Boehringer Mannheim) using the following sense and antisense primers: 5'-AAGTGAGCAGATCAGAATTGAG-3' (SEQ ID NO:13), corresponding to nucleotides 530-551 of the MACHβ1 cDNA, and 5'-GACTCGAGTCTAGAGTCGAC-3' (SEQ ID NO:14), respectively. The second round was performed with Vent polymerase (NEB) using the following sense and antisense nested primers: 5'GAGGATCCCCAAATG-CAAACTGGATGATGAC-3' (SEQ ID NO:15) and 5'-GC-CACCAGCTAAAAACATTCTCAA-3' (SEQ ID NO:16), derived from the sequence of MACHβ1 cDNA, respectively. To confirm that MACHβ3 and MACHβ4 have initiation codons, a more 5' sequence of these isoforms from the RNA of Raji cells was cloned. The RT-PCR reaction, performed using the oligo-dT adapter primer as described above, was followed by two rounds of PCR (with Vent polymerase (NEB)) using the following sense and antisense oligonucleotides: 5'-TTGGATCCAGATGGACTTCAGCA-GAAATCTT-3' (SEQ ID NO:17) and 5'-ATTCTCAAAC-CCTGCATCCAAGTG-3' (SEQ ID NO:18), derived from the sequence of MACHβ1. The latter oligonucleotide is specific to the β-isoforms. Among the clones obtained in this way, those found to contain the nucleotides encoding for the amino acids of 'block 2' (whose presence distinguishes MACHβ3 and MACHβ4 from MACHβ1 and MACHβ2) were fully sequenced. Nucleotide sequences in all cloned isoforms were determined in both directions by the dideoxy-chain termination method. Only partial cDNA clones of MACHa3 and MACHβ2 were obtained. This screening revealed the existence of multiple isoforms of MACH MACH. The amino acid sequences of seven of these isoforms were studied in detail. The results are illustrated diagrammatically and exemplified in the above co-owned co-pending applications, particularly PCT/US96/10521 and IL 117932, where the amino acid sequences of three of the isoforms are compared with known homologs.

Lack of the 65 nucleotides which in MACHα1 encode for 'block 2' causes alteration in MACHβ1 and MACHβ2 of the reading frame of the nucleotides that encode for 'block 3'. In those isoforms, therefore, these nucleotides encode other amino acids which together constitute their unique C-terminal region. On the other hand, in MACHβ3 and MACHβ4 the reading frame of block 3 is maintained, but absence of the nucleotides that encode the CED3/ICE region and part of the 3' noncoding region results in alteration of the reading frame of nucleotides further downstream. Because of this alteration, the most 5' part of this noncoding downstream region does encode 10 amino acids, which constitute the C-terminal region unique to these two isoforms.

The isoforms were cloned from a human B cell cDNA library (MACHβ1), from a human thymus cDNA library (MACHα1 and α2) and from the mRNA of the human lymphoblastoid cells Raji (MACH2α1, α2, α3, β3 β4, and β5) and Daudi (MACHα2, β2, β3, β4 and β5). Cloning from the mRNA of the Raji and Daudi cells was done by RT-PCR, using oligonucleotides corresponding to a 3' noncoding region and to a sequence within the second MORT module in MACHβ1. The starting codon of clones isolated in that way is therefore located within the second MORT module.

The sequences in the different isoforms relate to each other as follows: (a) All the MACH isoforms share a common 182-amino acid N-terminal region which encompasses the MORT modules, yet vary carboxy terminally (3' downstream) to these modules, as well as in their noncoding regions. (b) On the basis of their C terminal sequences, the isoforms fall into two subgroups: four isoforms defined as subgroup β, have different C-termini due to alteration in the reading frame. Two (MACHβ1 AND β2) share the C-terminus found in the isoform initially cloned in the two-hybrid screen and two (MACHβ3 and β4) share a different C-terminus; three isoforms, defined as subgroup α, have a much longer C-terminal region that closely resemble proteases of the CED3/ICE family (see below); (c) The regions extending between the MORT module region and the C terminal region that defines the subgroups varied from one isoform to another. However, close examination showed that these intermediate regions consist of different combinations of the same three amino acid sequence blocks (blocks 1, 2 and 3). The variations of amino acid sequence among the different clones reflect two kinds of variations in nucleotide sequence, that most likely occur by alternative splicing: (a) insertion or absence of either of two nucleotide sequences, one of 45 nucleotides (nts) and the other of 65 nts, or of both, below the nucleotides encoding Lys184; (b) presence of an additional insert within the region which in MACHβ1 constitutes the 3' noncoding part. These variations affect both the reading frame and the length of the protein.

Part of the MACH isoforms encompass a CED3/ICE homolog. Data bank search. revealed that the C terminal region of MACHα isoforms including block 3 and the sequence extending downstream of it, closely resemble proteases of the CED3/ICE family. A sequence comparison of this region in MACH and the various known human members of this family as well as the *Caenorhabditis elegans* ced3 protein was performed (Ellis and Horvitz, 1986; Yuan et al., 1993), and the known human proteases of the CED3/ICE protease family: CPP32 (Fernandes-Alnemri et al., 1994), also called apopain (Nicholson et al., 1995) and Yama (Tewari et al., 1995b), Mch2α (Fernandes-Alnemri et al., 1995), Ich-1 (Wang et al., 1994; the human homolog of the mouse Nedd2 protein, Kumar et al., 1994), ICE$_{rel}$II (<umday et al., 1995), ICE$_{rel}$II (Munday et al., 1995), also called TX and Ich2 (Faucheu et al., 1995; Kamens et al., 1995), and ICE (Thornberry et al., 1992; Cerretti et al., 1992).

The above C-terminal region of MACH most closely resembles CPP32 (with 41% identity and 62% homology) and CED3 (with 34% identity and 56% homology). It shows a significantly lesser similarity to ICE (with 28% identity and 50% homology) and to its closely related homologs ICE$_{rel}$II (also called TX and Ich2) and ICE$_{rel}$III. The similarity was observed throughout almost the whole region starting from Tyr226 within block 3, to the C terminus of the MACHα isoforms.

Two points of similarity are particularly notable:

(a) All known proteases of the CED3/ICE family cleave proteins at sites defined by the occurrence of Asp at the P1 position and a small hydrophobic amino acid residue at P1'. Their specificity differs, though, with regard to other structural features of the substrate, including the nature of the residues at positions P2-P4. Accordingly, the active site residues involved in catalysis (corresponding to His237, Gly238 and Cys285 in ICE) and in the binding pocket for the carboxylate side chain of the P1 Asp (Arg179, Gln283, Arg341 and probably also Ser347) are conserved among these proteases. These residues are also conserved in MACHα1. There is one exception, though—a conservative change of Ser to Thr at the site corresponding to Ser347 of ICE. Another slight, yet potentially important, sequence difference between MACHa isoforms and other members of the protease family is an Arg to Gln replacement of the residue corresponding to Arg286 of ICE. This residue, which is adjacent to the putative catalytic cysteine residue, is fully conserved in all other CED3/ICE family members. Also part of the residues at the sites located close to the substrate P2-P4 residues differ in the MACHα isoforms from those found in other CED3/ICE family members.

(b) Proteases of the CED3/ICE family contain sites of autocleavage. Several of the proteases are known indeed to be self-processed, and to depend on this processing for displaying maximal catalytic activity. Their fully bioactive form is composed of two noncovalently-associated cleavage products, which differ in size (p20 and p17 in ICE; p17 and p12 in CPP32). Presence of potential sites of autocleavage in other members of the family suggests that they are subject to similar processing, and, similarly, depend on this processing for exhibiting maximal activity. Such potential sites of autocleavage occur in MACHα1 almost at the same locations as in the CPP32. The site corresponding to the N terminus of the p17 subunit of CPP32 is located in the second conserved block of amino acids, just a few amino acids upstream to the N terminus of the CED3/ICE-homology region (below Asp216). The site corresponding to the point of cleavage between the two subunits of CPP32 is located, as in all other members of the CED3/ICE family that are known to be cleaved, a few amino acids downstream to the catalytic cysteine residue (below Asp374). This conservation suggests that the CED3/ICE homology region in MACHα1 is subject to proteolytic processing. The sizes of the two expected products of this cleavage are very close to that of the two subunits of the processed CPP32 molecule.

(c) The CED3/ICE Homology Region in MACH has Proteolytic Activity.

To find out if the CED3/ICE homology region in MACHa possesses proteolytic activity, applicants expressed the region that extends from the potential cleavage site upstream to this region, between Asp216 and Ser217, till the C terminus of the protein in bacteria, as a GST fusion protein. The bacterial lysates were examined for ability to cleave fluorogenic peptide substrates, shown before to be cleaved by other CED3/ICE homologs. Two substrate peptides were used: The first, Acetyl-Asp-Glu-Val-Asp-a-(4-Methyl-Coumaryl-7-Amide) (AC-DEVD-AMC) (SEQ ID NO:10), corresponds to a sequence in poly (ADP-ribose) polymerase (PARP), a nuclear protein found to be cleaved in cells shortly after FAS-R stimulation (Tewari et al., 1995b), as well as in other apoptopic processes (Kaufmann, 1989; Kaufmann et al., 1993; Lazebnik et al., 1994). This fluorogenic substrate is cleaved effectively by CPP32. The second fluorogenic substrate, Acetyl-Tyr-Val-Ala-Asp-AMC (Ac-YVAD-AMC) (SEQ ID NO:11), corresponds to a substrate site for ICE in the IL-1β precursor. This fluorogenic substrate is cleaved by ICE. Lysates of bacteria expressing the CED3/ICE homology region in MACHα1 cleaved effectively the PARP sequence-derived fluorogenic substrate. They had no measurable proteolytic activity, though, against the IL-1β-precursor sequence-derived fluorogenic substrate (controls), Ac-YVAD-AMC, which is an ICE cleavage site in IL-1β precursor (Thornberry et al, 1992). The proteolytic activity was blocked by iodacetic acid (5 mM), confirming that it is mediated by a thiol protease. No cleavage was observed with lysates containing the GST-fused MACH CED3/ICE-homology region in which the catalytic cysteine residue $Cys_{360}$ was replaced by Ser. Also, lysates from bacteria that expressed the full-length MACHα1 protein as a GST-fusion protein did not cleave Ac-DEVD-AMC, probably because of the absence of bacterial enzymes capable of processing the full-length molecule. Nor did cleavage occur with lysates containing either of the two potential cleavage products of the CED3/ICE homology region.

The kinetics of cleavage of the PARP sequence-derived fluorogenic substrate, Ac-DEVD-AMC (50 μM), by extracts of E. coli expressing a GST-fusion protein of the CED3/ICE homology region in MACHα1 (Ser217 through the C-terminus of the protein) was shown as compared to the lack of cleavage by extracts of bacteria expressing GST-fusion proteins of the full-length MACHα1 molecule or of either one of the two potential proteolytic products of the CED3/ICE homology region (Ser217 till Asp374 and Asp374 through the C-terminus of the protein).

Further, the substrate concentration-dependence of the cleavage of Ac-DEVD-AMC, incubated for 180 min. with extracts of bacteria expressing the MACHα1 CED3/ICE homology-region in fusion with GST was shown. No cleavage was observed in the presence of iodoacetic acid (5 mM). The extracts had no activity on Ac-YVAD-AMC, a fluorogenic substrate corresponding to a substrate site for ICE in the IL-1β precursor.

Briefly, the GST-fusion proteins were produced in XL1-blue bacteria using the pGEX3 expression vector. The bacteria were lysed by sonication in a buffer containing 25 mM HEPES (pH 7.5), 0.1% 3-[3-cholamidopropyl)dimethylamino]-1-propanesulfonate, 5 mM EDTA and 2 mM DDT, followed by centrifugation at 16,000×g for 10 min. SDS-PAGE analysis confirmed the presence of similar levels of the various fusion proteins in the lysates. 50 μl aliquots of the extracts (4 mg/ml of total protein) were incubated at room temperature for the indicated periods in a 500 μl total volume reaction with the fluorogenic substrates, at the indicated concentrations. AMC release was measured by spectro-fluorometry at an excitation wavelength of 380 nm and an emission wavelength of 460 nm. The concentration of AMC was determined from a standard curve. Both fluorogenic substrate peptides were obtained from Peptide Institute Inc. (Osaka, Japan). Other CED3/ICE proteases were shown to exhibit full activity only after proteolytic processing, which occurs either by self-cleavage, or via their cleavage by other proteases (reviewed in Kumar, 1995; Henkart, 1996). Applicants' observation that lysates of bacteria that express GST-MACHα1 molecules do not possess enzymatic activity, as opposed to the activity observed in lysates of bacteria that express the CED3/ICE homology region, suggests that processing is also required for MACHα activity. The way in which MACHα processing occurs within the mammalian cell, and how this processing is brought about by FAS-R or p55-R triggering, is not known. MORT-1 has been shown to bind in cells to activated FAS-R together with some other proteins (Kischkel et al., 1995). These proteins are likely to include MACHα1 and other MACH isoforms. It seems plausible that the binding of MORT-1 in association with MACHα to FAS-R brings together several MACH molecules, or induces conformational changes in them, and that these changes either trigger autolytic processing of MACHα or make MACHα susceptible to cleavage by other proteases. Stimulation of p55-R may trigger self-processing of MACHα in a similar, though less direct manner, by bringing together several TRADD molecules, or inducing a conformational change in them, which in turn induces a change in the formation or state or aggregation of MORT-1 and its associated MACH molecule.

The substrate specificity of MACHα seems to be rather 'death oriented'. Although it could cleave a substrate peptide corresponding to a cleavage site in the death substrate PARP (Ac-DEVD-AMC), MACHα showed no proteolytic activity towards a peptide corresponding to the site of processing of the IL-1β precursor by ICE (Ac-YVAD-AMC). Identification of the cellular proteins that serve as substrates for cleavage: by MACHα will elucidate the more downstream events in death induction by this protease. Likely substrates for MACHα cleavage are other members of the CED3/ICE family, like CPP32 and ICE. Some of these proteases are indeed processed after FAS-R or TNF receptor-triggering (Miura et al., 1995; Schlegel et al., 1996; Chinnaiyan et al., 1996). Perhaps proteases that do not belong to the CED3/ICE family are also activated by MACHα, either directly or through the action of other CED3/ICE proteases. Involvement of multiple proteases in the cell death process is consistent with the reported ability of inhibitors of various proteases, including inhibitors of serine proteases and an inhibitor of ICE cleavage as well as antisense ICE cDNA, to protect cells from FAS-R and TNF receptor-induced toxicity (Weitzen and Granger, 1980; Ruggiero et al., 1987; Enari et al., 1995; Los et al., 1995).

A variety of other enzymes, including phospholipases, sphingomyelinases and protein kinases, may participate in cell death induction by the TNF receptors and FAS-R (see Eischen et al., 1994; Vandenabeele et al., 1995; Cifone et al., 1995 and references therein). Some of these enzymes may become activated by the proteolytic cleavage initiated by MACHα. It also seems possible, however, that at least part of these other death-related activities are stimulated by distinct signaling routes, independently of MACHα stimulation. Involvement of more than one signaling cascade in the induction of cell death, some common to p55-R and FAS/APO1 and some induced by only one of them, would be consistent with report on both shared and distinct features of cell death processes induced by the two receptors (Grell et al., 1994; Schulze-Osthoff et al., 1994; Wong and Goeddel, 1994; Clement and Stamenkovic, 1994).

(d) MACHα1 Binds to MORT1 as Well as to MACHβ1:

To find out if MACHα1 can bind to MORT1, as does MACHβ1, the interaction of the proteins within transfected yeasts was first examined. MACHα1 appeared to have a significant cytotoxic effect on the yeasts. This effect was manifested in a marked decrease in the yield of colonies in yeasts that expressed the protein in the activation domain (AD) vector (whose expression level is higher than that of the DNA binding domain (DBD) vector). On the other hand, MACHβ1 in which the catalytic cysteine residue, $Cys_{360}$, was replaced with Ser (MACHα1 (C360S)) was not cytotoxic to either mammalian cells (see below), or yeast. Like MACHβ1, MACHα1 (C360S) bound in. transfected yeast to MORT-1 and also to itself. It also bound to MACHβ1. Also, yeast expressing the wild-type MACHα1 together with MORT-1 or MACHβ1 exhibited interaction of the transfected proteins. The intensity of the lacZ-product color varied, however, among the yeast colonies; in yeasts transfected with MACHα1 in both the AD and the DBD vectors no color product was observed, probably because of the cytotoxic effect of the wild-type MACHα1. Yet, in spite of this variation, yeasts expressing MACHα1 either in combination with MORT1 or in combination with MACHβ1 scored clearly positive for interaction of the transfected proteins. Unlike MACHβ1, MACHα1 did not exhibit self-interaction in the two hybrid test.

Both MACHα1 (C360S) and MACHβ1 coimmunoprecipitated with MORT-1 from lysates of human embryonic kidney 293-EBNA cells, indicating that they bind to MORT-1 also in mammalian cells. Testing further if MACHα1 can bind to MORT1 also within mammalian cells, MACHα1 or MACHβ1, fused with the FLAG octapeptide was expressed, together with HA epitope-tagged MORT1 molecules. $^{35}$[S] metabolically labeled MACHα1 and MACHβ1 fused at their N-termini to the FLAG octapeptide (FLAG-MACHa1 and β1), and MORT1 fused at its N terminus to the HA epitope (Field et al., 1988) were expressed in HeLa cells. Immunoprecipitation of the proteins from lysates of the cells was performed using mouse monoclonal antibodies against the FLAG octapeptide (M2; Eastman Kodak), HA epitope (12CA5, Field et al., 1988) or the p75 TNF receptor (#9, Bigda et al., 1994) as a control. The proteins were analyzed by SDS-polyacrylamide gel electrophoresis (12% acrylamide), followed by autoradiography. Both MACHα1 and MACHβ1 co-immunoprecipitated with MORT1 from lysates of the cells, indicating that they bind to MORT1. The effectivity of interaction of MACHα1 with MORT1 appeared to be lower than that of MACHβ1.

(e) MACH Molecules that Contain the CED3/ICE Homology Region can Mediate Cell Death:

To explore the involvement of MACH in cell-death induction, the effect of overexpression of various MACH isoforms on cell viability was examined. The test was performed by transfecting MACH expression vectors together with a β-galactosidase. expression vector as a transfection marker into human embryonic kidney 293-EBNA cells and breast carcinoma MCF7 cells.

In brief, 293-EBNA cells, MCF7 human breast carcinoma cells and HeLa HtTA-1 cells were grown in Dulbecco's modified Eagle's minimal essential medium supplemented with 10% fetal calf serum, nonessential amino acids, 100 U/ml penicillin and 100 µg/ml streptomycin. Cell tissue culture dishes ($5 \times 10^5$ 293-EBNA cells, $3 \times 10^5$ MCF7 cells or $3 \times 10^5$ HeLa cells in 6-cm dishes) were transiently transfected, using the calcium phosphate precipitation method, with the cDNAs of the indicated proteins together with the β-galactosidase expression vector. In one set of experiments, each dish was transfected with 3.5 µg of the MACH construct and 1.5 µg of pSV-β-gal; and in another set of experiments, each dish was transfected with 2.5 µg of the indicated MACH or MORT1 construct (or, as control, empty vector) and 1.5 µg of pSV-β-gal. The cells were rinsed 6 to 10 h after transfection. The 293-EBNA and MCF7 cells were incubated for a further 18 h without additional treatment. The HeLa cells were incubated for 26 h after transfection and then for 5 h in the presence of either anti-Fas.APO1 antibody (CH11, 0.5 µg/ml) or TNF (100 ng/ml), together with cycloheximide (10 µg/ml). The extent of cell death at the end of the incubation periods was assessed by determination of β-galactosidase expression, as described by Kumar et al., 1994.

Cultures transfected with an expression vector of either MACHα1 or MACHα2 exhibited massive cell death, manifested by cell rounding, blebbing, contraction, and finally detachment of cells from the dish. By 20 h after transfection, the majority of the transfected cells, identified by β-galactosidase staining (X-Gal), showed condensed morphology typical of apoptosis. In contrast, cells expressing the empty vector remained viable.

To examine the involvement of the CED3/ICE homology region within the MACHα isoforms in their apoptopic effects, cells were transfected with the expression vector for the MACHβ1 isoform, which lacks the CED3/ICE homology region, as well as with expression vectors for MACHα3, which lacks an N-terminal part of the region, and with expression vectors for MACHα1(C360S) and for a C-terminally truncated mutant of MACHα1 (MACHa1(1-415)), which lacks one of the residues believed to be critical for CED3/ICE protease function (corresponding to $Ser_{347}$ in ICE). No death (beyond the slight amount observed in cells transfected with an empty expression vector) occurred in 293-EBNA or MCF7 cells transfected with the expression vectors for MACHα3, MACHα1(1-415) or MACHα1(C360S). Moreover, cells transfected with MACHα1 together with these vectors also exhibited very little cell death, indicating that MACH molecules that contain an incomplete CED3/ICE region have a negative dominant effect on the activity of the wild-type molecules. Cultures expressing MACHβ1, which does not contain the CED3/ICE region at all, did exhibit some slight cell death. This effect of MACHβ1, which most probably results from activation of endogenous MACHα1 molecules, was for some reason more pronounced in transfected HeLa cells. Moreover, in HeLa cells MACHα3, MACHα1(1-415) and MACHα1(C360S) were also somewhat cytotoxic.

MACHα activity appears to constitute the most upstream enzymatic step in the cascade of signaling for the cytocidal effects of FAS/APO1 and p55-R. The ability of MACHβ1 to bind to both MORT-1 and MACHα1 suggests that this isoform enhances the activity of the enzymatically active isoforms. It is possible that some of the MACH isoforms serve additional functions. The ability of MACHβ1 to bind to both MORT-1 and MACHα1 suggests that this isoform might enhance the activity of the enzymatically active isoforms. The mild cytotoxicity observed in 293-EBNA and MCF7 cultures transfected with this isoform and the rather significant cytotoxic effect that it exerts in HeLa cells probably reflect activation of endogenously expressed MACHα molecules upon binding to the transfected MACHβ1 molecules. Conceivably, some of the MACH isoforms could also act as docking sites for molecules that are involved in other, non-cytotoxic effects of FAS/APO1 and TNF receptors.

(f) Blocking of MACHα Function Interferes with Cell Death Induction by Fas/APO1 and P55-R To assess the contribution of MACHα to Fas/APO1 and p55-R cytotoxicity, MACHα3, as well as the nonfunctional MACHα1 mutants, MACHα1(1-415) and MACHα(C360S), were expressed in cells that were induced to exhibit this cytotoxicity. p55-R-induced cytotoxicity was triggered in the 293-EBNA cells by transient over-expression of this receptor (Boldin et al., 1995a), and Fas/APO1 cytotoxicity by over-expression of chimeric molecules comprised of the extracellular domain of the p55-R and the transmembrane and intracellular domains of Fas/APO1. This chimera had a far greater cytotoxic effect than that of the normal Fas/APO1. Cytotoxic activities in HeLa cells was also induced by treating them with TNF or anti-Fas/APO1 antibody in the presence of the protein-synthesis blocker cycloheximide. The HeLa cells were made responsive to Fas/APO1 by transient expression of this receptor. In all systems examined, MACHα3 and the nonfunctional MACHα1 mutants provided effective protection against the cytotoxicity induced by Fas/APO1 or p55-R triggering. Such protection was also observed, as previously reported (Hsu et al., 1996; Chinnaiyan et al., 1996), in cells transfected with a MORT-1 N-terminal deletion mutant that lacks the MACH-binding region (MORT1(92-208)). These protective effects indicate that MACHα is a necessary component of both the Fas/APO1- and the p55-R-induced signaling cascades for cell death.

MACH is expressed in different tissues at markedly different levels and apparently also with different isotype patterns. These differences probably contribute to the tissue-specific features of response to the FAS/APO1 ligand and TNF. As in the case of other CED3/ICE homologs (Wang et al., 1994; Alnemri et al., 1995), MACH isoforms containing incomplete CED3/ICE regions (e.g. MACHα3) are found to inhibit the activities of coexpressed MACHα1 or MACHα2 molecules; they are also found to block death induction by FAS/APO1 and p55-R. Expression of such inhibitory isoforms in cells may constitute a mechanism of cellular self-protection against FAS/APO1- and TNF-mediated cytotoxicity. The wide heterogeneity of MACH isoforms, which greatly exceeds that observed for any of the other proteases of the CED3/ICE family, should allow a particularly fine tuning of the function of the active MACH isoforms.

EXAMPLE 1

Cloning and Isolation of the G1 Protein Which Binds to the MORT-1-Binding Protein Mch4

(i) Two-Hybrid Screen and Two-Hybrid β-Galactosidase Expression Test

Using the procedures set forth hereinabove in the Reference Examples 1-3, a new protein designated G1 was isolated which is apparently homologous to and hence possibly a member of the family of ICE-like proteases. The G1 protein contains two modules with homology to the MORT modules, namely with homology to the, MORT-1 N-terminal part, the MORT modules of the MACH proteins (see above reference Example 1-3 and Boldin et al., 1996) and the MORT modules of another related MORT-1-binding protein Mch4 (see Fernandes-Alnemri et al., 1996; Srinivasula et al., 1996). Further, the G1 protein has an enzymatic (protease-like) region that is homologous to the enzymatic (protease) regions of proteases of the CED3/ICE family (for example, the protease regions of the MACH proteins and Mch4, and others).

Briefly, a clone of protein G1 ('clone G1') was obtained following two-hybrid screening of a human Jurkat T cell cDNA library using the protein Mch4 as 'bait'. A Gal4 activation domain-tagged human Jurkat T cell cDNA library was used, and screening was performed using the HF7c yeast reporter strain (Clontech, Palo Alto, Calif.) in the absence of 3-aminotriazole according to the Matchmaker™ Two-Hybrid System Protocol (Clontech). The Mch4 sequence was obtained from the EMBL database. Using this obtained sequence, PCR-primers were designed by OLIGO4™ software and the DNA fragment corresponding to the coding part of Mch4 was obtained by reverse transcriptase-PCR (RT-PCR) from the total RNA obtained (by standard methods) from primary Human Umbilical Vein Endothelial cells. This coding part of Mch4 was then cloned into the pGADGH vector (Clontech) and used as a bait, as noted above, in the two-hybrid screening procedure. In this two-hybrid screen 11 clones were obtained, all coding for a protein which was apparently a splice variant of the protein containing two motifs of homology to MORT-1. Analysis of the preliminary partial sequence of G1 and sequences in the 'dbest' database and Human Genome Database level 1 enabled the obtention of a number of expressed sequence tags (est) containing parts of the sequence of the clone G1. Sequence analysis of these est revealed that there are possibly a number of splice variants of protein G1 that contain a sequence stretch coding for a protein motif that is homologous to ICE-like proteases and that this sequence stretch is located 3' to the G1 sequence obtained in the two-hybrid screening.

To obtain a full sequence of the isoform of G1 which contains the protease-like enzymatic region, reverse transcriptase reaction was performed on total RNA obtained from various cell lines using as a primer an oligonucleotide containing a 15 dT stretch and an adaptor sequence to yield cDNA molecules. These cDNA molecules were then used as templates in a PCR reation in which the PCR primers were designed and synthesized in the form of oligonucleotides having a sequence obtained from the 5' non-coding part of G1 and an adaptor sequence, these primers being used in a first-round PCR reation. Subsequently in the second-round of the above PCR reaction additional oligonucleotide primers were used having a sequence from the 5' coding part of G1 inclusive of the initiator ATG, as well as an adaptor sequence. In this way it was possible to obtain the full sequence of an apparent splice variant of G1 protein which contains the enzymatic (protease-like) region. This represents but one of the suspected G1 isoforms.

A preliminary sequence of one such G1 isoform, a G1 splice variant, is presented in SEQ ID NO:1 (nucleotide sequence) and in SEQ ID NO:2, deduced amino acid sequence of an ORF starting from ATG (nucleotide No. 482) and terminating at TAA (nucleotide 1921). The G1 splice variant of SEQ ID NOs:1 and 2 has also been putatively designated 'G1α'.

SEQ ID NOs:3 and 4 present the preliminary sequence of another G1 isoform, a short G1 splice variant having two MORT MODULES, putatively designated 'G1β', in which SEQ ID NO:3 is the nucleotide sequence and SEQ ID NO:4 is the deduced amino acid sequence of an ORF starting at nucleotide No. 482 (ATG) and terminating at nucleotide No. 1145 (TGA).

Figure 1A:
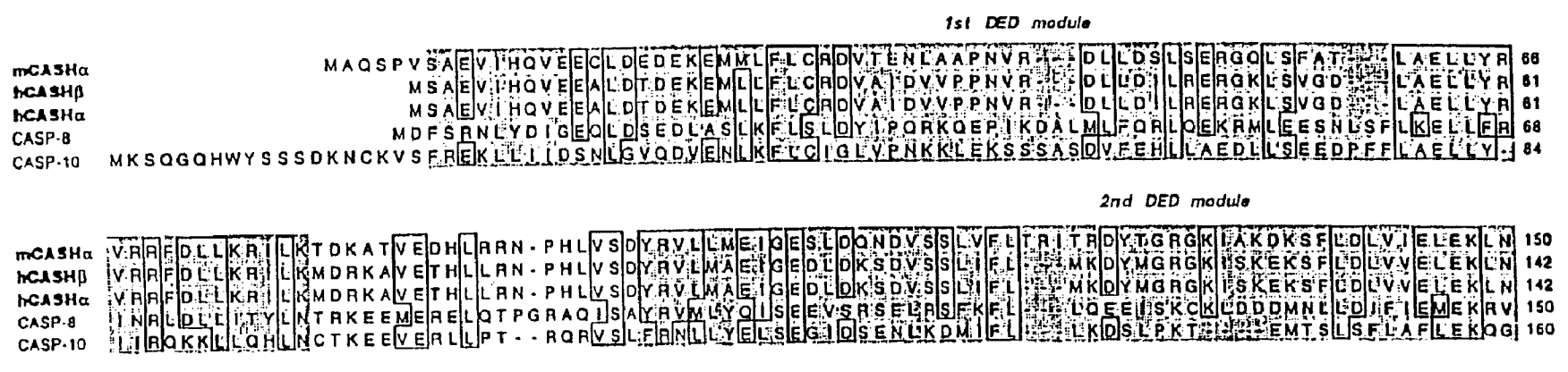

Furthermore, it should be noted that the originally isolated G1 clone obtained using the Mch4 sequence as 'bait' was at least part of the short splice variant of G1, called G1β. This originally isolated G1 clone was a partial clone of a novel cDNA, which like MACH (CASP-8) and Mch4 (CASP-10), contained two 'death domain motifs/Mort Modules (or 'death effector domains'—DED) just downstream of its N-terminus (see FIGS. 1A-1C). Using this original clone it was then possible to isolate and characterize the cDNA clones for the larger splice variant G1α and the shorter splice variant G1β. The larger splice variant had a C-terminal region with homology to the protease region of caspases and hence is likely to be a new member of the caspase family. As such G1 has also been designated CASH for 'caspase homolog'. A comparison of the G1α (CASHα) and G1β (CASHβ) sequences with other caspase sequences was carried out (for further details, especially the isolation of the mouse G1 sequence, see below and above under 'Brief Description of the Drawings' with respect to FIGS. 1A-1C). The results of this comparison are set forth schematically in FIGS. 1A-1C, the full details of which, in particular, the key to the indicated sequences in this figure are noted above under 'Brief Description of the Drawings'.

Figure 2A:
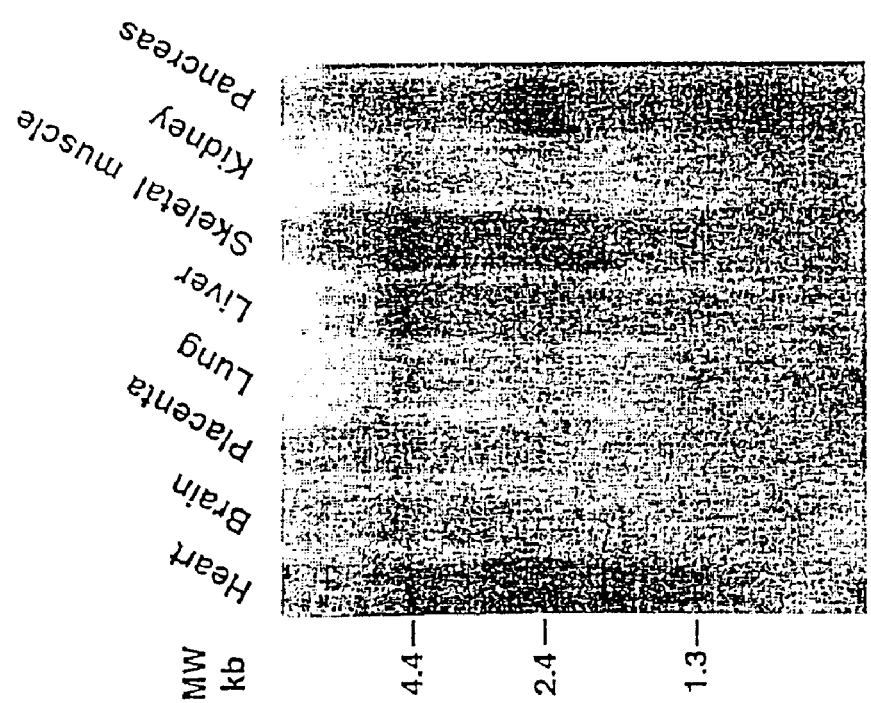
Figure 3:
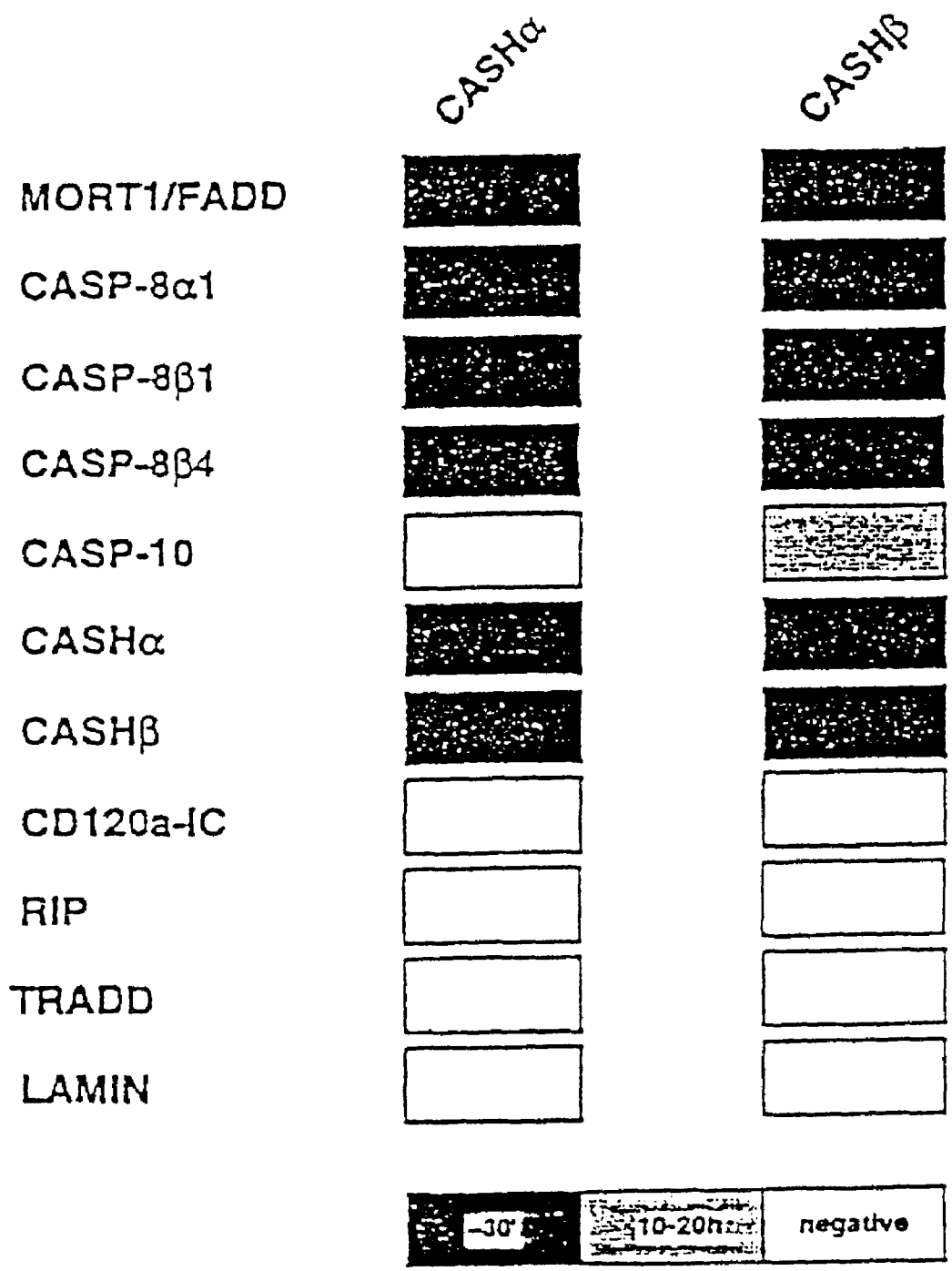
FIG. 3 is a schematic presentation of the results showing the interaction of G1α (CASHα) and G1β (CASHβ) with other 'death domain' (DED)-containing proteins within transfected yeast (e.g. MORT1/FADD, MACHα1 (CASP-8α1), MACHβ1 (CASP-8β1), MACHβ4 (CASP-8β4), Mch4 (CASP-10), G1α (CASHα), G1β (CASHβ), p55-R (p55ic), RIP, TRADD and Lamin (negative control)). The binding properties of G1β (CASHβ), as well as G1α (CASHα) were assessed in the yeast SFY526 reporter strain (Clontech), using the pGBT9-GAL4 DNA-binding domain and the pGAD1318 and pGADGH-GAL4 activation-domain vectors. Quantification of the binding in yeast by the β-galactosidase expression filter assay was performed as noted in the Reference Examples 1-3. Results are expressed as the time required for development of strong color. In all cases tested, identical results were obtained when placing the tested inserts in the DNA-binding domain and activation-domain constructs in both combinations. None of the examined inserts interacted with several control proteins, including the intracellular domains of human p55-R (CD120a), p75-R (CD120b), CD40, lamin, and empty Gal4 vectors.
Figure 4A:
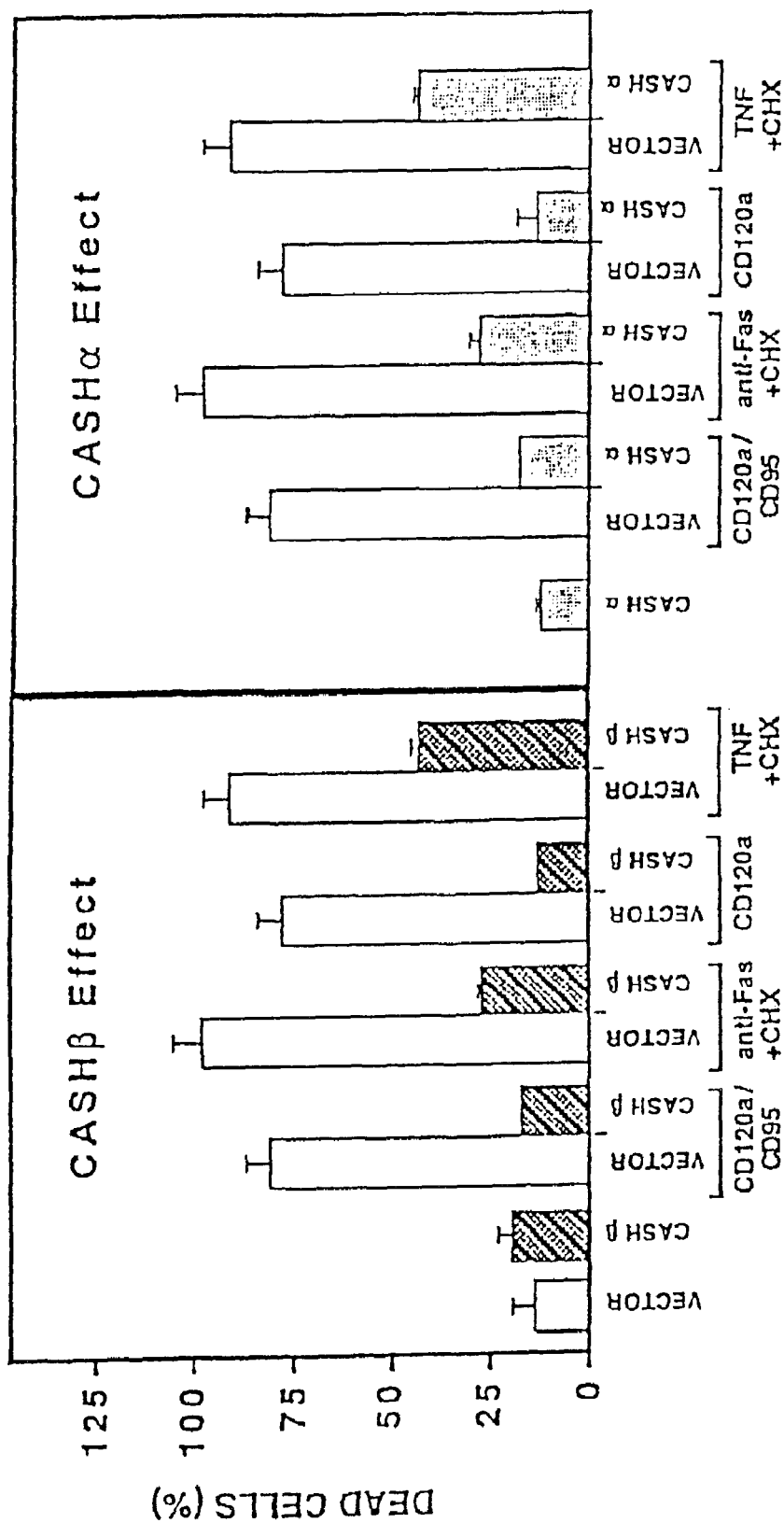
Figure 4D:
Figure 4D:
Figure 4D:
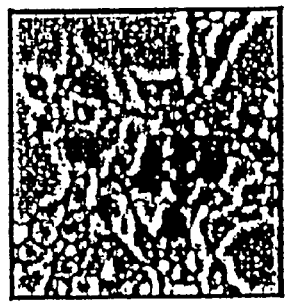
Figure 4D:
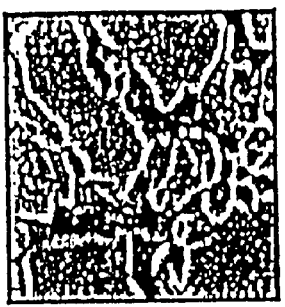
Figure 5:
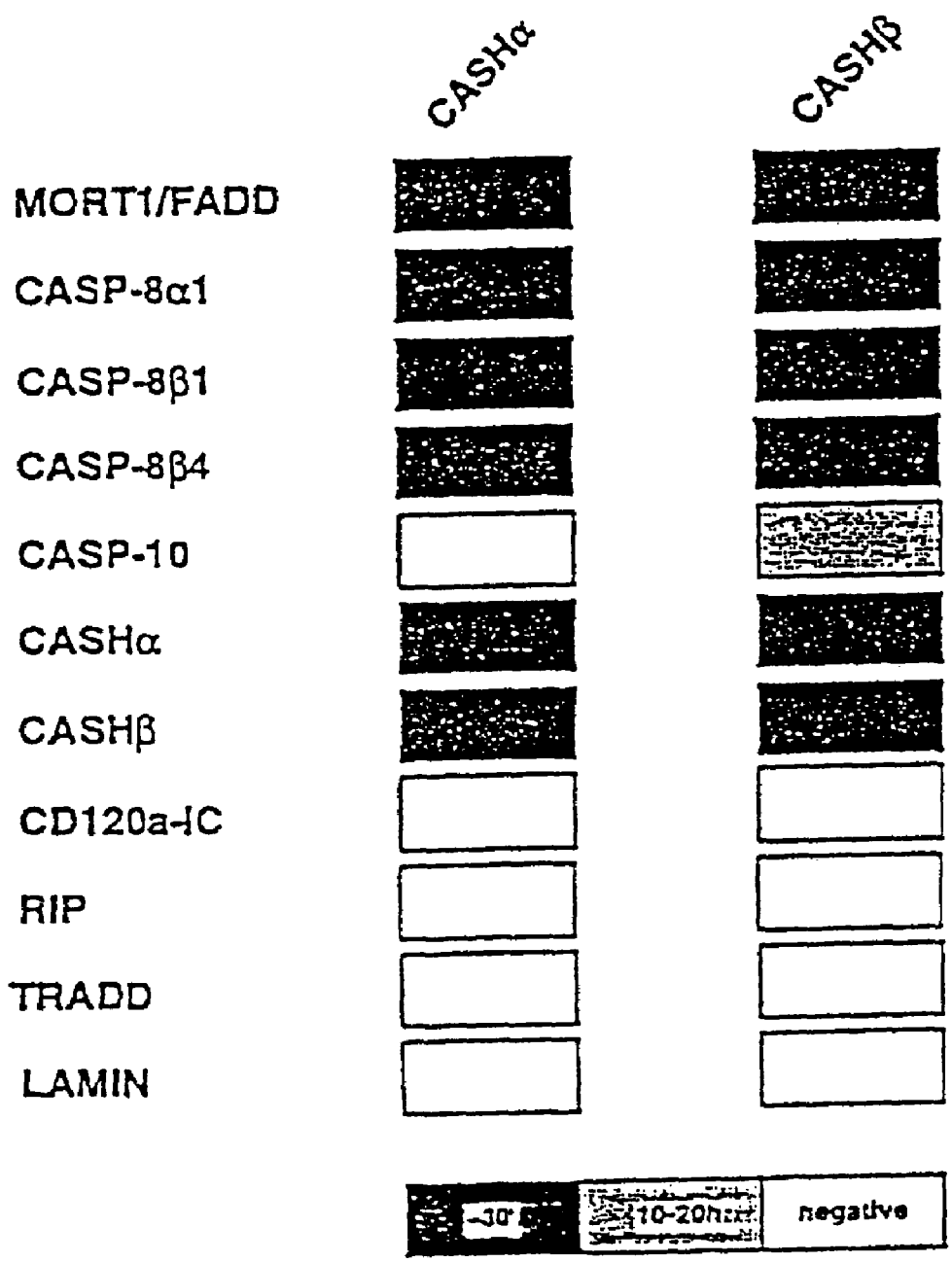
Figure 6A:
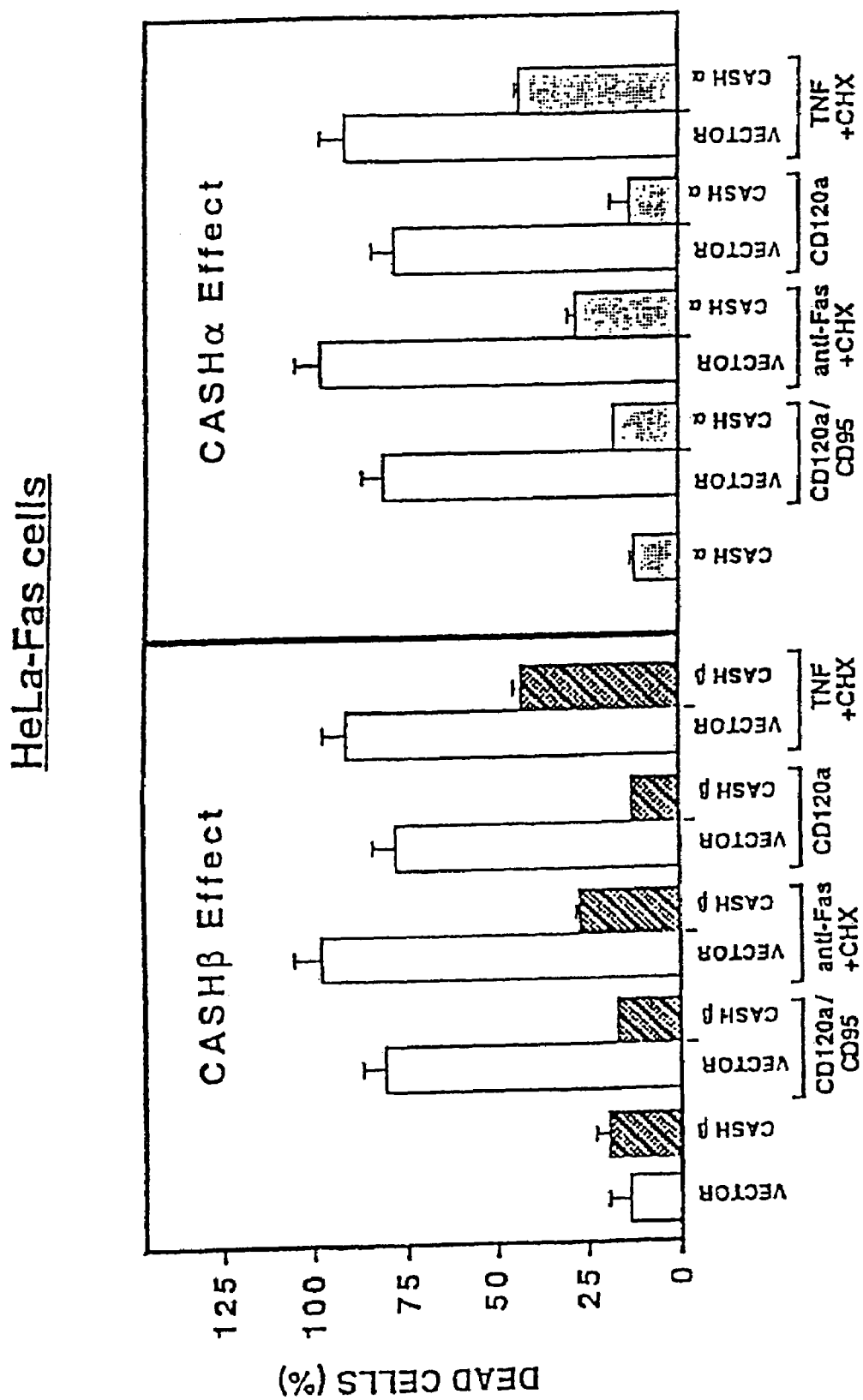
Figure 6C:
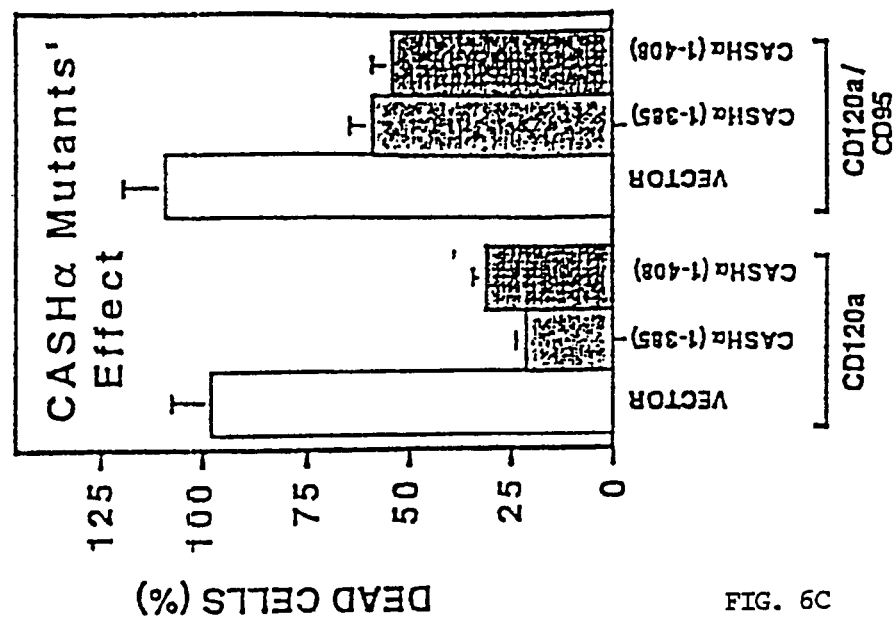
Figure 6B:
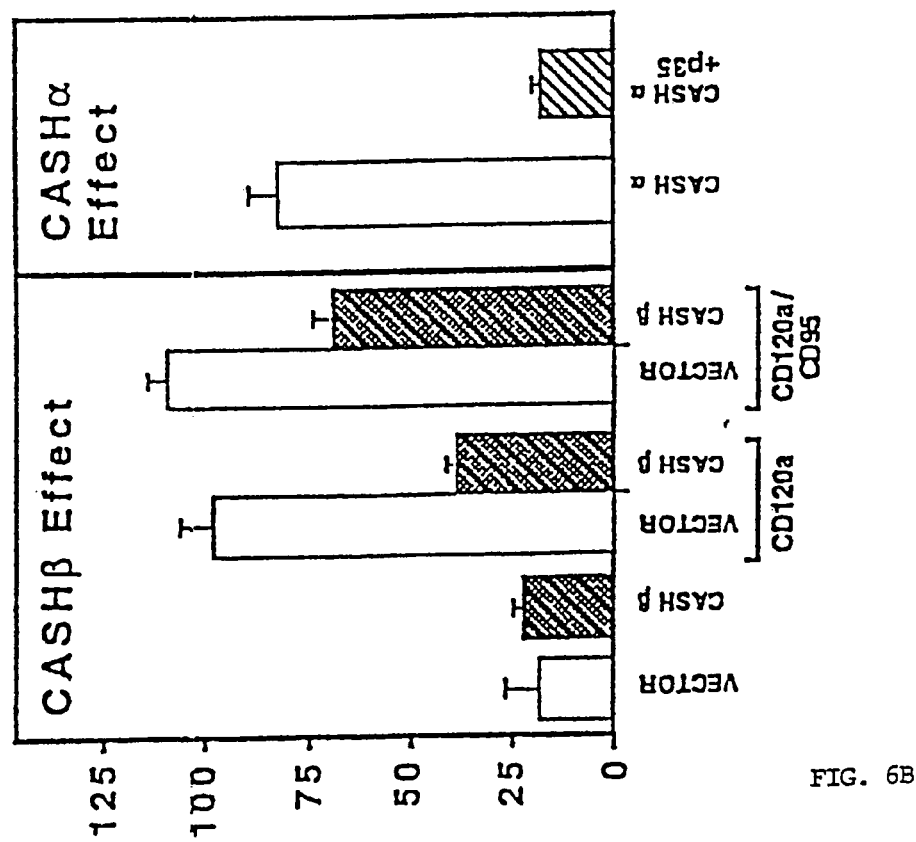
Figure 6D:
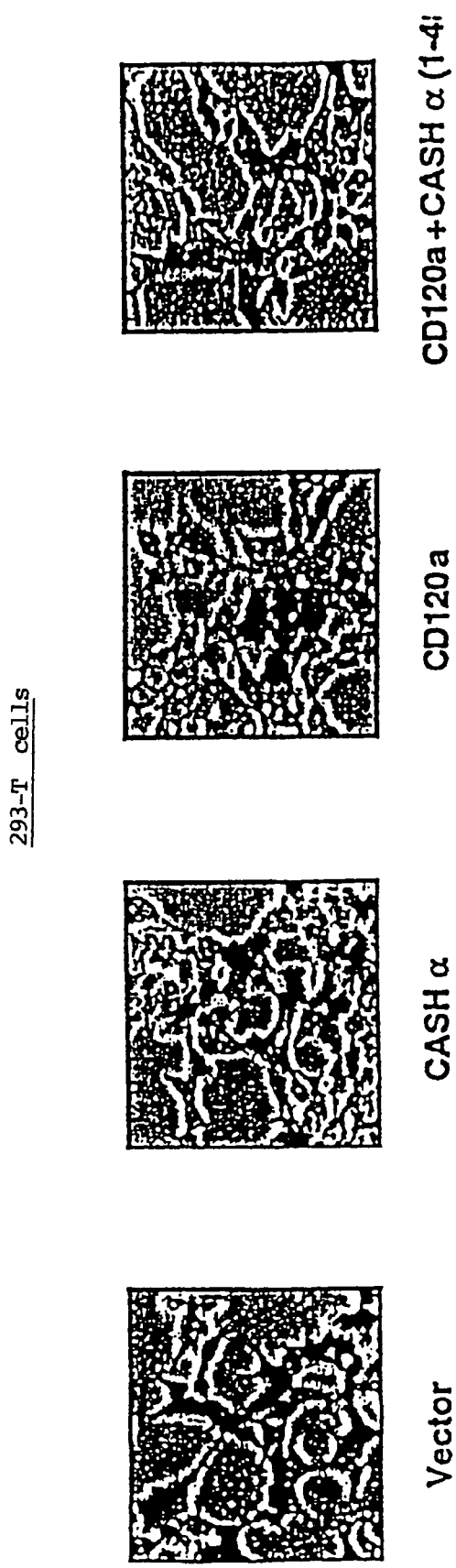

Following the above initial cloning and sequencing of G1, in particular the G1α and G1β isoforms, further analysis of these proteins was performed:

(ii) Northern Analysis and Additional Sequence Analysis:

Northern blot analysis revealed that the G1 protein exists in at least three distinct transcript sizes, 2, 2.4 and 4.4 kb, whose proportions vary greatly among different tissues (FIGS. 2A and 2B). To obtain the full-length cDNA of G1 (CASH), a human skin fibroblast cDNA library (Clontech) was screened with a cDNA probe corresponding to the G1 sequence. Two cDNA species, apparently corresponding to two splice variants of G1 were obtained (see also above). The proteins encoded by these two cDNAs shared the death-effector domain-containing N-terminal region, but their C-termini differed. One (G1β=CASHβ) had a short C-terminus, corresponding to that of the originally cloned cDNA. The other (GPα=CASHα) had a long C terminus.

The amino acid sequence in this longer C-terminal region of G1α showed rather high homology to those of the protease-precursor regions in MACH (CASP-8) and Mch4 (CASP-10) (see also FIGS. 1A-1C). However, G1α lacked several of the residues believed to be crucial for protease activity, suggesting that the protein may be devoid of cysteine protease activity. Interestingly, G1α contains a caspase-substrate sequence at the site corresponding to the proteolytic-processing site within the protease regions in MACH (CASP-8) and Mch4 (CASP-10) (shaded in FIGS. 1A-1C). Preliminary data suggest that G1α can indeed be cleaved at this site by MACH (data not shown). Based on the nucleotide sequence of an EST clone found to correspond to the mouse homologue of part of the 'death domain' (DED) region in G1, the cDNAs of both the mouse CASHα and CASHβ splice variants were cloned from mouse liver mRNA by RT-PCR. An EST clone (GenBank accession no. AA198928) was identified as the mouse homologue of part of the DED region in G1. Based on this sequence the mouse G1α (CASHα) and G1β (CASHβ) splice variants from mouse liver mRNA were cloned by RT-PCR. The reverse transcriptase reaction was performed with an oligo-dT adapter primer (5'-GACTCGAGTCTAGAGTCGAC(T)17-3') (SEQ ID NO:12) and the AMV reverse transcriptase (Promega), used according to the manufacturer's instructions. The first round of PCR was carried out with the Expand Long Template PCR System (Boehringer Mannheim) using the following sense and antisense primers 5'-GGCTTCTCGTGGTTCCCAGAGC-3' (SEQ ID NO:19), and 5'-GACTCGAGTCTAGAGTCGAC-3' (base pairs 1-20 of SEQ ID NO:12) (adapter) respectively. The second round was performed with Vent polymerase (NEB) using the nested sense primer: 5'-TGCTCTTCCTGTGTAGAGATG-3' (SEQ ID NO:20), and adapter.

Sequence comparison revealed high conservation throughout the G1α (CASHα) molecule (71% identity in DED region and 59% in protease homology region), suggesting that both the DED and protease-homology regions in the protein contribute to its function (see FIG. 1A-1C).

(iii) Two-hybrid Analysis for Binding Specificity of G1 Isoforms:

Two-hybrid testing of the interactive properties of G1α (CASHα) and G1β (CASHβ) (FIG. 3) revealed that both variants interact with MORT1/FADD and MACH (CASP-8), most probably through their shared DED regions. Notably, although initially cloned by two-hybrid screening for proteins that bind to Mch4 (CASP-10), G1β (CASHβ) was found in this test to bind weakly to Mch4 (CASP-10) and G1α (CASHα) appear to bind only weakly to Mch4. It should however be noted that the initial two-hybrid screen to clone the G1 proteins differed from this two-hybrid screen to assay binding specificity and hence, in reality it would appear that G1α and G1β both bind to MACH and Mch4 as the original cloning results show. The two G1 variants also self-associated and bound to each other, but did not bind RIP or TRADD (adapter proteins which, like MORT1/FADD, contain death domains but lack DEDs), nor did they bind to a number of irrelevant proteins (e.g. lamin) used as specificity controls.

To examine further the function of G1, its two variants were expressed transiently in HeLa and 293-T cells and there was assessed the effects of the transfected proteins on the p55-R (CD120a)-induced signaling for cytotoxicity triggered by TNF, or by overexpression of the receptor as well as on the FAS-R (CD95)-induced signaling for cytotoxicity triggered by antibody cross-linking of FAS-R, or by overexpression of a chimeric receptor comprised of the extracellular domain of p55-R (CD120a) and the intracellular domain of FAS-R (CD95) (see FIGS. 4A-4D). In both cell lines, expression of G1β (CASHβ) by itself had no effect on cell viability, but it strongly inhibited the induction of cell death by p55-R (CD120a) as well as by FAS-R (CD95). Expression of the G1α (CASHα) variant affected the two cell lines very differently. In HeLa cells it inhibited the cytotoxicity of p55-R (CD120a) and FAS-R (CD95), similarly to G1β (CASHβ). In the 293-T cells, however, it resulted in marked cytotoxicity. Similar cytotoxicity was observed when the G1α protein was expressed in 293-EBNA cells (not shown). This cytotoxic effect could be completely blocked by coexpression of p35, a baculovirus-derived caspase inhibitor (for p35 see also Clem et al., 1991; Xue and Horvitz, 1995).

To assess the contribution of the region of protease homology in G1α (CASHα) to its cytocidal effect, the functions of two mutants of the protein were examined. These mutants were: G1/CASHα (1-385) and G1/CASHα (1-408), with C-terminal deletions at the region corresponding to that part of the protease domain from which the small subunit of the mature protease is derived. Both mutants were devoid of any cytotoxic effect. Moreover, like G1β (CASHβ) they protected the 293 cells from death induction by p55-R (CD120a) and FAS-R (cd95) FIGS. 4C and 4D.

It should be noted that for the above procedures the following methods and materials were employed:

(i) The G1α (CASHα) deletion mutants and the p55-R/FAS-R (CD120a/CD95) chimera were produced by PCR and/or conventional cloning techniques. The G1 (CASH) splice variants, the FAS-R (CD95) or p55-R (CD120a) signaling-cascade proteins (all of human origin) and the baculovirus p35 protein were expressed in mammalian cells using the pcDNA3 expression vector (Invitrogen). β-galactosidase was expressed using the pCMV-β-gal vector (Promega).

(ii) The human embryonic kidney 293-T and 293 EBNA cells and human cervical carcinoma HeLa cells (HeLa-Fas; the HtTA-1 clone) stably expressing transfected human FAS-R (CD95) (established in present inventor's laboratory)

were grown in Dulbecco's modified Eagle's minimal essential medium supplemented with 10% fetal calf serum, nonessential amino acids, 100 U/ml penicillin and 100 mg/ml streptomycin.

The above findings indicate that G1 can interact with components of the signaling complexes of p55-R and FAS-R and that it affects death induction in a way that may differ depending on the identity of the splice variant of G1 and on the cell type in which it is expressed.

The inhibition of cytotoxicity induction by G1β, and in the case of the HeLa cells also by G1α, is apparently mediated by the 'death domain' (DED) region in this protein. It probably reflects competition of the DED of G1 with the corresponding regions in MACH (CASP-8) and Mch4 (CASP-10) for binding to MORT1/FADD.

With respect to the way in which CASHα causes death of the 293 cells, the ability of the p35 protein to block this cytotoxic effect indicates that the cytotoxicity is mediated by the activity of caspases. However, G1α, even though displaying marked sequence homology to the caspases, may actually lack cysteine-protease activity since it does not have several of the conserved caspase active-site residues. G1α may therefore act by activating other molecules that do have caspase activity.

Another possibility is that G1α, though unable to act alone as a protease, can still constitute part of an active protease molecule. Crystallographic studies of CASP-1 and CASP-3 structure indicate that the small and large protease subunits in each processed enzyme are derived from distinct proenzyme molecules (Walker et al., 1994; Wilson et al., 1994; Mittl et al., 1997; Rotonda et al., 1996). In view of the observed dependence of the G1α cytotoxic activity on intactness of the region corresponding to the small protease subunit (FIG. 6C), it may be that this region in G1α (CASHα) can associate with the large subunit region of certain caspase(s) in a way that results in reconstitution of an enzymatically active molecule. The resulting active heterotetramer should then be capable of activating other caspases, thus triggering cell death.

Further, it also arises (results not shown) that G1 has at least some homology to another protein called MYD88 which is involved in the signaling pathway mediated by IL-1. Thus, G1 may also be involved in other pathways initiated/mediated by other cytokines.

In view of the above mentioned concerning the cloning and isolation of G1 protein (at least two isoforms thereof) the following characteristics and uses of G1 arise:

(i) G1 was cloned by a two-hybrid screen as a molecule that binds the MORT-1-binding protein Mch4 and hence is possibly involved in modulation of the activity of Mch4 and MORT-1, and hence, by the mechanisms indicated above, G1 is possibly involved in the modulation of cellular events initiated by the FAS-R and p55-R. As Mch4 is capable of binding to MORT-1 and is directly involved in cell cytotoxicity and ultimately cell death, and also as some isoforms of Mch4 are known to inhibit cell death, it arises that G1 including its various isoforms may be directly or indirectly involved in both cell cytotoxicity and cell death, as well as, inhibition of cell death.

(ii) G1 apparently has an N-terminal region which contains two MORT modules homologous to the two MORT modules of MACH (see above reference Examples 1-3) and of Mch4. The presence of these MORT modules in G1 appear therefore to account for G1's ability to bind Mch4, and possibly also allow for the binding of G1 (or at least some of its isoforms) to MACH (or some isoforms thereof), as well as, to MORT-1 directly. Accordingly, G1 may be able to modulate the activity of MORT-1 (and, in turn, the activity of FAS-R and p55-R) directly, by direct binding to MORT-1, or indirectly by binding to Mch4 and/or to MACH, which, in turn, are known to bind MORT-1.

(iii) Analysis of the G1 sequence in the above noted databanks and screening has revealed also that G1 is apparently located close to the Mch4 and MACH loci on human chromosome no. 2, indicative of a close relationship between the genes encoding all of these proteins also at the chromosomal level.

(iv) At least some of the G1 isoforms (e.g. the G1α isoform of FIG. 1) have a region downstream of the MORT modules region that displays similarity with the enzymatic, i.e. protease, region of MACH and Mch4, and as such G1 may be a member of the CED3/ICE protease family.

(v) The presence of a protease-like region in at least some of the G1 isoforms (e.g. G1α) indicates that G1 or such isoforms thereof may be directly involved in cell cytotoxicity and inflammation caused by various stimuli including receptors of the TNF/NGF receptor family (e.g. FAS-R and p55-R) and others as well which act directly or indirectly via an intracellular protease activity to bring about cell cytotoxicity and inflammation.

(vi) G1 may act as an enhancer or augmentor of the activity of other proteins, such as, for example, MACH and Mch4 proteins (inclusive of their various isoforms), in the intracellular mechanisms leading to cell cytotoxicity, inflammation and other related effects as mediated by receptors of the TNF/NGF receptor family and others sharing common intracellular effectors. The enhancer or augmentor effect of G1 (or at +least some of its isoforms) may be by the binding of G1 to these other proteins (as noted above G1 binds to Mch4 and possibly also binds to MACH and MORT-1), thereby recruiting them to bind to MORT-1 (including MORT-1 self-association), or to act independently of MORT-1.

(vii) G1 may also act as an inhibitor of the activity of other proteins, and this may be by way of G1 being part of a complex of other proteins to which it binds (e.g. Mch4 and possibly also MACH and MORT-1) thereby affecting their cytotoxicity to the extent of inhibition of this activity. Further, in an analogous fashion to that mentioned above concerning some MACH isoforms as well as some isoforms of Mch4, there may also be isoforms of G1 which specifically have inhibitory activity. One such G1 isoform may be the G1β isoform shown in FIG. 2 which has two MORT MODULES but no apparent protease-like region of similarity to other known proteases.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Ahmad, M. et al., (1997) Cancer Research 57, 615-620.
Alnemri, E. S. et al. (1995) J. Biol. Chem. 270:4312-4317.
Barinaga, M. (1993) Science 262:1512-1514.
Beidler, J. et al., (1995) J. Biol. Chem. 270:16526-16528.
Berger, J. et al., (1988) Gene 66:1-10.
Beutler, B. and Cerami, C. (1987) NEJM: 316:379-385.
Bigda, J. et al. (1994) J. Exp. Med. 180:445-460.
Boldin, M. P. et al. (1995a) J. Biol. Chem. 270:337-341.
Boldin, M. P. et al. (1995b) J. Biol. Chem. 270:7795-7798.
Boldin, M. P. et al. (1996) Cell 85:803-815.
Brakebusch, C. et al. (1992) EMBO J., 11:943-950.
Brockhaus, M. et al. (1990) Proc. Natl. Acad. Sci. USA, 87:3127-3131.
Cantor, G. H. et al. (1993) Proc. Natl. Acad. Sci. USA 90:10932-6.
Cerreti, D. P. et al. (1992) Science 256:97-100.
Chen, C. J. et al. (1992) Ann. N.Y. Acad. Sci. 660:271-3.
Chinnaiyan et al. (1995) Cell 81:505-512.
Chinnaiyan et al. (1996) J. Biol. Chem. 271:4961-4965.
Cifone, M. G. et al. (1995) EMBO J. 14:5859-5868.
Clem, R. J. et al. (1991) Science 254, 1388-1390.
Clement, M. V. et al. (1994) J. Exp. Med. 180:557-567.
Crisell, P. et al., (1993) Nucleic Acids Res. (England) 21 (22):5251-5.
Current Protocols in Molecular Biology (Ausubel, F. M., Brent, R., Kingston, R. E., Moore, D. D., Seidman, J. G., Smith, J. A., Struhl, K., Albright, L. M., Coen, D. M. & Varki, A., eds.), (1994) pp. 8.1.1-8.1.6 and 16.7-16.7.8, Greene Publishing Associates, Inc. and Wiley & Sons, Inc., New York.
Dirks, W., et al., (1993) Gene 128:247-249.
Duan, H. and Dixit, V. M. (1997) Nature 385, 86-89.
Durfee, T. et al. (1993) Genes Dev. 7:555-569.
Eischen, C. M. et al. (1994) J. Immunol. 153:1947-1954.
Ellis, H. M. et al. (1986) Cell 44:817-829.
Enari, M. et al. (1995) Nature 375:78-81.
Engelmann, H. et al. (1990) J. Biol. Chem., 265:1531-1536.
Faucheu, C. et al. (1995) EMBO J. 14:1914-1922.
Fernandes-Alnemri, T. et al. (1994) J. Biol. Chem. 269: 30761-30764.
Fernandes-Alnemri, T. et al. (1995) Cancer Res. 55:2737-2742.
Fernandes-Alnemri, T. et al. (1996) Proc. Natl. Acad. Sci. USA 93:7464-7469.
Field, J. et al. (1988) Mol. Cell Biol. 8:2159-2165.
Fields, S. and Song, O. (1989) Nature, 340:245-246.
Frangioni, J. V. and Neel, B. G. (1993) Anal. Biochem. 210: 179-187.
Geysen, H. M. (1985) Immunol. Today 6:364-369.
Geysen, H. M. et al. (1987) J. Immunol. Meth. 102:259-274.
Gossen, M. and Boujard, H. (1992) Proc. Natl. Acad. Sci. USA, 89:5547-5551.
Grell, M. et al. (1994) Eur. J. Immunol. 24:2563-2566.
Heller, R. A. et al. (1990) Proc. Natl. Acad. Sci. USA, 87:6151-6155.
Henkart, P. A. (1996) Immunity 4:195-201.
Hohmann, H.-P. et al. (1989) J. Biol. Chem., 264:14927-14934.
Howard, A. D. et al. (1991) J. Immunol. 147:2964-2969.
Hsu, H. et al. (1995) Cell 81:495-504.
Hsu, H. et al. (1996) Cell 84:299-308.
Itoh, N. et al. (1991) Cell 66:233.
Itoh, N. and Nagata, S. (1993) J. Biol. Chem. 268:10932-7.
Joseph, S. and Burke, J. M. (1993) J. Biol. Chem. 268:24515-8.
Kamens, J. et al. (1995) J. Biol. Chem. 270:15250-15256.
Kaufmann, S. H. (1989) Cancer Res. 49:5870-5878.
Kaufmann, S. H. (1993) Cancer Res. 53:3976-3985.
Kischkel, F. C. et al. (1995) EMBO J. 14:5579-5588.
Koizumi, M. et al. (1993) Biol. Pharm. Bull (Japan) 16 (9): 879-83.
Kumar, S. et al. (1994) Genes Dev. 8:1613-1626.
Kumar, S. (1995) Trends Biochem Sci. 20:198-202.
Lazebnik, Y. A. et al. (1994) Nature 371:346-347.
Leithauser, F. et al. (1993) Lab Invest. 69:415-429.
Loetscher, H. et al. (1990) Cell, 61:351-359.
Los, M. et al. (1995) Nature 375:81-83.
Martin, S. J. et al. (1995) J. Biol. Chem. 270:6425-6428.
Mashima, T. et al. (1995) Biochem. Biophys. Res. Commun. 209:907-915.
Miller, B. E. et al. (1995) J. Immunol. 154:1331-1338.
Milligan, C. E. et al. (1995) Neuron 15:385-393.
Mittl, P. R. E. et al., (1997) J. Biol. Chem. 272, 6539-6547.
Miura, M. et al. (1995) Proc. Natl. Acad. Sci. USA 92:8318-8322.
Munday, N. A. et al. (1995) J. Biol. Chem. 270:15870-15876.
Muranishi, S. et al. (1991) Pharm. Research 8:649.
Muzio, M. et al. (1996) Cell 8, 817-827.
Nagata, S. and Golstein, P. (1995) Science 267, 1449-1456.
Nicholson, D. W. et al. (1995) Nature 376:37-43.
Nophar, Y. et al. (1990) EMBO J., 9:3269-3278.
Piquet, P. F. et al. (1987) J. Exp. Med., 166:1280-89.
Ray et al. (1992) Cell 69:597-604.
Rotonda, J. et al., (1996) Nat-Struct-Biol. 3, 619-25.
Ruggiero, V. et al. (1987) Cell Immunol. 107:317-325.
Sambrook et al. (1989) *Molecular Cloning: A Laboratory Manual*, Cold Spring Harbor Laboratory Press, Cold Spring Harbor, N.Y.
Schall, T. J. et al. (1990) Cell, 61:361-370.
Schlegel, et al. (1996) J. Biol. Chem. 271:1841-1844.
Schulze-Osthoff, K. et al. (1994) EMBO J. 13:4587-4596.
Shimayama, T. et al., (1993) Nucleic Acids Symp. Ser. 29:177-8
Shore, S. K. et al. (1993) Oncogene 8:3183-8.
Sleath, P. R. et al. (1990) J. Biol. Chem. 265:14526-14528.

Smith, C. A. et al. (1990) Science, 248:1019-1023.
Song, H. Y. et al. (1994) J. Biol. Chem. 269:22492-22495.
Srinivasula, S. M. et al. (1996) Proc. Natl. Acad. Sci. USA 93:14486-14491.
Stanger, B. Z. et al. (1995) Cell 81:513-523.
Tartaglia, L. A. et al. (1993) Cell, 74:845-853.
Tewari, M. et al. (1995) J. Biol. Chem. 270:3255-3260.
Tewari, M. et al. (1995a) J. Biol. Chem. 270:18738-18741.
Tewari, M. et al. (1995b) Cell 81:1-20.
Thornberry, N. A. et al. (1992) Nature 356:768-774.
Thornberry, N. A. et al. (1994) Biochemistry 33:3934-3940.
Tracey, J. T. et al. (1987) Nature, 330:662-664.
Van Criekinge, W. et al. (1996) J. Biol. Chem. 271, 27245-8.
Vandenabeele, P. et al. (1995) Trends Cell Biol. 5:392-400.
Vassalli, P. (1992) Ann. Rev. Immunol. 10:411-452.
Vincent, C. and Dixit, V. M. (1997) J.B.C. 272, 6578-6583.
Walker, N. P. et al. (1994) Cell 78, 343-352.
Wallach, D. (1984) J. Immunol. 132:2464-9.
Wallach, D. (1986) In: Interferon 7 (Ion Gresser, ed.), pp. 83-122, Academic Press, London.
Wallach, D. et al. (1994) Cytokine 6:556.
Wang, L. et al. (1994) Cell 78:739-750.
Watanabe-Fukunaga, R. et al. (1992) Nature, 356:314-317.
Watanabe, F. R. et al. (1992) J. Immunol. 148:1274-1279.
Weitzen, M. et al. (1980) J. Immunol. 125:719-724.
Wilks, A. F. et al. (1989) Proc. Natl. Acad. Sci. USA, 86: 1603-1607.
Wilson, K. P. et al., (1994) Nature 370, 270-5.
Wong et al. (1994) J. Immunol. 152:1751-1755.
Xue, D. et al. (1995) Nature 377:248-251.
Yonehara, S. et al. (1989) J. Exp. Med. 169:1747-1756.
Yuan, J. et al. (1993) Cell 75:641-652.
Zaccharia, S. et al. (1991) Eur. J. Pharmacol. 203:353-357.
Zhao, J. J. and Pick, L. (1993) Nature (England) 365:448-51.

What is claimed is:

1. An isolated molecule comprising a DNA sequence encoding a polypeptide which is capable of binding to one or more of MORT-1, MACH and MORT-1 binding protein Mch4, which polypeptide has the amino acid sequence of:
   (a) a G1 protein isoform whose sequence is that of SEQ ID NO:4;
   (b) an analog of (a) which differs from the sequence of (a) by no more than ten changes in the amino acid sequence of (a), each said change being a substitution, deletion and/or insertion of a single amino acid, which analog is capable of binding to one or more of MORT-1, MACH and MORT-1 binding protein Mch4; or
   (c) a derivative of (a) or (b) by modification of a functional group which occurs as a side chain or an N- or C-terminal group of one or more amino acid residues thereof without changing one amino acid to another of the twenty commonly occurring natural amino acids, which derivative is capable of binding to one or more of MORT-1, MACH, and MORT-1 binding protein Mch4.

2. An isolated molecule in accordance with claim 1, wherein said polypeptide has the amino acid sequence of said G1 protein isoform of SEQ ID NO:4.

3. An isolated molecule in accordance with claim 2, wherein the DNA sequence encoding said G1 protein isoform is SEQ ID NO:3.

4. An isolated molecule in accordance with claim 1, wherein the polypeptide has the amino acid sequence of (b), which is an analog that differs from the sequence of (a) by no more than ten changes in the amino acid sequence of (a), each said change being a deletion and/or insertion of a single amino acid, which analog is capable of binding to one or more of MORT-1, MACH, and MORT-1 binding protein Mch4.

5. An isolated molecule in accordance with claim 1, wherein the polypeptide has the amino acid sequence of (b), which is an analog that differs from the sequence of (a) by the substitution, deletion or insertion of a single amino acid residue, which analog is capable of binding to one or more of MORT-1, MACH, and MORT-1 binding protein Mch4.

6. An isolated molecule in accordance with claim 1, comprising a DNA sequence encoding a G1 isoform whose sequence is that of SEQ ID NO:4, which polypeptide is capable of binding to one or more of MORT-1, MACH, and MORT-1 binding protein Mch4.

7. An isolated molecule in accordance with claim 6, wherein the DNA sequence encoding said G1 protein isoform is that of SEQ ID NO:3.

8. A vector comprising the molecule in accordance with claim 6.

9. An isolated host cell transformed with the vector in accordance with claim 8.

10. A method for producing a polypeptide which has the amino acid sequence of a G1 protein isoform whose sequence is that of SEQ ID NO:4, which polypeptide is capable of binding to one or more of MORT-1, MACH, and MORT-1 binding protein Mch4, comprising:
   growing the host cell in accordance with claim 9 under conditions suitable for the expression of an expression product;
   effecting post-translational modifications of said expression product as necessary for obtaining said polypeptide; and
   isolating said polypeptide.

11. A vector comprising the molecule in accordance with claim 1.

12. A vector in accordance with claim 11 capable of being expressed in a eukaryotic host cell.

13. A vector in accordance with claim 11 capable of being expressed in a prokaryotic host cell.

14. An isolated host cell transformed with the vector in accordance with claim 11.

15. A method for producing a polypeptide which is capable of binding to one or more of MORT-1, MACH and MORT-1 binding protein Mch4, comprising:
   growing the host cell in accordance with claim 14 under conditions suitable for the expression of an expression product;
   effecting post-translational modifications of said expression product as necessary for obtaining said polypeptide; and
   isolating said polypeptide.

16. An isolated molecule consisting of a DNA sequence encoding a fragment of a G1 protein isoform of SEQ ID NO:4, which fragment is capable of binding to one or mere of MORT-1, MACH and MORT-1 binding protein Mch4.

17. A vector comprising the molecule in accordance with claim 16.

18. A vector in accordance with claim 17 capable of being expressed in a eukaryotic host cell.

19. A vector in accordance with claim 17 capable of being expressed in a prokaryotic host cell.

20. An isolated host cell transformed with the vector in accordance with claim 17.

21. A method for producing a polypeptide which is capable of binding to one or more of MORT-1, MACH and MORT-1 binding protein Mch4, comprising:
   growing the host cell in accordance with claim 20 under conditions suitable for the expression of an expression product;
   effecting post-translational modifications of said expression product as necessary for obtaining said polypeptide; and
   isolating said polypeptide.

* * * * *